US012673032B2

(12) United States Patent
Das

(10) Patent No.: US 12,673,032 B2
(45) Date of Patent: Jul. 7, 2026

(54) EXPLOITING ESTROGEN RECEPTOR BETA AND TP53 INTERACTION AS A NEW THERAPEUTIC STRATEGY FOR CANCER

(71) Applicant: Health Research, Inc.

(72) Inventor: Gokul M. Das, Buffalo, NY (US)

(73) Assignee: Health Research, Inc., Buffalo, NY (US)

( * ) Notice: Subject to any disclaimer, the term of this patent is extended or adjusted under 35 U.S.C. 154(b) by 814 days.

(21) Appl. No.: 17/291,211

(22) PCT Filed: Nov. 7, 2019

(86) PCT No.: PCT/US2019/060248
§ 371 (c)(1),
(2) Date: May 4, 2021

(87) PCT Pub. No.: WO2020/097317
PCT Pub. Date: May 14, 2020

(65) Prior Publication Data
US 2022/0125744 A1    Apr. 28, 2022

Related U.S. Application Data

(60) Provisional application No. 62/756,699, filed on Nov. 7, 2018.

(51) Int. Cl.
| | |
|---|---|
| *A61K 31/138* | (2006.01) |
| *A61K 45/06* | (2006.01) |
| *A61P 35/00* | (2006.01) |

(52) U.S. Cl.
CPC ............ *A61K 31/138* (2013.01); *A61K 45/06* (2013.01); *A61P 35/00* (2018.01)

(58) Field of Classification Search
CPC ................................................. A61K 31/138
See application file for complete search history.

(56) References Cited

FOREIGN PATENT DOCUMENTS

WO    WO-2008099144 A2    8/2008

OTHER PUBLICATIONS

Das et al., Abstract 3748: p53 Status as a Determinant of Functional

Duality of Estrogen Receptor Beta in Breast Cancer: Therapeutic Implications, Jul. 2018, Cancer Research 78(13 Supplement):3748-3748.*
Early Breast Cancer Trialists' Collaborative Group (EBCTCG), Effects of chemotherapy and hormonal therapy for early breast cancer on recurrence and 15-year survival: an overview of the randomised trials, The Lancet, vol. 365, Issue 9472, May 14-20, 2005, pp. 1687-1717.*
Mishra et al., Fulvestrant Inhibits Growth of Triple Negative Breast Cancer and Synergizes With Tamoxifen in ER Positive Breast Cancer by Up-Regulation of ER, Oncotarget, vol. 7, No. 35: 56876-56888, Jul. 28, 2018.*
Lu et al., Estrogen Receptor-β Modulation of the ERα-p53 Loop Regulating Gene Expression, Proliferation, and Apoptosis in Breast Cancer, Horm Cancer. Aug. 2017; 8(4): 230-242.*
Quyang et al., Inhibitory effects of tamoxifen and doxorubicin, alone and in combination, on the proliferation of the MG63 human osteosarcoma cell line, Oncol Lett. Jul. 24, 2013;6(4):970-976.*
Al-Bader, Analysis of estrogen receptor isoforms and variants in breast cancer cell lines, Exp Ther Med. Mar. 10, 2011;2(3):537-544.*
Communication: The extended European search report includes, pursuant to Rule 62 EPC, the supplementary European search report (Art. 153(7) EPC) and the European search opinion. Application No. 19881211.7-1111 / 3876922 PCT/US201 9060248, dated May 12, 2022.
PCT Notification Concerning Transmittal of International Preliminary Report on Patentability dated May 20, 2021, together with the PCT International Preliminary Report on Patentability and the Written Opinion of the International Searching Authority for corresponding application PCT/US19/60248 dated Apr. 6, 2020.

* cited by examiner

*Primary Examiner* — Svetlana M Ivanova
(74) *Attorney, Agent, or Firm* — Harris Beach Murtha Cullina PLLC; Laura W. Smalley

(57) ABSTRACT

To induce cancer cell death, cancer cells are selected that express estrogen-receptor β (ERβ) and mutant tumor protein 53 (TP53). An agent that increases ERβ protein expression is administered to the cells to induce cell death. To treat a subject having a cancer that is characterized by cancer cells expressing ERβ and mutant TP53, an agent that increases ERβ protein expression is administered to induce cell death in the cancer cells. To increase estrogen receptor β (ERβ) expression levels in a subject having low ERβ expression levels, tamoxifen is administered to increase ERβ protein levels in the subject. To treat a subject having cancer cells expressing estrogen-receptor β (ERβ) and wildtype tumor protein 53 (TP53), an agent that inhibits ERβ and TP53 binding interaction is administered to induce cell death in the cancer cells of the subject.

6 Claims, 61 Drawing Sheets

Specification includes a Sequence Listing.

FIG. 1E
FIG. 1F
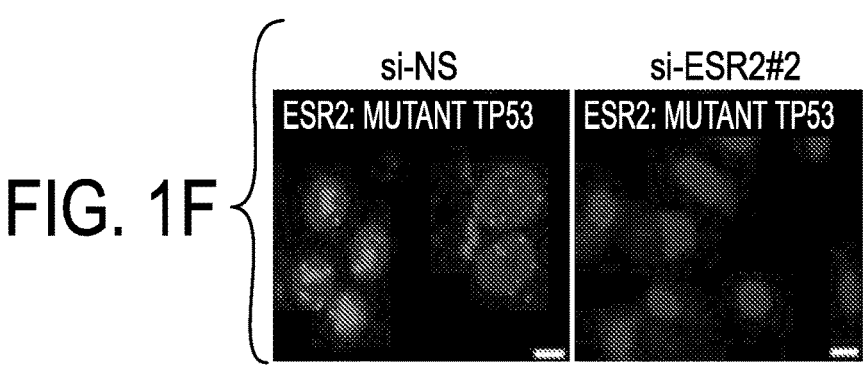
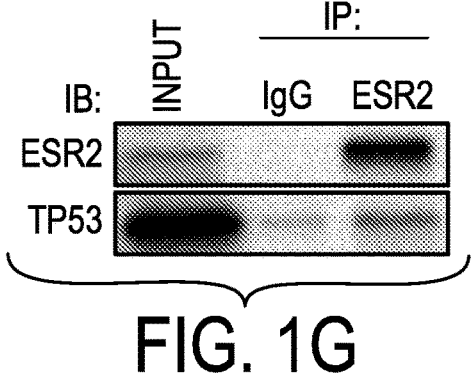
FIG. 1G

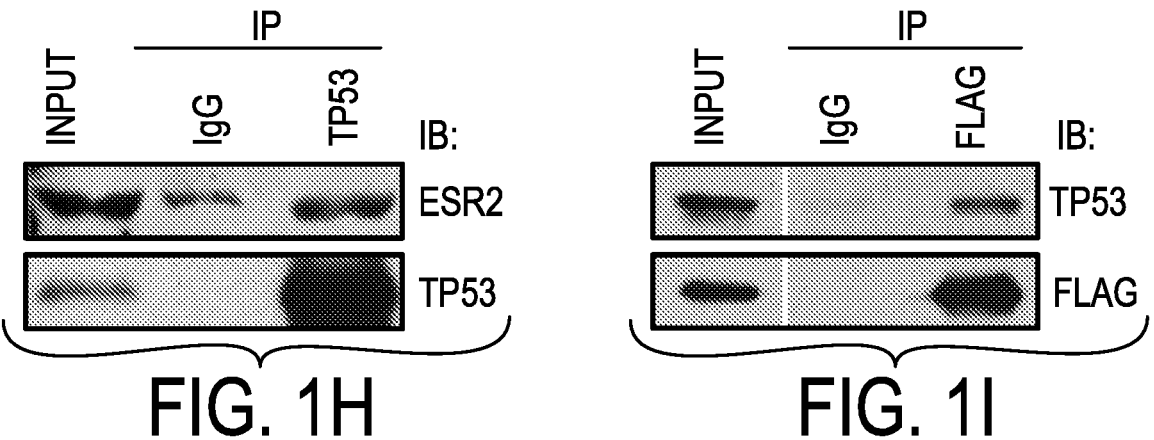
FIG. 1H
FIG. 1I
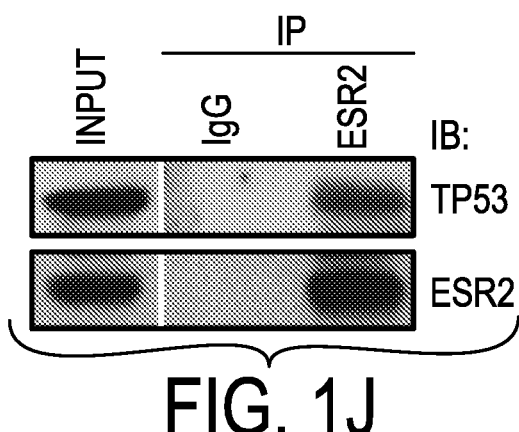
FIG. 1J
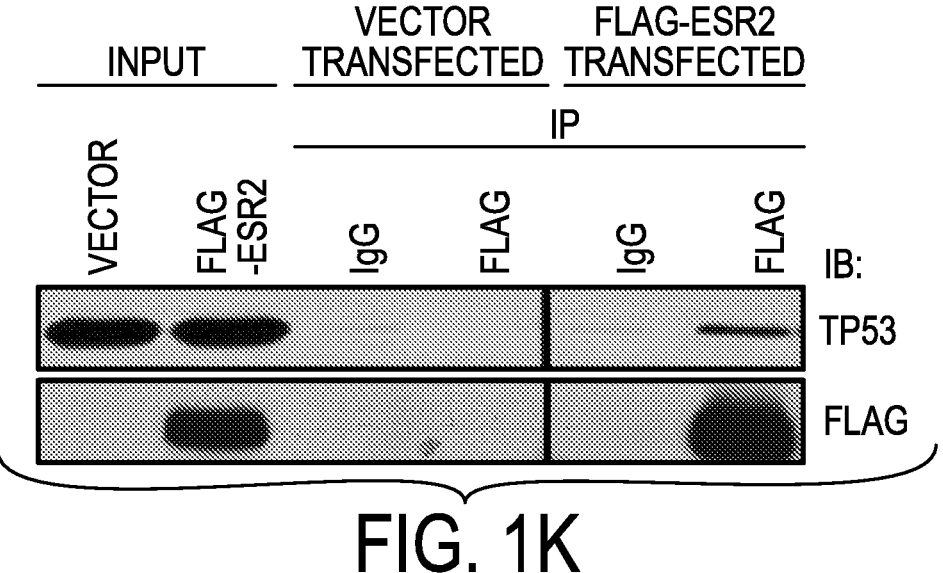
FIG. 1K

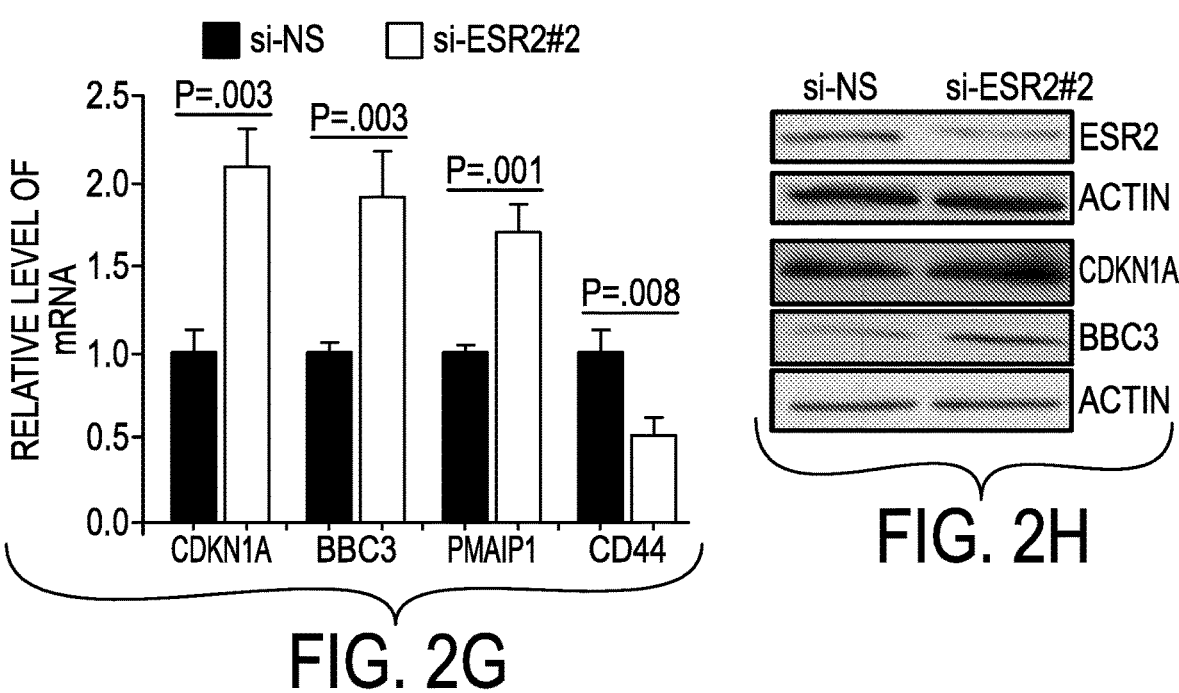
FIG. 2G
FIG. 2H
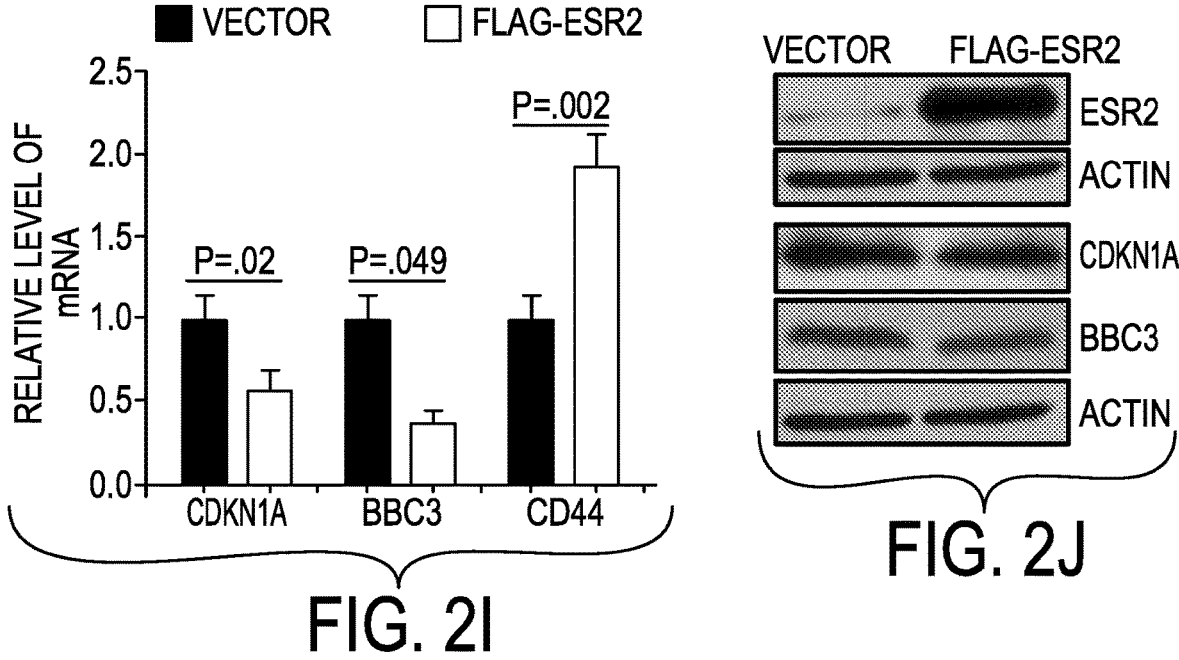
FIG. 2I
FIG. 2J

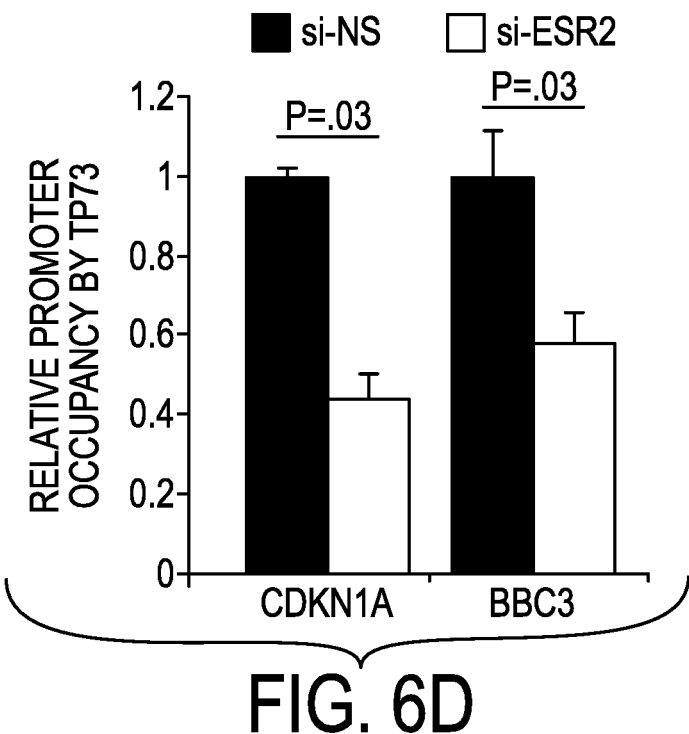
FIG. 6D
FIG. 6E
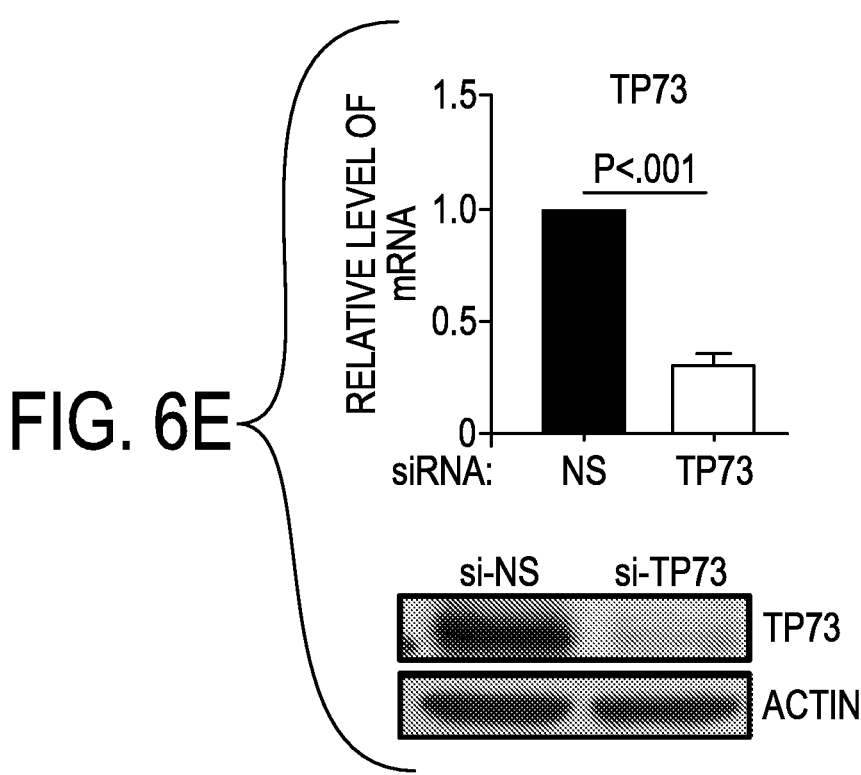

si-NS                                si-ESR2#2

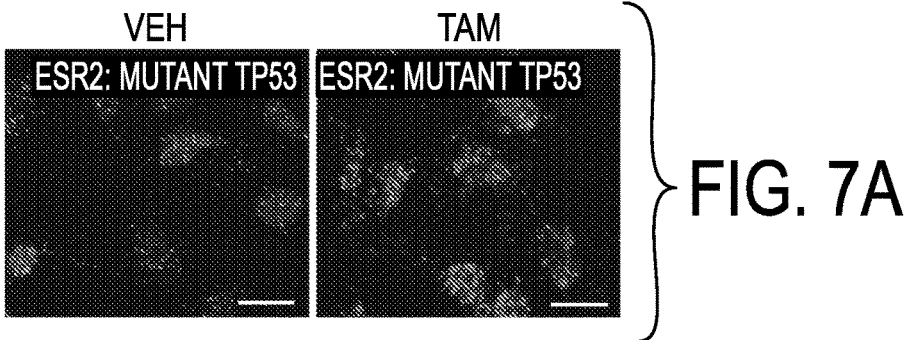
FIG. 7A
FIG. 7B
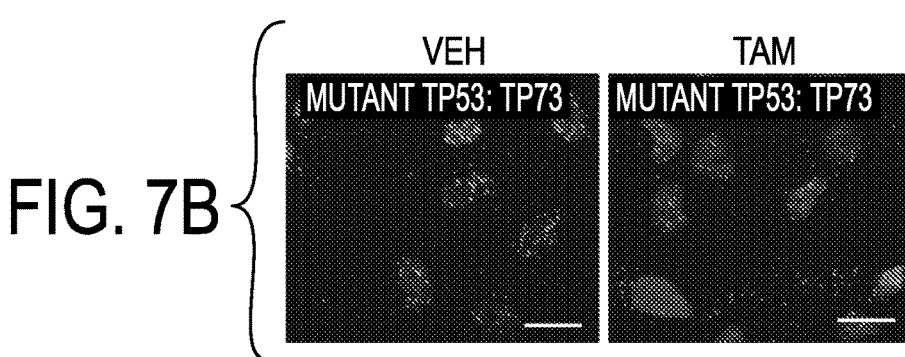
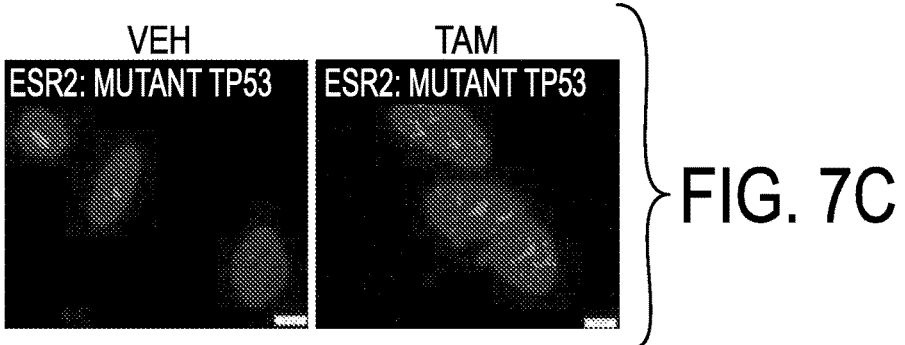
FIG. 7C
FIG. 7D
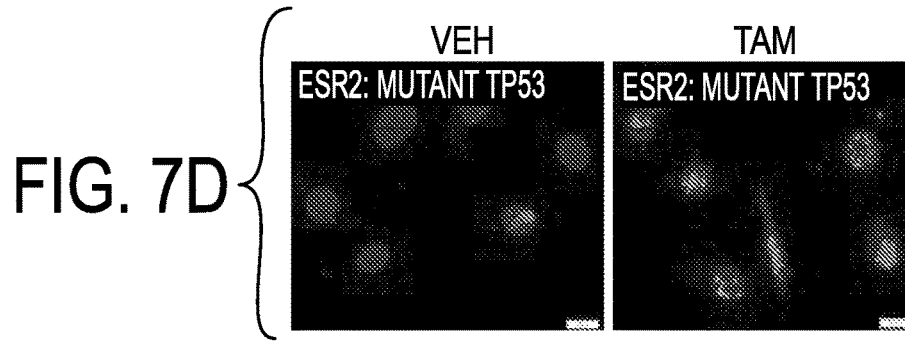

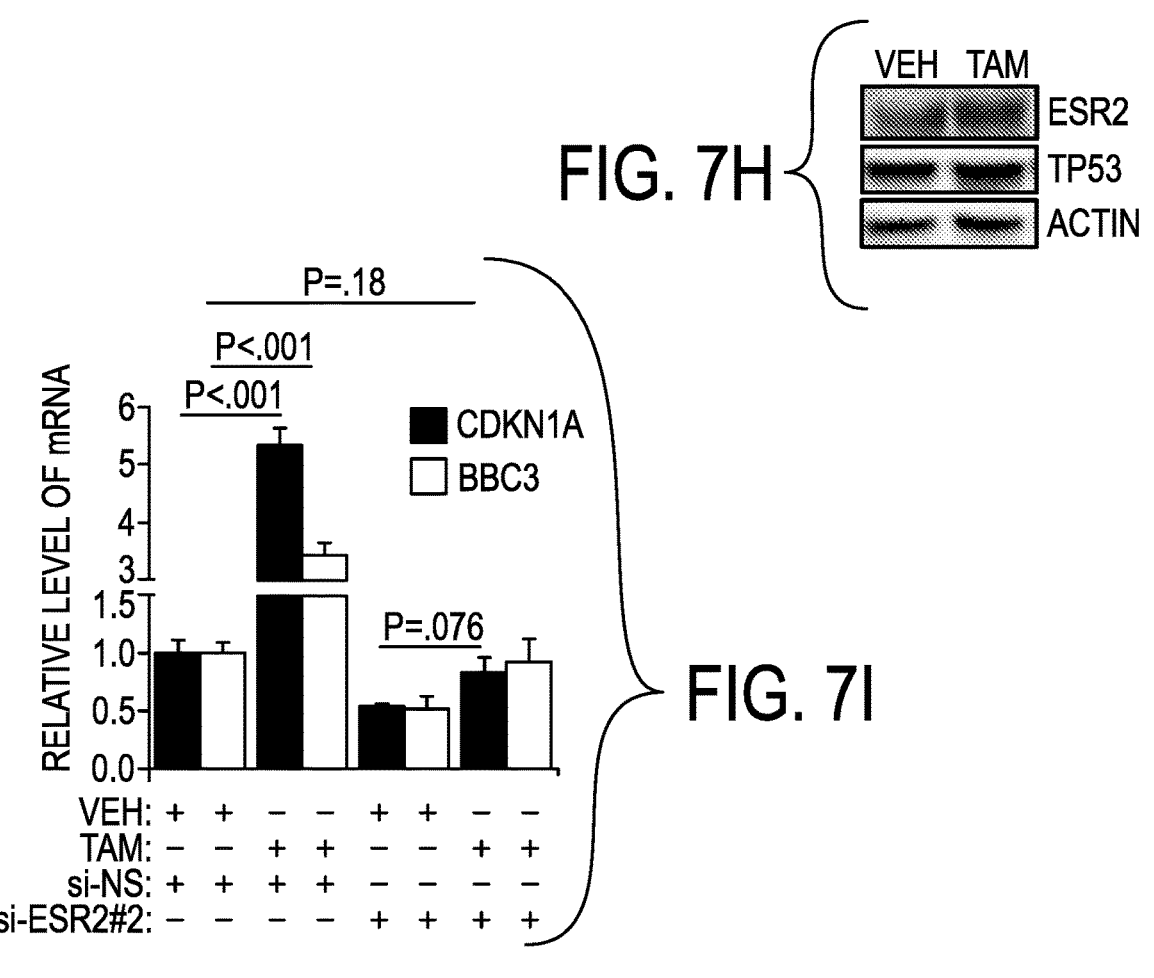
FIG. 7H
FIG. 7I
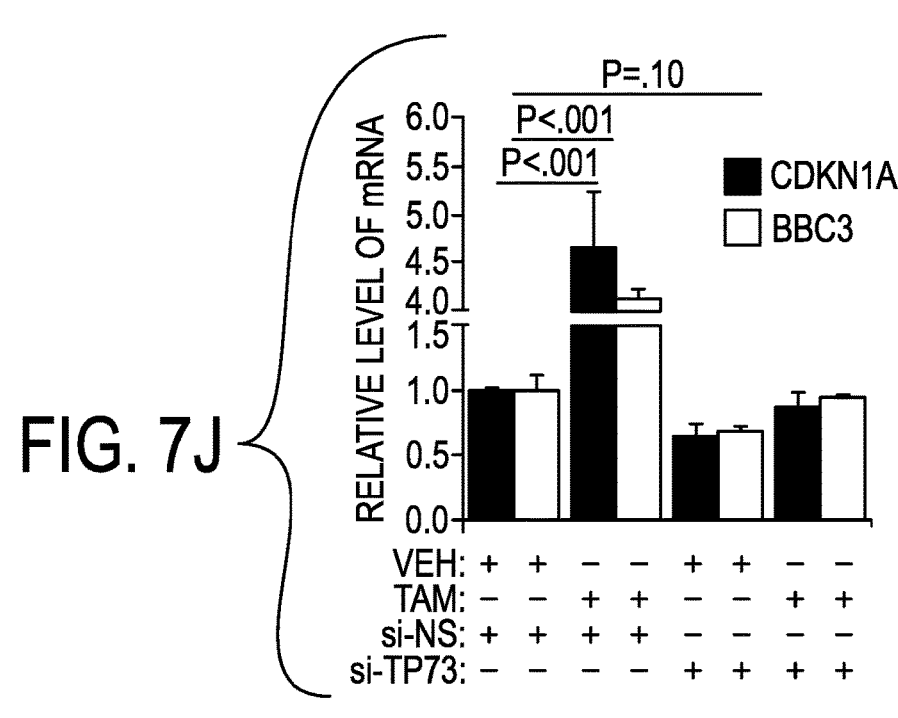
FIG. 7J

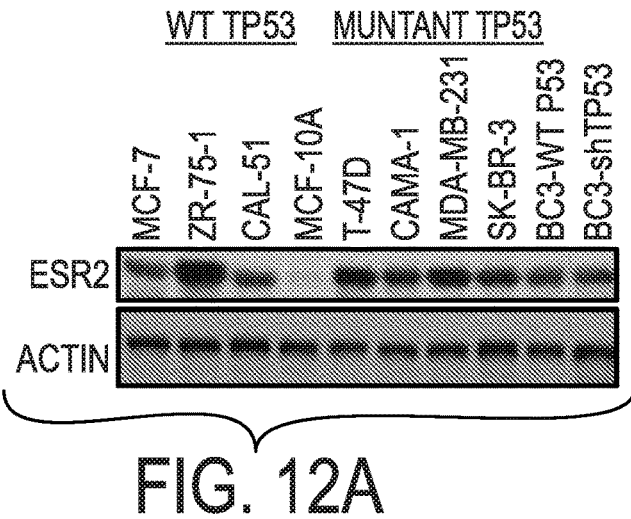
FIG. 12A
FIG. 12B
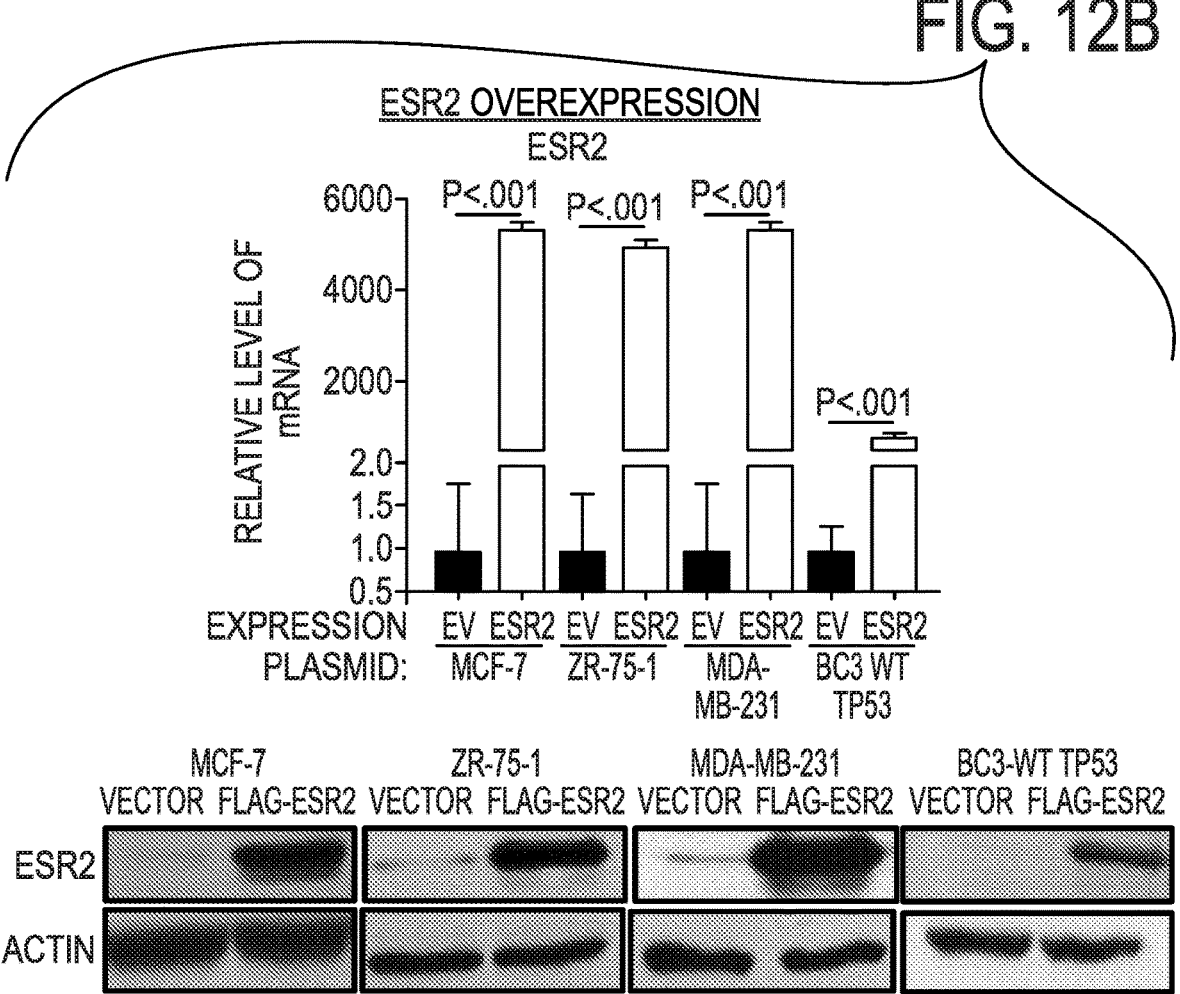

| CELL LINES | si-NS | siESR2 KNOCKDOWN | VECTOR | ESR2 OVEREXPRESSION |
|---|---|---|---|---|
| MCF-7 | 29.05 ± 0.12 | 30.44 ± 0.13 | 29.15 ± 0.80 | 15.20 ± 3.22 |
| ZR-75-1 | 28.13 ± 0.13 | 30.19 ± 0.14 | 28.74 ± 0.66 | 19.61 ± 2.14 |
| MDA-MB-231 | 25.17 ± 0.12 | 28.14 ± 0.18 | 28.17 ± 0.76 | 19.50 ± 3.10 |
| BC3 WT TP53 | 28.41 ± 0.20 | 30.68 ± 0.15 | 29.21 ± 0.26 | 18.37 ± 2.47 |

R196

TP53 EXON 6

ORIGINAL WT SEQUENCE: ctggcccctcctcagcatcttatcc  gagtggaaggaaatttgcgtgtggagtatt

CLONE 1 (-1bp): CTGGCCCCTCCTCAGCATCTTATC-☐GAGTGGAAGGAAATTTGCGTGTGGAGTATTT

CLONE 2 (+1bp): CTGGCCCCTCCTCAGCATCTTATCC☐AGAGTGGAAGGAAATTTGCGTGTGGAGTATTT

SEQ ID NO: 40
SEQ ID NO: 41
SEQ ID NO: 42

MDA-MB-231-LM-p53KO (GRAY LINE) DOXO ALONE $IC_{50}$= 1.049 ± 0.25 $\mu$M
(BLACK LINE) DOXO+ 4OHT $IC_{50}$= 0.15 ± 0.02 $\mu$M (GRAY LINE) DOXO ALONE $IC_{50}$= 0.10 ± 0.01 $\mu$M
(BLACK LINE) DOXO+ 4OHT $IC_{50}$= 0.14 ± 0.02 $\mu$M

SEQUENCE LISTING

```
<160> NUMBER OF SEQ ID NOS: 42

<210> SEQ ID NO 1
<211> LENGTH: 43
<212> TYPE: DNA
<213> ORGANISM: Artificial Sequence
<220> FEATURE:
<223> OTHER INFORMATION: Synthetic sequence

<400> SEQUENCE: 1
ccatagcggc cgccaccatg gatataaaaa ctcaccatct agc                 43

<210> SEQ ID NO 2
<211> LENGTH: 91
<212> TYPE: DNA
<213> ORGANISM: Artificial Sequence
<220> FEATURE:
<223> OTHER INFORMATION: Synthetic sequence

<400> SEQUENCE: 2
ggtcaacgcg ttcaagcgta atctggaaca tcgtatgggt aagcgtaatc tggaacatcg    60
tatgggtact gagactgtgg gttctgggag c                                  91

<210> SEQ ID NO 3
<211> LENGTH: 24
<212> TYPE: DNA
<213> ORGANISM: Artificial Sequence
<220> FEATURE:
<223> OTHER INFORMATION: Synthetic sequence

<400> SEQUENCE: 3
cctatgtaga cagccaccat gaat                                          24

<210> SEQ ID NO 4
<211> LENGTH: 24
<212> TYPE: DNA
<213> ORGANISM: Artificial Sequence
<220> FEATURE:
<223> OTHER INFORMATION: Synthetic sequence

<400> SEQUENCE: 4
cccacctccc aagttagtga catt                                          24

<210> SEQ ID NO 5
<211> LENGTH: 22
<212> TYPE: DNA
<213> ORGANISM: Artificial Sequence
<220> FEATURE:
<223> OTHER INFORMATION: Synthetic sequence

<400> SEQUENCE: 5
gctttggttt gggtgattgc ca                                            22

<210> SEQ ID NO 6
<211> LENGTH: 21
<212> TYPE: DNA
```

<213> ORGANISM: Artificial Sequence
<220> FEATURE:
<223> OTHER INFORMATION: Synthetic sequence

<400> SEQUENCE: 6
cgttcaagcg taatctggaa c                                              21

<210> SEQ ID NO 7
<211> LENGTH: 21
<212> TYPE: DNA
<213> ORGANISM: Artificial Sequence
<220> FEATURE:
<223> OTHER INFORMATION: Synthetic sequence

<400> SEQUENCE: 7
cgatgctttg gtttgggtga t                                              21

<210> SEQ ID NO 8
<211> LENGTH: 21
<212> TYPE: DNA
<213> ORGANISM: Artificial Sequence
<220> FEATURE:
<223> OTHER INFORMATION: Synthetic sequence

<400> SEQUENCE: 8
gccctctttg cttttactgt c                                              21

<210> SEQ ID NO 9
<211> LENGTH: 21
<212> TYPE: DNA
<213> ORGANISM: Artificial Sequence
<220> FEATURE:
<223> OTHER INFORMATION: Synthetic sequence

<400> SEQUENCE: 9
ctttaggcca ccgagttgat t                                              21

<210> SEQ ID NO 10
<211> LENGTH: 23
<212> TYPE: DNA
<213> ORGANISM: Artificial Sequence
<220> FEATURE:
<223> OTHER INFORMATION: Synthetic sequence

<400> SEQUENCE: 10
atgggtcaga aggattccta tgt                                            23

<210> SEQ ID NO 11
<211> LENGTH: 22
<212> TYPE: DNA
<213> ORGANISM: Artificial Sequence
<220> FEATURE:
<223> OTHER INFORMATION: Synthetic sequence

<400> SEQUENCE: 11
aaggtctcaa acatgatctg gg                                             22

<210> SEQ ID NO 12
<211> LENGTH: 22
<212> TYPE: DNA
<213> ORGANISM: Artificial Sequence
<220> FEATURE:
<223> OTHER INFORMATION: Synthetic sequence

<400> SEQUENCE: 12
gagactctca gggtcgaaaa cg                                             22

```
<210> SEQ ID NO 13
<211> LENGTH: 20
<212> TYPE: DNA
<213> ORGANISM: Artificial Sequence
<220> FEATURE:
<223> OTHER INFORMATION: Synthetic sequence

<400> SEQUENCE: 13
gatgtagagc gggcctttga                                                    20

<210> SEQ ID NO 14
<211> LENGTH: 20
<212> TYPE: DNA
<213> ORGANISM: Artificial Sequence
<220> FEATURE:
<223> OTHER INFORMATION: Synthetic sequence

<400> SEQUENCE: 14
atgcctgcct caccttcatc                                                    20

<210> SEQ ID NO 15
<211> LENGTH: 23
<212> TYPE: DNA
<213> ORGANISM: Artificial Sequence
<220> FEATURE:
<223> OTHER INFORMATION: Synthetic sequence

<400> SEQUENCE: 15
tcacacgtcg ctctctctaa acc                                                23

<210> SEQ ID NO 16
<211> LENGTH: 21
<212> TYPE: DNA
<213> ORGANISM: Artificial Sequence
<220> FEATURE:
<223> OTHER INFORMATION: Synthetic sequence

<400> SEQUENCE: 16
gtgagcgagc agaggcttaa g                                                  21

<210> SEQ ID NO 17
<211> LENGTH: 18
<212> TYPE: DNA
<213> ORGANISM: Artificial Sequence
<220> FEATURE:
<223> OTHER INFORMATION: Synthetic sequence

<400> SEQUENCE: 17
gagcccttgg acggcttt                                                      18

<210> SEQ ID NO 18
<211> LENGTH: 22
<212> TYPE: DNA
<213> ORGANISM: Artificial Sequence
<220> FEATURE:
<223> OTHER INFORMATION: Synthetic sequence

<400> SEQUENCE: 18
atgaatgcac cttcacattc ct                                                 22

<210> SEQ ID NO 19
<211> LENGTH: 21
<212> TYPE: DNA
<213> ORGANISM: Artificial Sequence
<220> FEATURE:
```

-continued

```
<223> OTHER INFORMATION: Synthetic sequence

<400> SEQUENCE: 19
tccagcagag ctggaagtcg a                                        21

<210> SEQ ID NO 20
<211> LENGTH: 20
<212> TYPE: DNA
<213> ORGANISM: Artificial Sequence
<220> FEATURE:
<223> OTHER INFORMATION: Synthetic sequence

<400> SEQUENCE: 20
ccacgtggag aaaaatggtc                                          20

<210> SEQ ID NO 21
<211> LENGTH: 19
<212> TYPE: DNA
<213> ORGANISM: Artificial Sequence
<220> FEATURE:
<223> OTHER INFORMATION: Synthetic sequence

<400> SEQUENCE: 21
cattgggcag gtctgtgac                                           19

<210> SEQ ID NO 22
<211> LENGTH: 20
<212> TYPE: DNA
<213> ORGANISM: Artificial Sequence
<220> FEATURE:
<223> OTHER INFORMATION: Synthetic sequence

<400> SEQUENCE: 22
aacacagact cgcgttgcaa                                          20

<210> SEQ ID NO 23
<211> LENGTH: 21
<212> TYPE: DNA
<213> ORGANISM: Artificial Sequence
<220> FEATURE:
<223> OTHER INFORMATION: Synthetic sequence

<400> SEQUENCE: 23
cggcttgtca catctgcaag t                                        21

<210> SEQ ID NO 24
<211> LENGTH: 24
<212> TYPE: DNA
<213> ORGANISM: Artificial Sequence
<220> FEATURE:
<223> OTHER INFORMATION: Synthetic sequence

<400> SEQUENCE: 24
cagagtgaga ccttgtctgt ctcc                                     24

<210> SEQ ID NO 25
<211> LENGTH: 26
<212> TYPE: DNA
<213> ORGANISM: Artificial Sequence
<220> FEATURE:
<223> OTHER INFORMATION: Synthetic sequence

<400> SEQUENCE: 25
cagaagatgc atgcaacagc accttg                                   26
```

```
<210> SEQ ID NO 26
<211> LENGTH: 20
<212> TYPE: DNA
<213> ORGANISM: Artificial Sequence
<220> FEATURE:
<223> OTHER INFORMATION: Synthetic sequence

<400> SEQUENCE: 26
caggctgtgg ctctgattgg                                                        20

<210> SEQ ID NO 27
<211> LENGTH: 21
<212> TYPE: DNA
<213> ORGANISM: Artificial Sequence
<220> FEATURE:
<223> OTHER INFORMATION: Synthetic sequence

<400> SEQUENCE: 27
cctcacctga aaacaggcag c                                                      21

<210> SEQ ID NO 28
<211> LENGTH: 20
<212> TYPE: DNA
<213> ORGANISM: Artificial Sequence
<220> FEATURE:
<223> OTHER INFORMATION: Synthetic sequence

<400> SEQUENCE: 28
gcgagactgt ggccttgtgt                                                        20

<210> SEQ ID NO 29
<211> LENGTH: 21
<212> TYPE: DNA
<213> ORGANISM: Artificial Sequence
<220> FEATURE:
<223> OTHER INFORMATION: Synthetic sequence

<400> SEQUENCE: 29
cgttccaggg tccacaaagt c                                                      21

<210> SEQ ID NO 30
<211> LENGTH: 25
<212> TYPE: RNA
<213> ORGANISM: Artificial Sequence
<220> FEATURE:
<223> OTHER INFORMATION: Synthetic sequence

<400> SEQUENCE: 30
cccugcugug augaauuaca gcauu                                                  25

<210> SEQ ID NO 31
<211> LENGTH: 25
<212> TYPE: RNA
<213> ORGANISM: Artificial Sequence
<220> FEATURE:
<223> OTHER INFORMATION: Synthetic sequence

<400> SEQUENCE: 31
ccuuuagugg uccaucgcca guuau                                                  25

<210> SEQ ID NO 32
<211> LENGTH: 19
<212> TYPE: RNA
<213> ORGANISM: Artificial Sequence
<220> FEATURE:
<223> OTHER INFORMATION: Synthetic sequence
<220> FEATURE:
```

```
<221> NAME/KEY: misc_feature
<222> LOCATION: (19)..(19)
<223> OTHER INFORMATION: =Att

<400> SEQUENCE: 32
gggacuucaa cgaaggaca                                                                    19

<210> SEQ ID NO 33
<211> LENGTH: 9
<212> TYPE: PRT
<213> ORGANISM: Artificial Sequence
<220> FEATURE:
<223> OTHER INFORMATION: Synthetic sequence

<400> SEQUENCE: 33

Tyr Pro Tyr Asp Val Pro Asp Tyr Ala
1               5

<210> SEQ ID NO 34
<211> LENGTH: 19
<212> TYPE: DNA
<213> ORGANISM: Artificial Sequence
<220> FEATURE:
<223> OTHER INFORMATION: Synthetic sequence

<400> SEQUENCE: 34
tgctgggaat gctgtaatt                                                                    19

<210> SEQ ID NO 35
<211> LENGTH: 19
<212> TYPE: DNA
<213> ORGANISM: Artificial Sequence
<220> FEATURE:
<223> OTHER INFORMATION: Synthetic sequence

<400> SEQUENCE: 35
cagcgcagaa gtgagcatc                                                                    19

<210> SEQ ID NO 36
<211> LENGTH: 19
<212> TYPE: DNA
<213> ORGANISM: Artificial Sequence
<220> FEATURE:
<223> OTHER INFORMATION: Synthetic sequence

<400> SEQUENCE: 36
ggatattcat ggtggctgt                                                                    19

<210> SEQ ID NO 37
<211> LENGTH: 23
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (21)..(21)
<223> OTHER INFORMATION: n is a, c, g, or t

<400> SEQUENCE: 37
tcctcagcat cttatccgag ngg                                                               23

<210> SEQ ID NO 38
<211> LENGTH: 19
<212> TYPE: DNA
<213> ORGANISM: Artificial Sequence
<220> FEATURE:
```

<223> OTHER INFORMATION: Synthetic sequence

<400> SEQUENCE: 38
ccatgagcgc tgctcagat                                                   19

<210> SEQ ID NO 39
<211> LENGTH: 22
<212> TYPE: DNA
<213> ORGANISM: Artificial Sequence
<220> FEATURE:
<223> OTHER INFORMATION: Synthetic sequence

<400> SEQUENCE: 39
tcatggggtt atagggaggt ca                                               22

<210> SEQ ID NO 40
<211> LENGTH: 56
<212> TYPE: DNA
<213> ORGANISM: Artificial Sequence
<220> FEATURE:
<223> OTHER INFORMATION: Synthetic sequence

<400> SEQUENCE: 40
ctggcccctc ctcagcatct tatccgagtg gaaggaaatt tgcgtgtgga gtattt        56

<210> SEQ ID NO 41
<211> LENGTH: 55
<212> TYPE: DNA
<213> ORGANISM: Artificial Sequence
<220> FEATURE:
<223> OTHER INFORMATION: Synthetic sequence

<400> SEQUENCE: 41
ctggcccctc ctcagcatct tatcgagtgg aaggaaattt gcgtgtggag tattt         55

<210> SEQ ID NO 42
<211> LENGTH: 57
<212> TYPE: DNA
<213> ORGANISM: Artificial Sequence
<220> FEATURE:
<223> OTHER INFORMATION: Synthetic sequence

<400> SEQUENCE: 42
ctggcccctc ctcagcatct tatccagagt ggaaggaaat ttgcgtgtgg agtattt       57

EXPLOITING ESTROGEN RECEPTOR BETA AND TP53 INTERACTION AS A NEW THERAPEUTIC STRATEGY FOR CANCER

CROSS-REFERENCE TO RELATED APPLICATIONS

This application is a national stage (371) application of International Application No. PCT/US2019/060248, filed Nov. 7, 2019, which claims priority to and the benefit of U.S. provisional patent application Ser. No. 62/756,699, entitled Exploiting Estrogen Receptor Beta and TP53 Interaction as a New Therapeutic Strategy for Cancer, filed Nov. 7, 2018. Both applications are incorporated herein by reference in their entirety.

STATEMENT REGARDING FEDERALLY SPONSORED RESEARCH OR DEVELOPMENT

This invention was made with government support under R01CA079911 and P30CA016056 awarded by the National Institutes of Health. The government has certain rights in the invention.

TECHNICAL FIELD

The present invention is directed to the field of personalized medicine. In particular, the present invention is directed to methods and therapeutic agents suitable for treating a subject having cancer, where the cancer is characterized by expression of estrogen receptor β (also referred to herein as "estrogen receptor beta," "estrogen receptor-beta," "ERβ" or "ESR2") and mutant tumor protein 53 (TP53) or expression of ERβ and wildtype TP53.

BACKGROUND

Triple negative breast cancers ("TNBC"), most of which are composed of a basal-like BC molecular subtype, do not express estrogen receptor-alpha (ERα), progesterone receptor (PR), or human epidermal growth factor 2 (HER-2) receptor. Therefore, currently available targeted therapies for breast cancers (BC) are not effective against these very aggressive tumors. This, coupled with the long-term ineffectiveness of cytotoxic chemotherapy, makes it urgent to discover new therapeutic targets and strategies to treat TNBC.

SUMMARY

A first aspect of the present invention is directed to a method for inducing cancer cell death. This method comprises selecting a population of cancer cells expressing estrogen-receptor β (ERβ) and mutant tumor protein 53 (TP53), and administering, to the population of cancer cells, an agent that increases ERβ protein expression in an amount effective to induce cancer cell death in the population of cancer cells.

Another aspect of the present invention is directed to a method for treating a subject having cancer. This method comprises selecting a subject having a cancer that is characterized by cancer cells expressing estrogen-receptor β (ERβ) and mutant tumor protein 53 (TP53), and administering, to the selected subject, an agent that increases ERβ protein expression in an amount effective to induce cell death in the cancer cells of the subject, thereby treating the subject having cancer.

Another aspect of the present invention is directed to a method for increasing estrogen receptor β (ERβ) expression levels in a subject in need thereof. This method comprises selecting a subject having low ERβ levels, and administering, to the subject, tamoxifen in an amount effective to increase ERβ protein levels in the subject.

Another aspect of the present invention is directed to a method for treating a subject having cancer. This method comprises selecting a subject having a cancer characterized by cancer cells expressing estrogen-receptor β (ERβ) and wildtype tumor protein 53 (TP53), and administering, to the subject, an agent that inhibits ERβ and TP53 binding interaction in an amount effective to induce cell death in the cancer cells of the subject, thereby treating the subject having cancer.

Another aspect of the present invention is directed to a method that comprises obtaining a cancer sample from a subject, and detecting, in the sample, the presence of estrogen-receptor β (ERβ) protein expression and tumor protein 53 (TP53) protein expression. In one embodiment, the TP53 is a mutant TP53. In another embodiment, the TP53 is wildtype TP53.

BRIEF DESCRIPTION OF THE DRAWINGS

Embodiments are described herein with reference to the accompanying drawings, in which similar reference characters denote similar elements throughout the several views. It is to be understood that in some instances, various aspects of the embodiments may be shown exaggerated, enlarged, exploded, or incomplete to facilitate an understanding of the invention.

FIGS. 1A-M. Interaction of ESR2 (also referred to herein as estrogen receptor beta or ERR) with both wildtype (WT) and mutant TP53 (tumor protein 53). A-F): ESR2-TP53 interaction was analyzed by PLA in (A) MCF-7 cells, (B) ZR-75-1, (C) CAL-51 (Cell lines expressing endogenous WT TP53), (D) MDA-MB-231, (E) MDA-MB-468, and (F) SK-BR-3 (cells expressing endogenous mutant TP53). Cells were transfected with either control (si-NS) (left panels) or si-ESR2 (right panels) for 48 hours. Interaction assayed by PLA is noted in white font (inset). Scale bar for FIG. 1A and D=20 μm; Scale bar for FIGS. 1B, C, E, and F=10 μm. G-K): Co-IP of endogenous ESR2 and WT TP53 was performed in G) MDA-MB-468 and in H) MCF-7, followed by immunoblotting with TP53 and ESR2 antibodies; I) Co-IP of endogenous TP53 and exogenously expressed FLAG-ESR2 was performed in MCF-7 cells, followed by immunoblotting with TP53 and FLAG antibodies; J) Co-IP of endogenous ESR2 and WT TP53 in MDA-MB-231 cells was performed, followed by immunoblotting with TP53 and ESR2 antibodies; K) Co-IP of endogenous TP53 and exogenously expressed FLAG-ESR2 in MDA-MB-231 cells was performed with TP53 antibody, followed by immunoblotting with TP53 and FLAG antibodies. L) Schematic diagram of wild type and truncated mutant ESR2 proteins and their ability to bind with TP53 in a GST pulldown assay. (See also FIGS. 11A-C). TA=Transactivation domain; DBD=DNA binding domain; TD=Tetramerization domain; REG=Regulatory domain; *=point mutation; −=no binding; +=strong binding; Numbers=position of amino acid residues. M) Schematic diagram of wild type and truncated mutant TP53 proteins and their ability to bind with ESR2 in a GST pull-down assay. (See also FIGS. 11D-E). A/B=Activation function 1 (AF1); C=DNA binding domain (DBD); D=Hinge region; E/F=Activation function 2 (AF2)/Ligand binding domain (LBD). PLA=proximity ligation assay; si-NS=non-specific siRNA; si-ESR2=ESR2-specific siRNA. Co-IP=Co-immunoprecipitation.

FIGS. 2A-J. Functional effect of ESR2 on wildtype (WT) TP53. A) TP53-target gene expression in MCF-7 cells with or without knocking down ESR2. Transcripts in MCF-7 cells treated with si-NS or ESR2 #1 siRNA for 48 hours were measured by qRT-PCR. Inset: RT-PCR analysis of ESR2 mRNA was performed to monitor ESR2 knockdown after 48 hours. B) TP53-target gene expression in MCF-7ESR2shRNA stable cells treated with or without 1 µg/ml doxycycline for 48 hours to induce ESR2 shRNA expression was determined by qRT-PCR. C) qChIP for TP53 on CDKN1A and BBC3 promoters was performed in MCF-7 cells with or without ESR2 knockdown with siRNA #1 for 48 hours. D) Expression of ESR2, CDKN1A, and BBC3 proteins in MCF-7ESR2shRNA cells treated with or without 1 µg/ml doxycycline for 48 hours was analyzed by immunoblotting. E) qChIP was performed for TP53 at CDKN1A and BBC3 promoters in MCF-7 cells 48 hours post-transfection with vector or FLAG-ESR2 cDNA. F) ESR2, TP53, CDKN1A, and BBC3 protein expression in MCF-7 cells with or without FLAG-ESR2 transfection for 48 hours was analyzed by immunoblotting. G) TP53-target gene expression in ZR-75-1 cells with or without knocking down ESR2 with siRNA for 48 hours was determined by qRT-PCR. H) Expression of ESR2, CDKN1A, and BBC3 proteins in ZR-75-1 cells 48 hours post-transfection with ESR2 siRNA was analyzed by immunoblotting. I) TP53-target gene expression in ZR-75-1 cells 48 hours post-transfection with vector or FLAG-ESR2 was determined by qRT-PCR. J) Expression of ESR2, CDKN1A, and BBC3 proteins in ZR-75-1 cells 48 hours post-transfection with vector or FLAG-ESR2 was analyzed by immunoblotting. All 'p' values were determined by two-tailed Student's t-test. Error bars represent standard deviation (SD). si-NS: non-specific siRNA. RT-PCR=semi-quantitative reverse transcript PCR; qRT-PCR=quantitative real time PCR; qChIP=quantitative chromatin immunoprecipitation.

FIGS. 6A-J. Effect of Sequestration of Mutant TP53 by ESR2 on Mutant TP53-TP73 Complex and TP73 Activation. A) Schematic diagram comparing domains of TP53 and TP73, showing the N-terminal transactivation domain (TAD), DNA binding domain (DBD) oligomerization domain (OD) and sterile alpha motif (SAM) domain. Proteins are not aligned proportionately to the length of each domain. Numbers correspond to the amino acid residues that mark different domains. Note that the C-terminus of TP53 domain (aa 361-393) that binds to ESR2 is not conserved in TP73. B) PLA for TP53-TP73 interaction was performed in MDA-MB-231 cells with or without knocking down ESR2 with si-ESR2 #1 for 48 hours. Scale bar=20 μm. C) Co-IP of TP73 and TP53 was performed with MDA-MB-231 cells following ESR2 knockdown with si-ESR2 #1 for 48 hours. D) qChIP for TP73 on CDKN1A and BBC3 gene promoters was performed in MDA-MB-231 cells following ESR2 knockdown with si-ESR2 #1 for 48 hours. E) Endogenous TP73 mRNA in MDA-MB-231 cells transfected with or without TP73 siRNA for 48 hours was analyzed by qRT-PCR. Bottom panel: TP73 protein levels in the cell lysates was analyzed by immunoblotting. F) TP53-target gene expression in MDA-MB-231 cells transfected with or without TP73 siRNA for 48 hours was determined by qRT-PCR. G) PLA for interaction between mutant TP53 and TP73 was performed in MDA-MB-468 cells with or without knocking down ESR2 with si-ESR2 #2 for 48 hours. Scale bar=5 μm. H) TP53-target gene expression in MDA-MB-468 cells transfected with and without TP73 siRNA for 48 hours was determined by qRT-PCR. I) PLA for interaction between mutant TP53 and TP73 was performed in SK-BR-3 cells with or without knocking down ESR2 with si-ESR2 #2 for 48 hours. Scale bar=5 μm. J) A model for the anti-tumorigenic role of ESR2 in the mutant TP53 context is shown. Showing two prototypic TP53-targets, p21 and PUMA, does not imply these are the only proteins participating in the ESR2-TP53 signaling crosstalk. All 'p' values were determined by two-tailed Student's t-test. Error bars represent standard deviation (SD). siESR2=ESR2-specific siRNA; PLA=proximity ligation assay; qRT-PCR=quantitative real time PCR; Co-IP=Co-immunoprecipitation; qChIP=quantitative immunoprecipitation; IB=immunoblot.

FIGS. 7A-J. Effect of Tamoxifen on ESR2-mutant TP53 Interaction and TP73 Activity. A) PLA for interaction between ESR2 and mutant TP53 was performed in MDA-MB-231 cells following treatment with 5 μM TAM. Scale bar=20 μm. B) PLA for interaction between mutant TP53 and TP73 was performed in MDA-MB-231 cells following treatment with 5 μM TAM. Scale bar=20 μm. C) PLA for interaction between ESR2 and mutant TP53 was performed in MDA-MB-468 following treatment with 5 μM TAM. Scale bar=5 μM. D) PLA for interaction between ESR2 and mutant TP53 in SK-BR-3 cells following treatment with 5

μM TAM. Scale bar=10 μM. E) Expression of ESR2 and TP53 in MDA-MB-231 cells following treatment with 5 μM 4-OH tamoxifen was analyzed by immunoblotting. F) TP53-target gene expression in MDA-MB-231 with or without ESR2 knockdown (with siESR2 #1) for 48 hours and with or without treatment with 5 μM 4-OH tamoxifen for 24 hours was determined by qRT-PCR. G) TP53 target gene expression in MDA-MB-231 with or without TP73 knockdown for 48 hours and with or without treatment with 5 μM 4-OH tamoxifen for 24 hours was determined by qRT-PCR. H) Expression of ESR2 and TP53 proteins in MDA-MB-468 cells following treatment with 5 μM 4-hydroxytamoxifen was analyzed by immunoblotting. I) TP53-target gene expression in MDA-MB-468 with or without ESR2 knockdown for 48 hours and with or without treatment with 5 μM 4-OH tamoxifen for 24 hours was determined by qRT-PCR. J) TP53-target gene expression in MDA-MB-231 with or without TP73 knockdown for 48 hours and with or without treatment with 5 μM 4-OH tamoxifen for 24 hours was determined by qRT-PCR. All 'p' values were determined by two-tailed Student's t-test. Error bars represent standard deviation (SD). siESR2=ESR2-specific siRNA; PLA=proximity ligation assay; qRT-PCR=quantitative real time PCR.

Figure 8A:
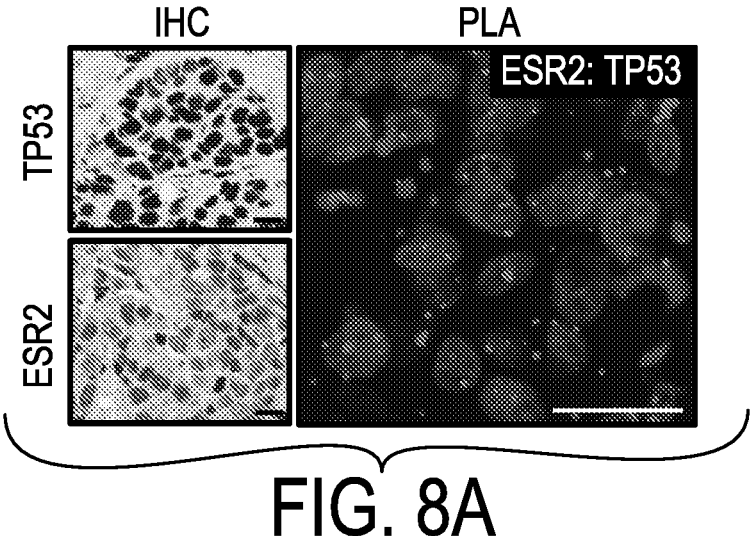
Figure 8B:
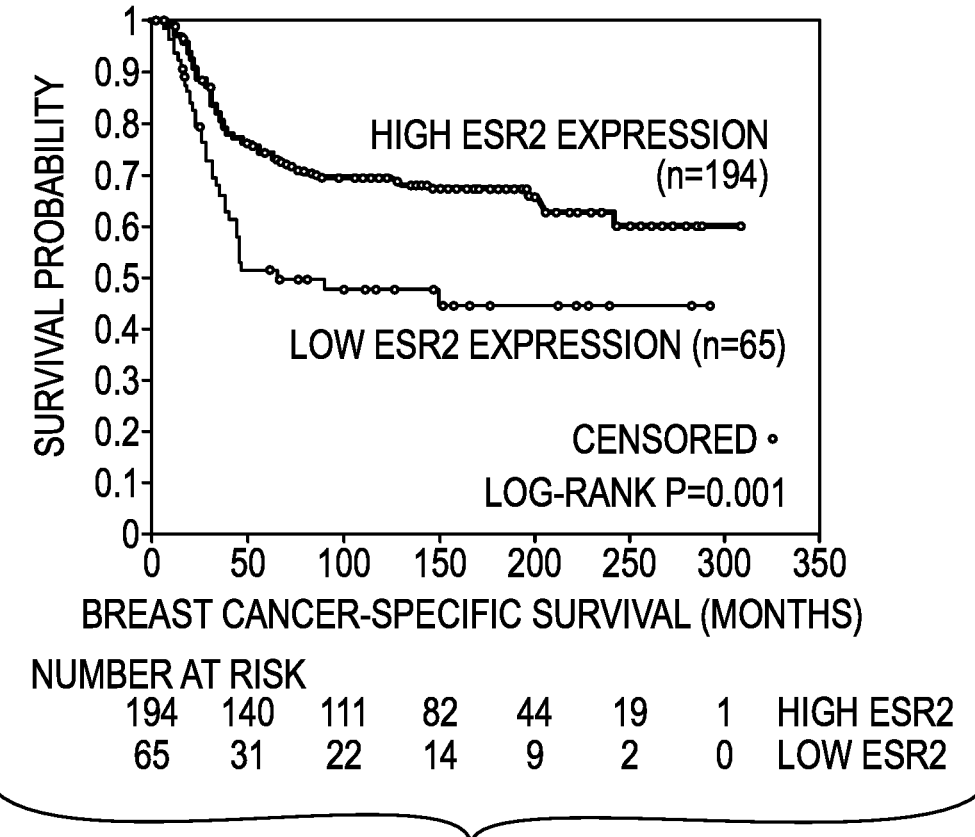
Figure 8C:
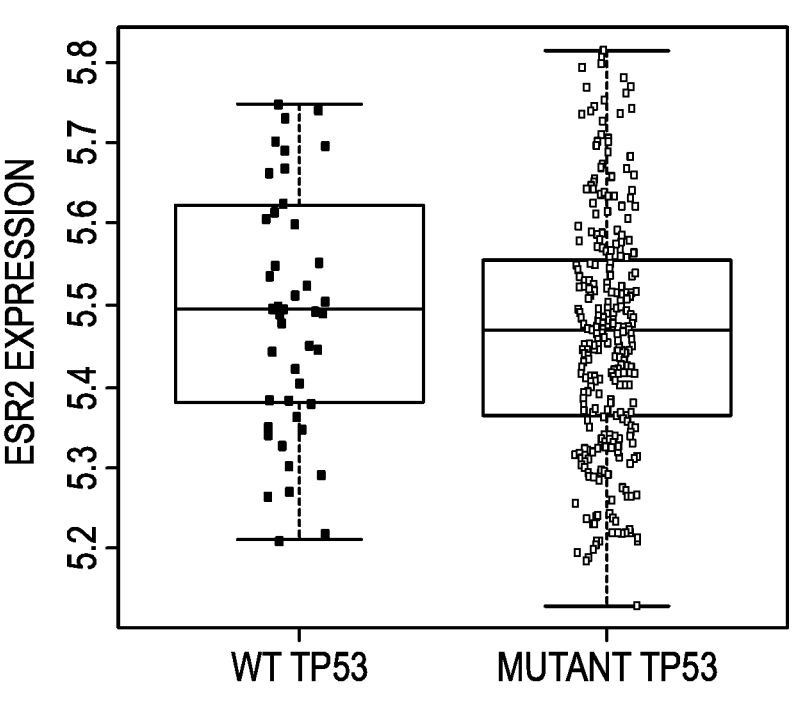

FIGS. 8A-C. Impact of TP53 Status on the Prognostic Role of ESR2 in Patients with Basal-like/TNBC Tumors. A) Images of IHC staining for TP53 and ESR2 (left panels) and PLA for ESR2-TP53 interaction (right panels) in representative TNBC patient tumors are shown. Scale bar=20 μm. B) Kaplan-Meier survival curves for BC Specific Survival (BCSS) in patients with mutant TP53, Basal-like breast tumors of the METABRIC cohort, stratified into high ESR2 expression (expression above 25$^{th}$ percentile) and low ESR2 expression (below 25$^{th}$ percentile) are shown. Number of patients at risk at each time-point is listed below the x-axis. BCSS: p=0.001 by log-rank test, comparing bottom 25% of ESR2 expression versus other cases. C) Distribution of ESR2 expression in Basal-like breast tumors of the METABRIC cohort stratified by TP53 mutation status is shown. Kruskal-Wallis test was used for the analysis. There was no considerable difference in ESR2 expression in WT TP53 versus mutant TP53 groups. Error bars represent standard deviation. METABRIC=Molecular Taxonomy of Breast Cancer International Consortium.

Figure 9A:
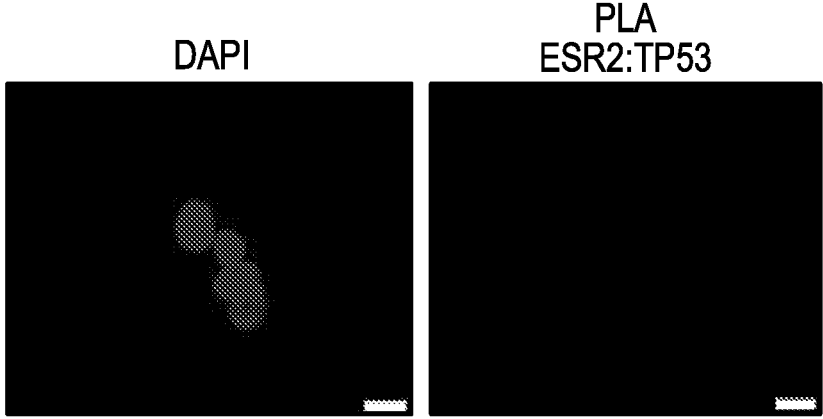
Figure 9A:
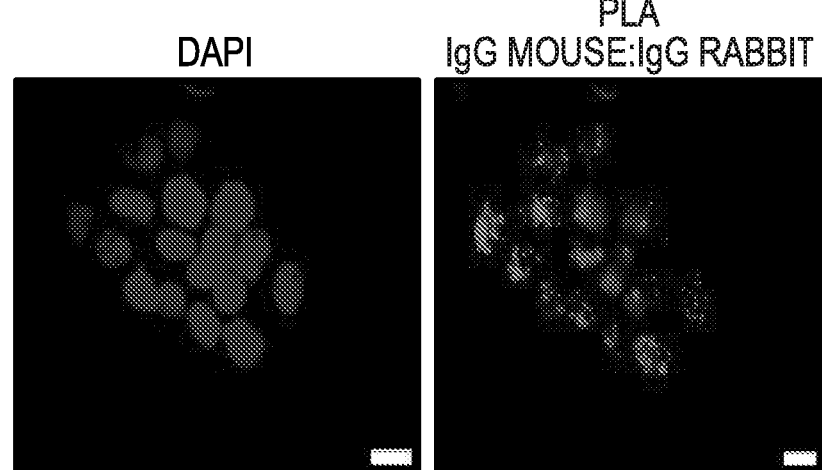
Figure 9B:
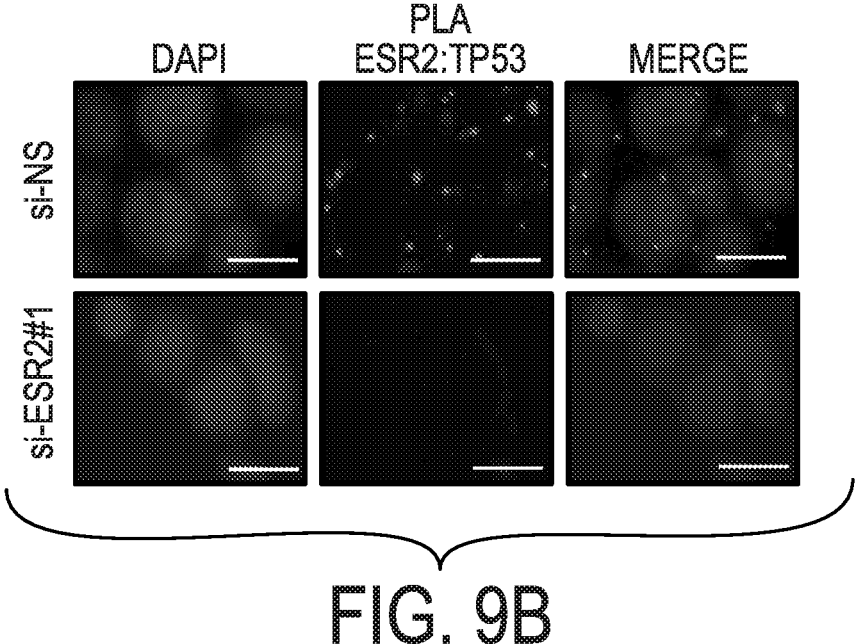
Figure 9C:
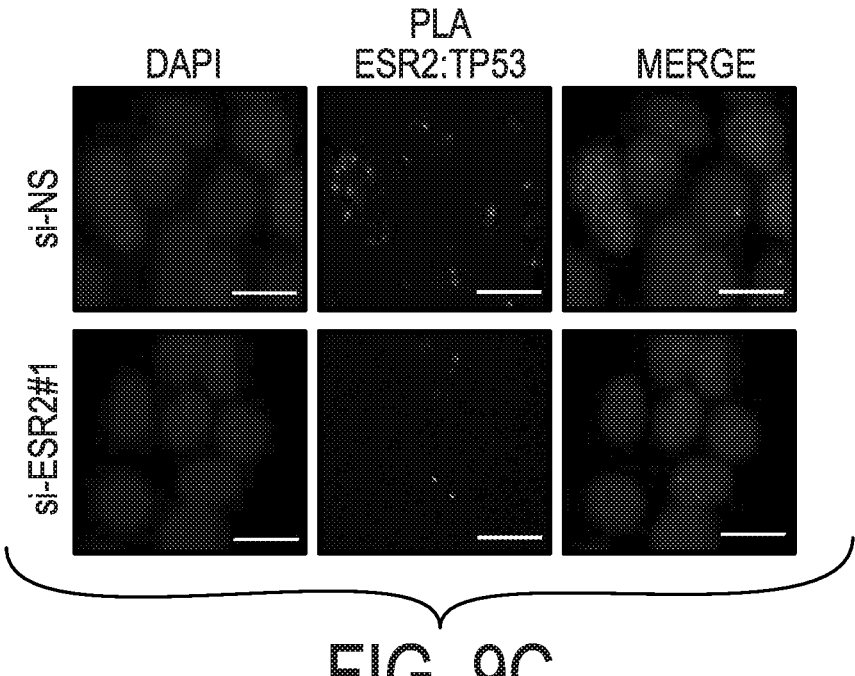

FIGS. 9A-C. Additional PLA analyses of ESR2-TP53 interaction. (A) Top panel: PLA for interaction between endogenous ESR2 and mutant TP53 was performed in T-47D cells. Antibodies against ESR2 (clone 14C8, GeneTex) and TP53 (FL-393, Santa Cruz Biotechnology) were used. Bottom panel: Negative control for PLA in T-47D cells with mouse IgG and rabbit IgG are shown. (B-C) MCF-7 cells were transfected with either si-NS or si-ESR2 #1 and were processed for PLA with (B) Anti-ESR2 mouse antibody (clone 14C8, GeneTex) and anti-TP53 rabbit antibody (FL393, Santa Cruz Biotechnology) as primary antibodies, and (C) with additional antibodies anti-ESR2 rabbit (H-150, Santa Cruz) and anti-TP53 mouse (D0-1, Santa Cruz) to further validate the specificity of the PLA signal. si-NS=non-specific siRNA; si-ESR2 #1=ESR2-specific siRNA #1; PLA=Proximity Ligation Assay. Scale bars (A)=10 μm; Scale bars (B & C)=20 μm.

Figures 10A, 10B, 10C:
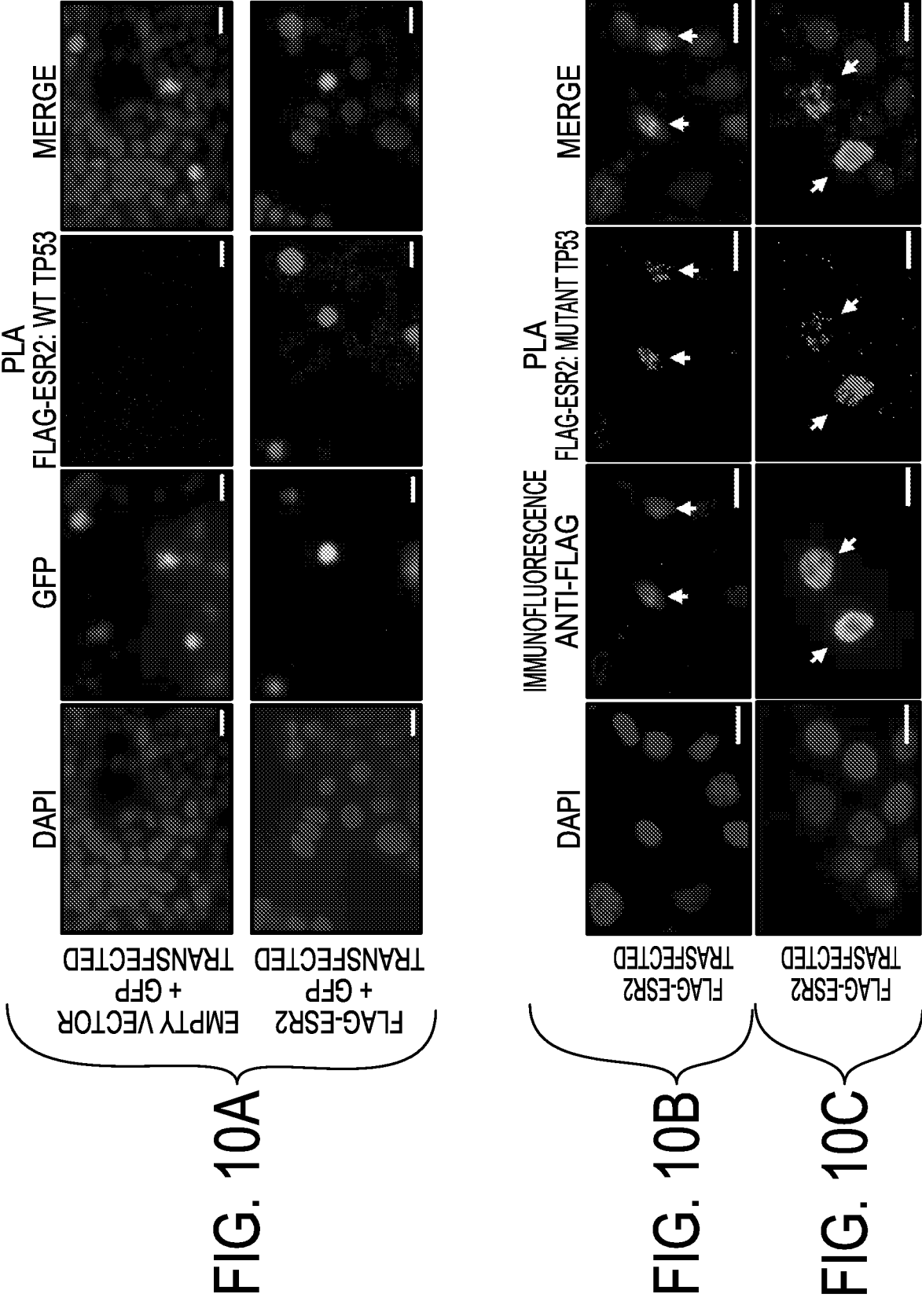

FIGS. 10A-C. Analysis of interaction between endogenous wildtype and mutant TP53 and exogenously overexpressed FLAG-ESR2-overexpressing cells. (A) PLA for interaction between ESR2 and WT TP53 was performed in MCF7 cells. Cells were transfected with 1 μg of empty vector or Flag-ESR2 plasmid DNA along with 0.1 μg of a green fluorescent protein (GFP) expression construct (pBabe-eGFP). At 24 hours post-transfection cells were trypsinized and counted and were re-plated. At 48 hours post-transfection cells were fixed, permeabilized and subjected to in situ PLA. DAPI was used as a nuclear stain. (B) In situ PLA for ESR2-TP53 interactions in MDA-MB-231 cells transfected with 1 µg of empty vector or FLAG-ESR2 plasmid DNA. At 24 hours post-transfection cells were trypsinized and counted and were re-plated. At 48 hours post-transfection cells were fixed, permeabilized and subjected to in situ PLA with anti-FLAG and anti-TP53 antibodies (Anti-FLAG$^{M}$+anti-TP53$^{R}$). An additional staining for ESR2 (using mouse anti-FLAG-Alexa$^{488}$) was incorporated during the amplification stage of PLA to delineate transfected from un-transfected cells. Both immunofluorescence and PLA signals are indicated by white arrows. DAPI was used as a nuclear stain. (C) Similar experiment as (A) in SK-BR-3 cells. WT=Wild type; PLA=Proximity Ligation Assay; M=mouse and, R=rabbit, Scale bar=20 µm.

FIGS. 11A-E. Mapping of interaction domains in ERβ and TP53. (A-B) In vitro interaction and mapping of domains of ESR2 that interact with TP53. (A) Schematic diagram of the full length ESR2 protein containing 530 amino acids is shown (top panel). GST or GST-TP53 proteins expressed in *E. coli.* were bound to glutathione-sepharose beads and allowed to interact with in vitro translated $^{35}$S-labeled ESR2 wild type (WT) or various mutant proteins synthesized by a TNT kit. The bound complexes were subjected to SDS-PAGE, followed by fluorography. Input lane represents 5% of total radiolabeled protein used in the pull-down. The expression of each in vitro translated protein (IVT) as analyzed by SDS-PAGE and autoradiography is shown in the bottom panel. (B) Bacterially expressed and immobilized GST-ESR2 (149-214aa; C domain) and (149-248aa; C & D domains) were incubated with full-length $^{35}$S-labeled TP53 and subjected to GST-pull down. Coomassie stained GST-ESR2 proteins are shown in the lower panel. (C) Schematic representation of domains in ESR2 required for interaction with TP53. (D-E) Mapping of domain of TP53 required for ESR2 interaction. (D) Schematic diagram of the full-length TP53 consisting of 393 amino acids is shown at the top. GST-WT TP53 and different GST-TP53 mutants, GST-TP53 (1-160), (160-395), (160-318), (319-393), (teramerization mutant), (Δ325-356), (Δ361-393), and (361-393) were expressed in bacteria and bound to glutathione-sepharose beads as described. These GST-tagged proteins were allowed to interact with in vitro translated $^{35}$S-labeled ESR2 wild type or various mutant proteins synthesized by a TNT kit. The bound complexes were subjected to SDS-PAGE, followed by fluorography. Bottom panels show GST-TP53 fusion proteins expression as monitored by SDS-PAGE followed by staining with Coomassie blue. (E) Schematic representation of domains in TP53 required for interaction with ESR2. GST=Glutathione S-Transferase; TA=Transactivation domain; DBD=DNA binding domain; TD=Tetramerization domain; REG=Regulatory domain; *point mutation; −=no binding; +=strong binding. Numbers on the top of rectangular schematic representation of ESR2 and TP53 proteins indicate amino acid residues.

FIGS. 12A-E. Analysis of ESR2/ESR2 RNA and protein expression in multiple breast cancer cell lines. (A) Expression of endogenous ESR2 protein. MCF-7, ZR-75-1, CAL-51, MCF-10A,T-47D, CAMA-1, MDA-MB-231, SK-BR-3, BC3-WT TP53 and BC3-shTP53 cells were harvested and lysed in Radioimmunoprecipitation assay (RIPA) buffer. ESR2 protein expression was analyzed by SDS-PAGEimmunoblotting. (B) Expression of Exogenous ESR2: Upper panel: MCF-7, ZR-75-1, MDA-MB-231, and BC3-WT TP53 cells were co-transfected with either empty vector or FLAG-ESR2 plasmid for 48 hrs. After 48 hours, cells were harvested and lysed in RIPA buffer for protein and Trizol (Invitrogen) reagent for mRNA. ESR2 mRNA was quantified by real time qRT-PCR using FastStart Universal SYBER Green mastermix (Roche) in Applied Biosystem's ABI Prism 7300 Real time PCR machine. Lower panel: Protein expression measured by immunoblotting of cell lysates corresponding to the RNA samples in the upper panel. (C) Knocking down of endogenous ESR2/ESR2: Upper panel: Knockdown of ESR2 with si-ESR2 #2 in MCF7, ZR-75-1, MDA-MB-231, and BC3-WT TP53 cells was quantified by Real time PCR. Cells were harvested and lysed in RIPA buffer for protein and Trizol reagent for mRNA. ESR2 mRNA was quantified by qRT-PCR using FastStart Universal SYBER Green mastermix (Roche) in Applied Biosystem's ABI Prism 7300 Real time PCR machine. Lower panel: Protein expression was measured by immunoblotting of cell lysates corresponding to the RNA samples in the upper panel. (D) Average Ct Value of ESR2 mRNA in breast cancer cells with and without knockdown and with and without overexpression are shown. (E) Expression of ESR2 protein in MCF7 and MDA-MB-231 cells where ESR2 was knocked down with si-ESR2 #1 or with doxycycline-inducible ESR2 shRNA was analyzed by immunoblotting. Error bars are represented as mean (SD) and p values are as per the two tailed Student's t-test. si-NS=non-specific siRNA; si-ESR2 #1&2=ESR2-specific siRNAs. qRT-PCR=Quantitative real time polymerase chain reaction, Ct=Cycle Threshold.

FIGS. 13A-E. Effect of ESR2 on proliferation of MCF-7 (luminal breast cancer cell line with WT TP53) and T47D (luminal breast cancer cells with mutant TP53), and in MDA-MB-231 (TNBC cell line with mutant TP53). (A) qChIP was performed for promoter occupancy of CDKN1A by TP53 in MCF-7 cells stably transfected with empty vector (control) or HA-ESR2. 1 µg of total RNA was reverse-transcribed and $1110^{th}$-$1120^{th}$ of which was PCR-amplified for 25-30 cycles. Right panel: Expression of HA-ESR2 protein in stably transfected MCF-7 cells was analyzed by IB. (B) T-47D cells were co-transfected with either empty vector or FLAG-ESR2 plasmid for 48 hrs. After 48 hours, cells were harvested and lysed in RIPA buffer for protein and Trizol (Invitrogen) reagent for mRNA. Left panel: TP53-target gene expression in T-47D cells following ESR2 overexpression for 48 hours was determined by qRT-PCR. Right panel: Expression of ESR2, CDKN1A, and BBC3 proteins in T-47D cells following ESR2 overexpression for 48 hours was analyzed by IB. (C) Expression of ESR2 and CDKN1A (Left panel) and pro-apoptotic proteins (right panel) in MDA-MB-231 ESR2shRNA stable cells with or without 1 µg/ml doxycycline treatment for 48 hours to induce ESR2 shRNA was analyzed by IB. (D) Left panel: TP53-target gene expression in MDA-MB-231 cells with or without FLAG-ESR2 transfection for 48 hours was determined by qRT-PCR. Middle panel: Expression of ESR2, CDKN1A, and BBC3 in MDA-MB-231 cells with or without FLAG-ESR2 transfection for 48 hours was analyzed by IB. Right panel: Expression of markers of active apoptosis: cleaved BID, cleaved BCL2L11, BAX, and cleaved PARP1 proteins in MDA-MB-231 cells 48 hours post-FLAG-ESR2 transfection was analyzed by IB. (E) MDA-MB-231 cells were transfected with vector or FLAG-ESR2 for 48 hours. 48 hours of post-transfection cells were double-stained with Annexin V-FITC and Propidium Iodide for apoptosis assay by flow cytometry analysis. Bar graph (far right panel) shows fold change of Annexin+/PI-cells. Error bars are represented as mean (SD) and p values are as per the two tailed Student's t-test. qRT-PCR=Quantitative real time polymerase chain reaction; IB=Immunoblotting: Cl. BCL2L11=Cleaved BCL2L11; Cl. PARP1: Cleaved PARP1.

Figures 14A, 14B, 14C:
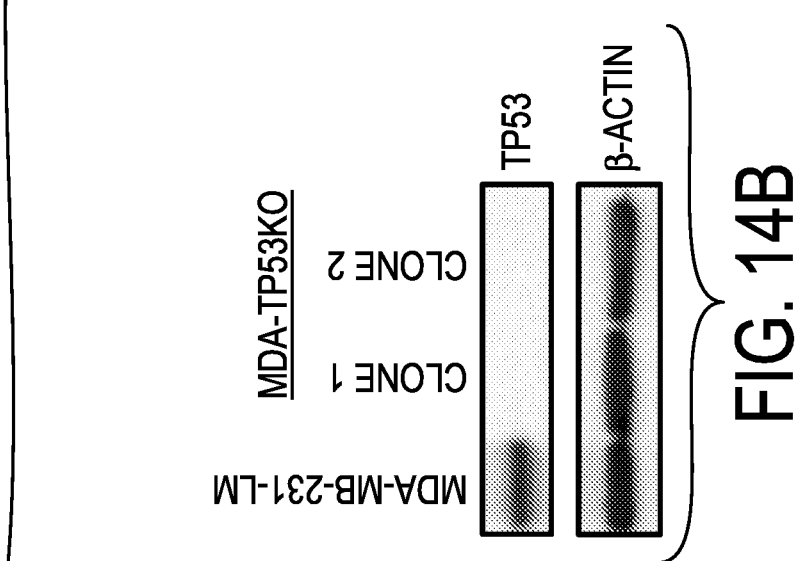

FIGS. 14A-C. CRISPR/Cas9 method to knockout of mutant TP53 in MDA-MB-231-LM-$4^{LUC+}$ cells. (A) Next generation/Massively parallel sequencing was performed to confirm the presence of indels. Mutations at single base pair deletion (−1 bp) in clone 1 and single base pair insertion (+1 bp) in clone 2 are shown in red shade. (B) Expression of TP53 protein in MDA-MB-231-LM-$4^{LUC+}$-TP53KO (also called MDA-MB-231-TP53KO) cells and in 2 CRISPR/Cas9 TP53 knockout clones was analyzed by IB. (C) MDA-MB-231-LM-$4^{LUC+}$-TP53KO cells transfected with and without combination of WT TP53 and knockdown of ESR2 with si-ESR2 RNA #2 for 48 hours. After 48 hours transfection, expression of ESR2 and TP53 proteins was analyzed by IB. si-NS=non-specific siRNA; si-ESR2 #2=ESR2 specific siRNA; IB=Immunoblotting.

Figures 15A, 15B:
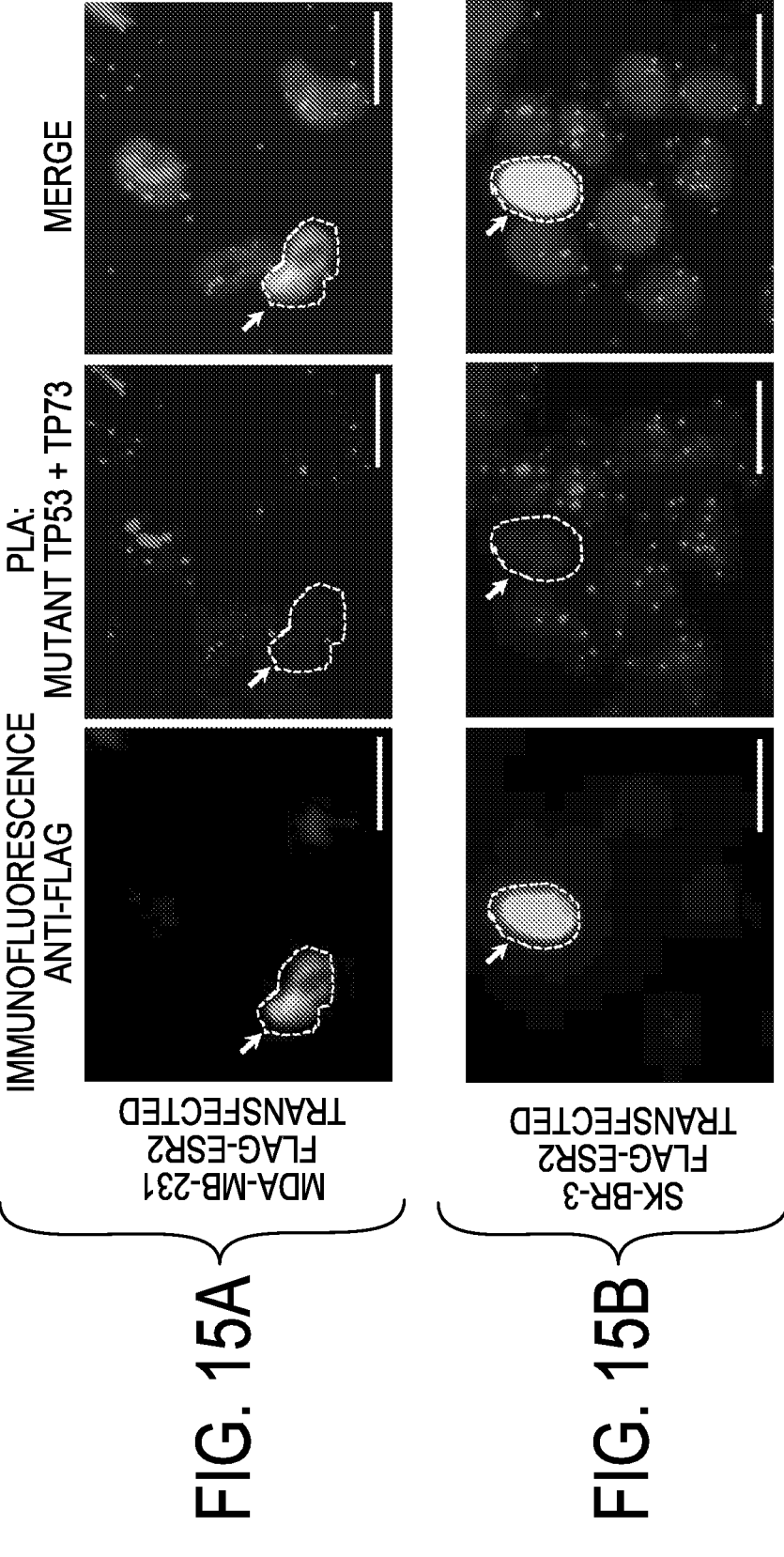

FIGS. 15A-B. Effect of overexpression of ESR2 on mutant TP53-TP73 interaction. MDA-MB-231 cells (A) and SKBR-3 cells (B) were transfected with FLAG-ESR2 were subjected to PLA using a mouse anti-TP53 antibody (DO-1) and a rabbit anti-TP73 antibody (H-79). An additional staining for ESR2 (using mouse anti-FLAG-Alexa$^{488}$) was incorporated during the amplification stage of PLA to delineate transfected from un-transfected cells. White dotted line delineates the boundary of ESR2 overexpressing cells (also indicated with white arrowhead). PLA=Proximity Ligation Assay. Scale bar=20 μm.

Figures 16A, 16B, 16C:
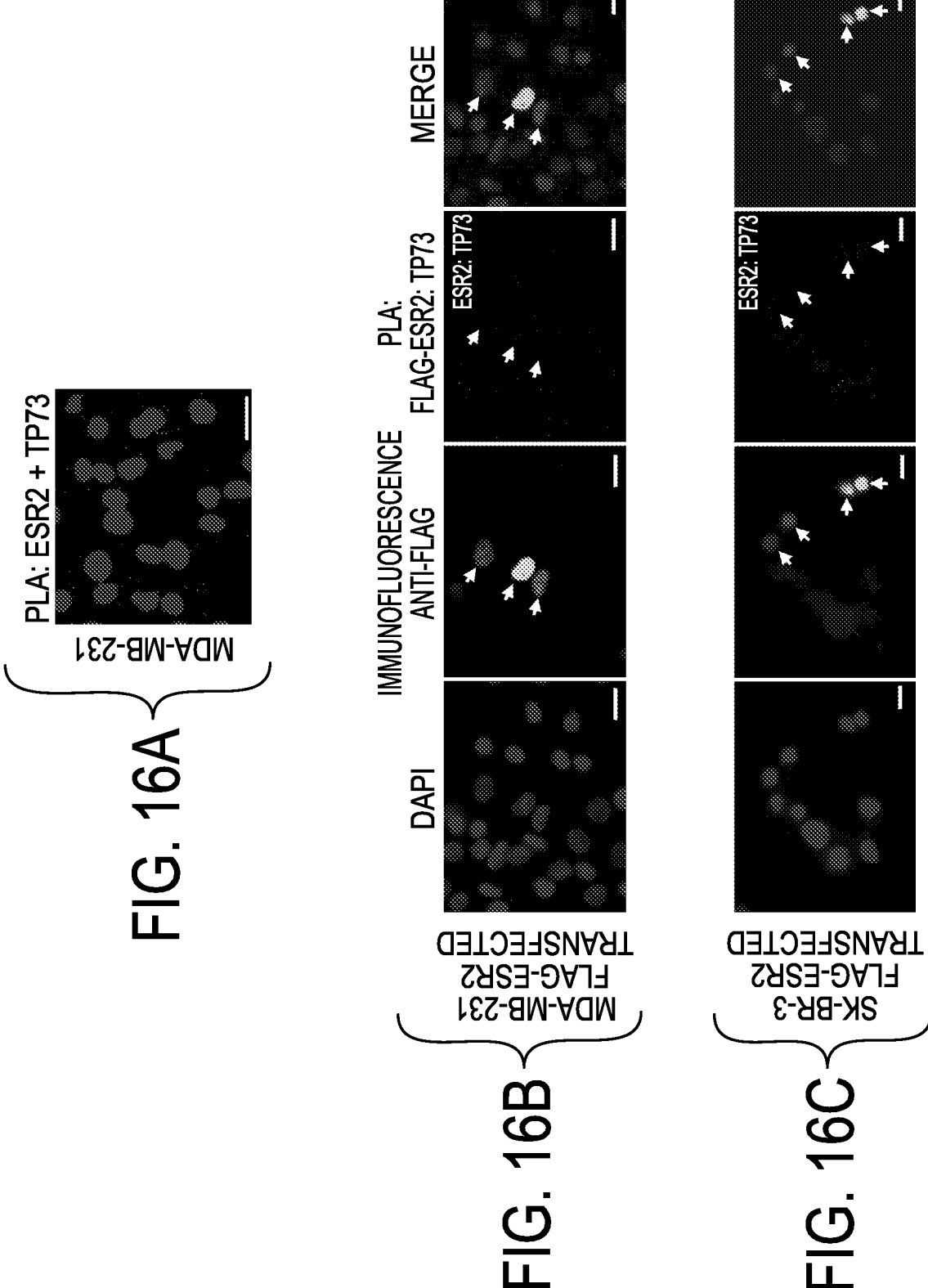

FIGS. 16A-C. Analysis of interaction between ESR2 and TP73 in MDA-B-231. (A) PLA for interactions between ESR2 and TP73 (antibodies: α-ESR2$^{M}$ & α-TP73$^{R}$). (B) PLA analysis (with anti-FLAG$^{M}$+anti-TP73$^{R}$) was performed to test interaction between exogenously over-expressed ESR2 and endogenous TP73 in MDA-MB-431. Mouse anti-Flag-Alexa$^{488}$ was used as an additional secondary fluorophore to monitor ESR2 expressing cells (white arrow heads). (C) Similar experiment as in (B) in SK-BR-3 cells. PLA=Proximity Ligation Assay; M=mouse and, R=rabbit. Scale bar=20 μm.

Figures 17A, 17B, 17C:
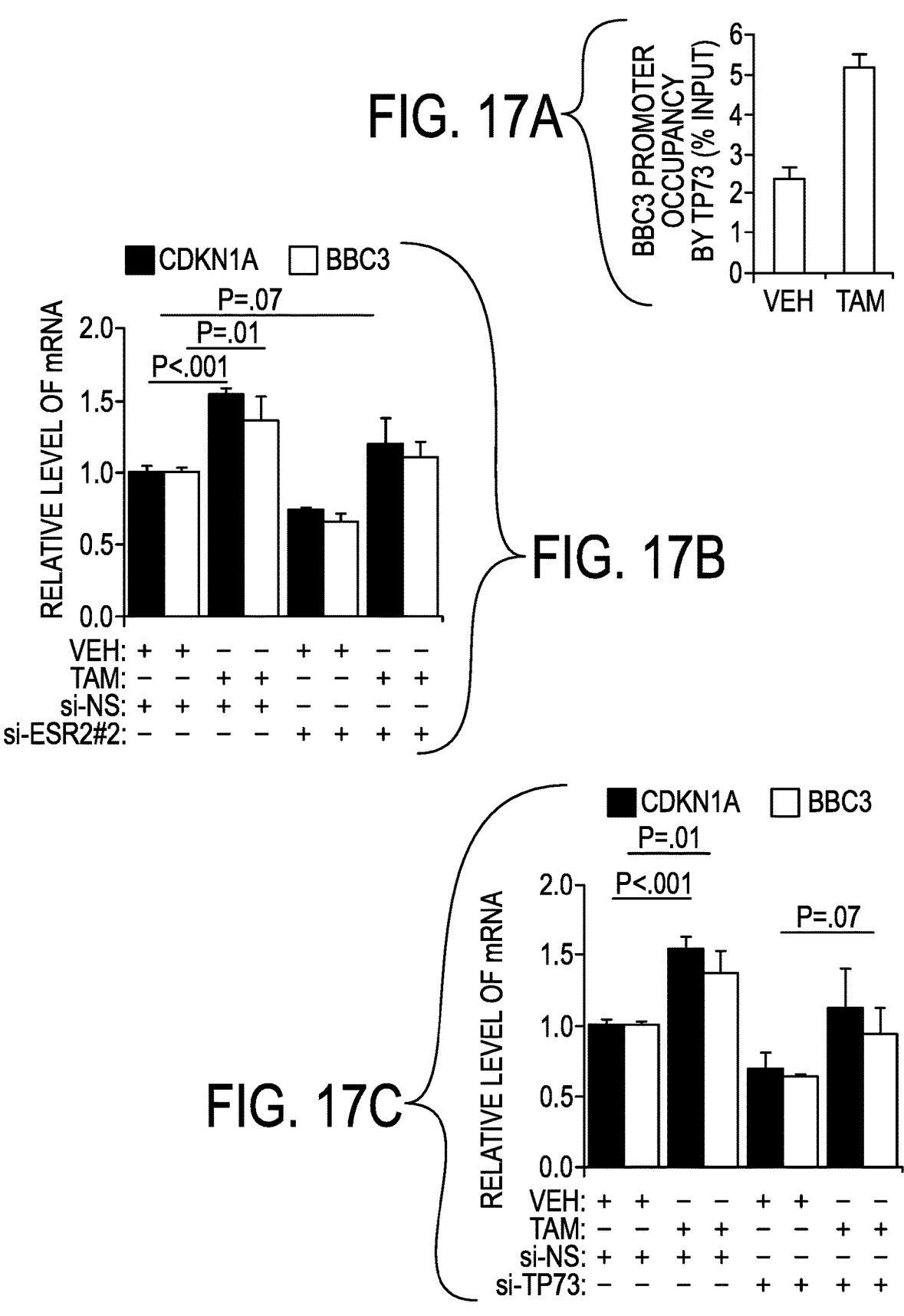

FIGS. 17A-C. Effect of ESR2 and TP73 on TNBC cells treated and not treated with tamoxifen. (A) Cells were treated with 5 μM TAM for 24 hours. After 24 hours, BBC3 promoter occupancy by TP73 was determined using qChIP in MDA-MB-231 cells. (B) SK-BR-3 cells were transfected with si-NS or si-ESR2 #2 for 48 hours and treated with or without 5 μM TAM for 24 hours. After 72 hours, expression of TP53 target genes (CDKN1A and BBC3) was determined using qRT-PCR. (C) SK-BR-3 cells were transfected with si-NS or si-TP73 for 48 hours and treated with or without 5 μM TAM for 24 hours. After 72 hours, expression of TP53 target genes (CDKN1A and BBC3) was determined using qRT-PCR. Error bars are represented as mean SD of three independent experiments. All 'p' values were determined by two tailed student t-test. qRT-PCR=Quantitative real time polymerase chain reaction. si-NS=non-specific siRNA; si-ESR2 #2=ESR2 specific siRNA; si-TP73=TP73 specific siRNA; VEH=Vehicle; TAM=4-Hydroxytamoxifen.

FIGS. 18A-G. Effect of TP53 status on the prognostic role of ESR2 (ERβ) in TNBC patient tumors. (A) Kaplan-Meier survival curves for Breast Cancer Specific Survival (BCSS) in patients with mutant TP53, Basal-like breast tumors of the METABRIC cohort, stratified into high, middle, and low ESR2 expression are shown. (B) Kaplan-Meier survival curves for BCSS in patients with WT TP53, Basal-like breast tumors of the METABRIC cohort, stratified into high ESR2 expression (expression above 25$^{th}$ percentile) and low ESR2 expression (below 25$^{th}$ percentile) are shown. (C) Kaplan-Meier survival curves for BCSS in patients with WT TP53, Basal-like breast tumors of the METABRIC cohort, stratified into high, middle, and low ESR2 expression are shown. (D) Boxplot representation of tumor size in TNBC patients with tumors of high TP53 IHC score (surrogate for mutant TP53) (n=23) stratified by ESR2 nuclear H score is shown. (E) Boxplot of tumor stage in TNBC patients with tumors of high TP53 IHC score (n=23) stratified by ESR2 nuclear H score is shown. (F) Kaplan-Meier plot of Progression-free Survival (PSF) of TNBC patients with tumors of low levels TP53 IHC score (surrogate for WT TP53) (n=23) stratified into ESR2 Low and ESR2 High protein levels (IHC score) in the Roswell patient cohort is shown. (G) Kaplan-Meier plot of Overall Survival of TNBC patients with tumors of low TP53 IHC score stratified into ESR2 Low and ESR2 High protein levels (IHC score) in the Roswell patient cohort is shown. METABRIC=Molecular Taxonomy of Breast Cancer International Consortium; IHC=Immunohistochemistry. All 'p' values are determined by Log Rank.

Figure 19A:
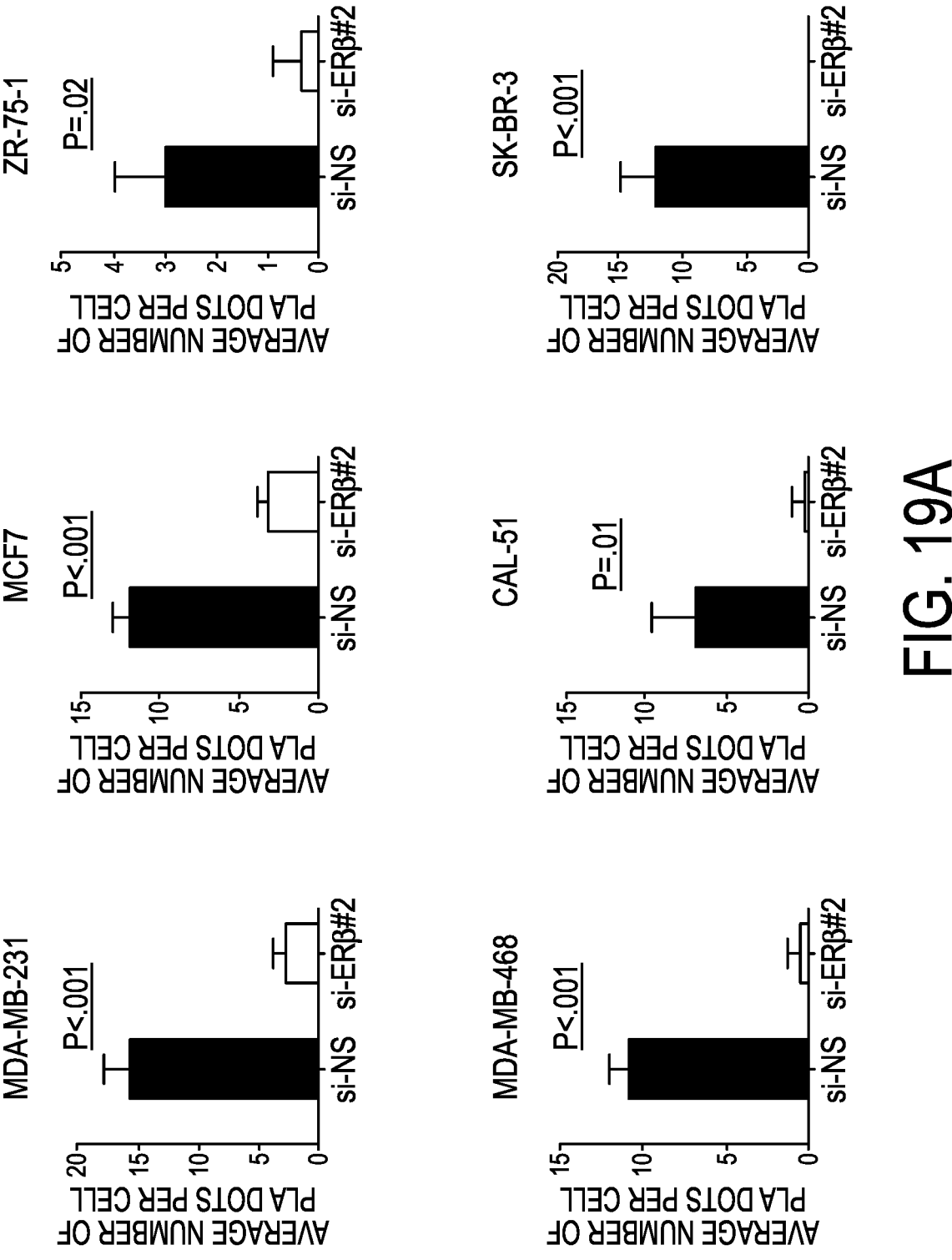
Figure 19B:
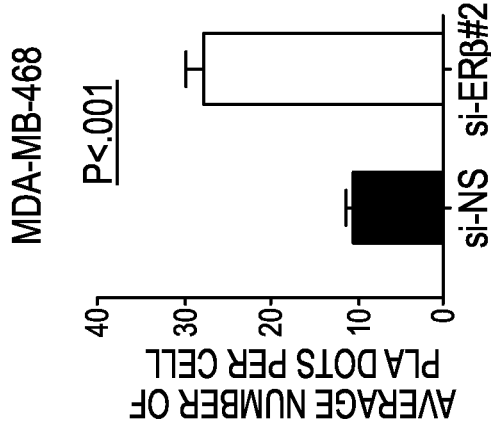
Figure 19B:
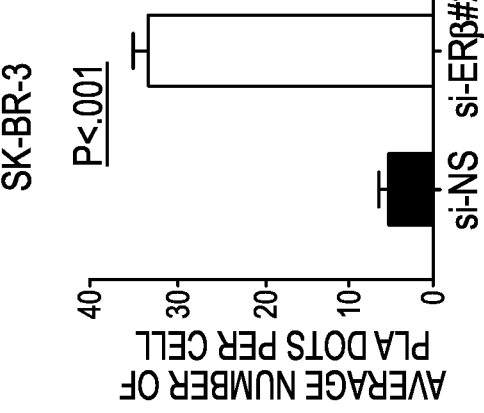
Figure 19B:
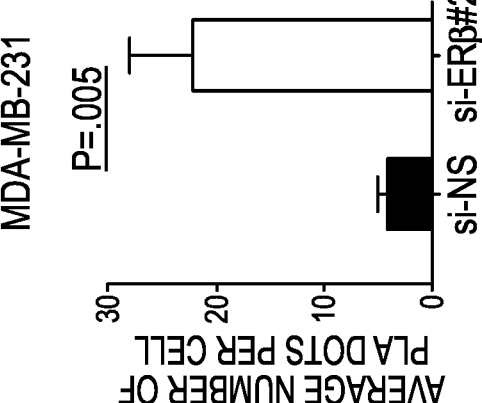
Figure 19C:
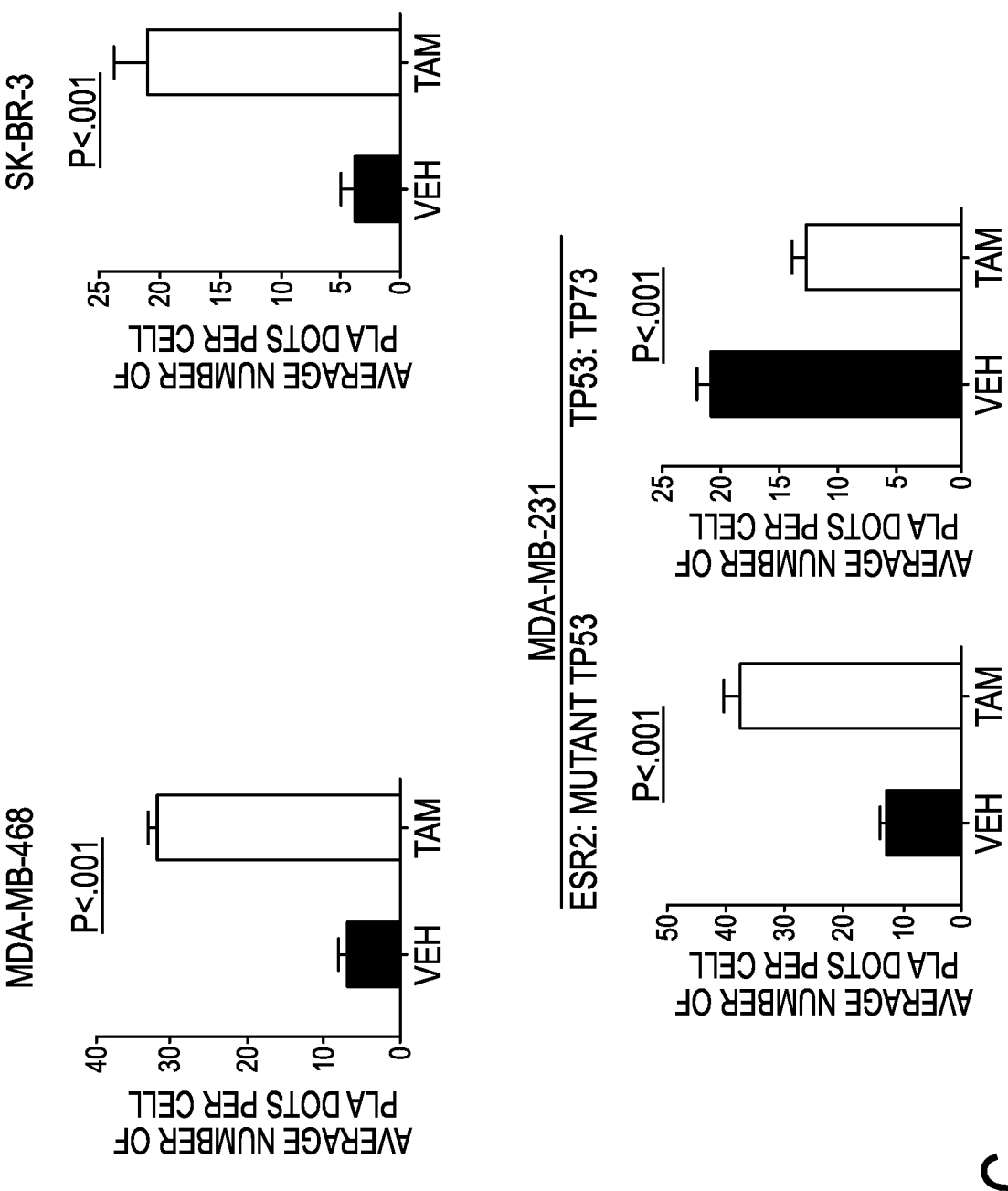

FIGS. 19A-C. Quantitation of PLA signals. PLA signals were counted manually as well as using Blob-Finder image analysis software (developed by Centre for Image Analysis, Uppsala University, Sweden). (A) Quantification of PLA data in FIGS. 1A-M is shown. (B) Quantification of PLA data in FIGS. 6A-J is shown. (C) Quantification of PLA data shown in the FIGS. 7A-J is shown. Random fields (minimum three) were selected for dots counting per nucleus. Average dots/nucleus were considered for the statistical analysis. Two-tailed Student's t-test was performed using GraphPad Prism 7.0. ERβ=ESR2, PLA=proximity ligation assay; si-NS=non-specific siRNA; si-ESR2 #2=ESR2 specific siRNA; VEH=Vehicle; TAM=4-Hydroxytamoxifen.

Figure 21A:
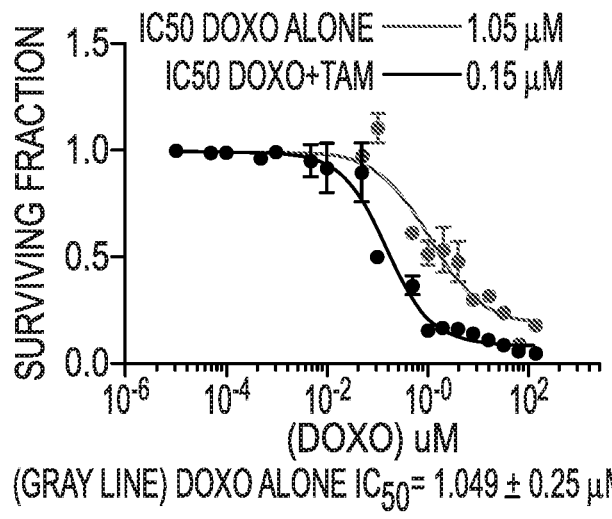
Figure 21B:
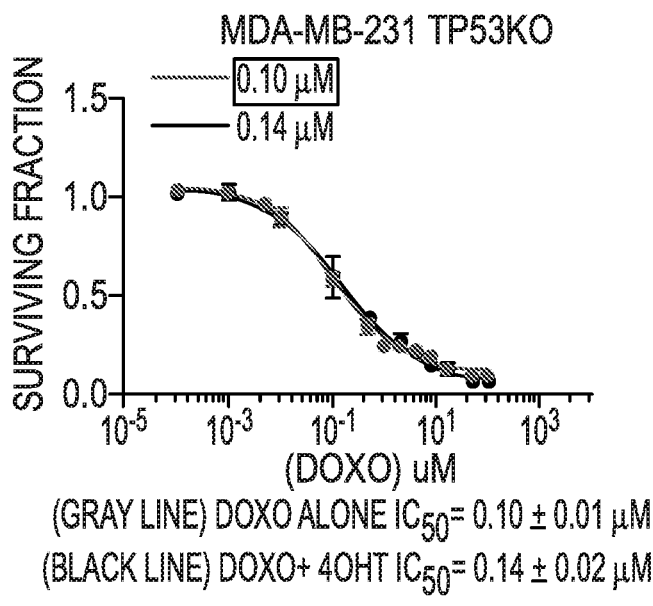
Figure 21C:
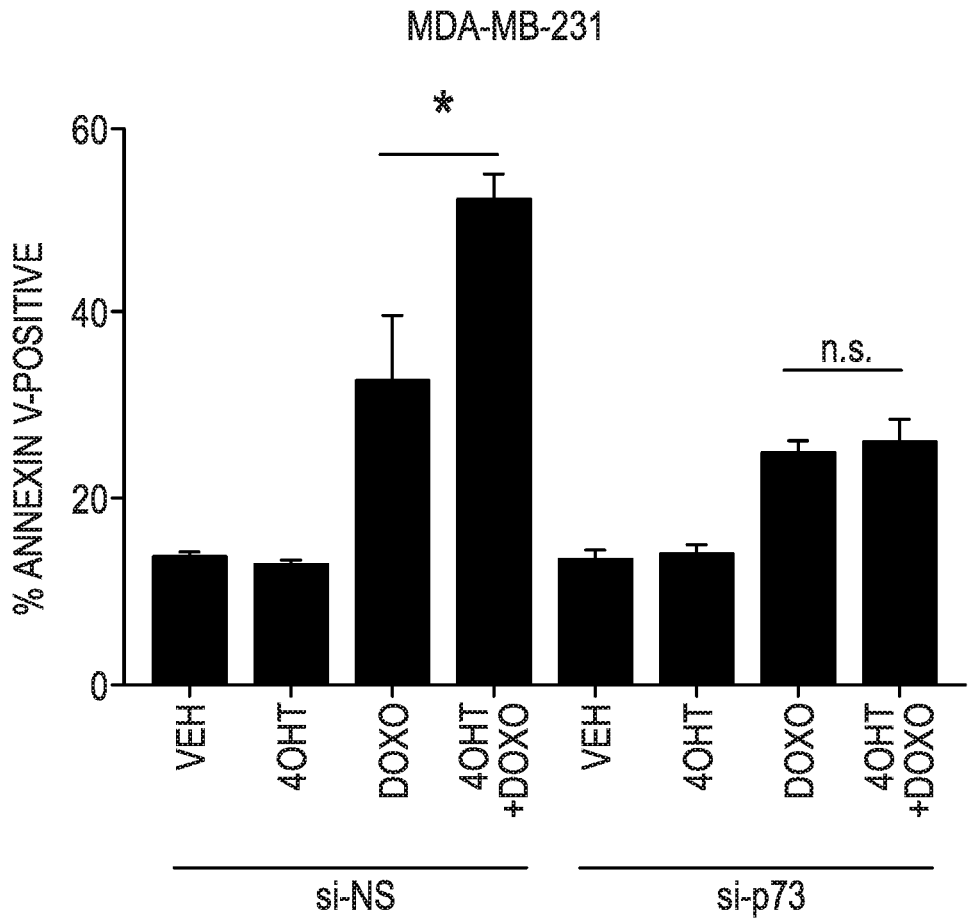

FIGS. 21A-C. (A) In triple negative breast cancer (TNBC) cells (MDA-MB-231) expressing mutant p53, the IC50 (drug concentration required to kill 50% cells) of doxorubicin is 1.05 UM (gray line). Addition of tamoxifen (4OHT) decreases the IC50 about 7-fold (0.15 μM) (black line). Doxorubicin is therefore 7 times more efficient in killing cells when combined with tamoxifen. (B) However, this benefit of adding tamoxifen is lost when the mutant p53 is removed (knocked out) of the cells. (C) Tamoxifen counteracts the mutant p53 effect (via ERβ and p73 (as also shown in Section 6.1, Example 1). Cell death increased (measured by increased in Annexin V-positivity) when the drugs are combined, and this effect is dependent on p73.

FIGS. 21A-C. (A) In triple negative breast cancer (TNBC) cells (MBA-MB-231) expressing mutant p53, the IC50 (drug concentration required to kill 50% cells) of doxorubicin is 1.05 μM (gray line). Addition of tamoxifen (4OHT) decreases the IC50 about 7-fold (0.15 μM) (black line). Doxorubicin is therefore 7 times more efficient in killing cells when combined with tamoxifen. (B) However, this benefit of adding tamoxifen is lost when the mutant p53 is removed (knocked out) of the cells. (C) Tamoxifen counteracts the mutant p53 effect (via ERβ and p73 (as also shown in Section 6.1, Example 1). Cell death increased (measured by increased in Annexin V-positivity) when the drugs are combined, and this effect is dependent on p73.

Figure 22A:
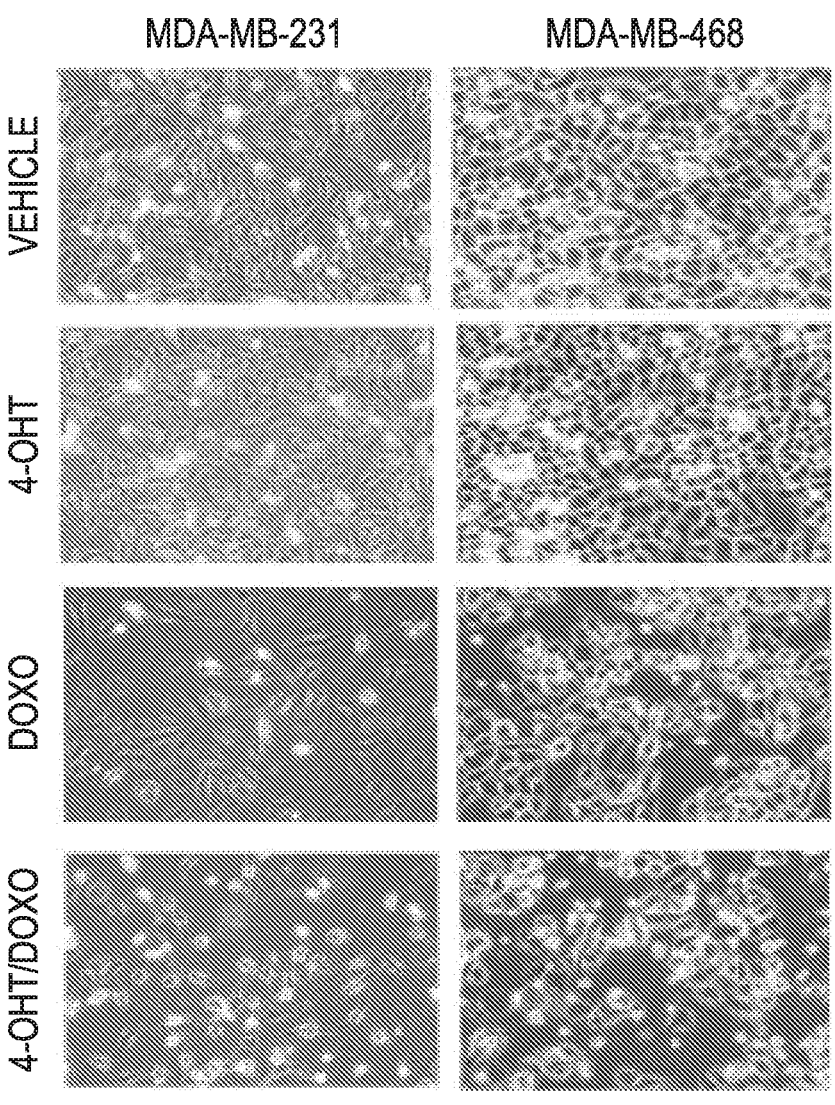
Figure 22B:
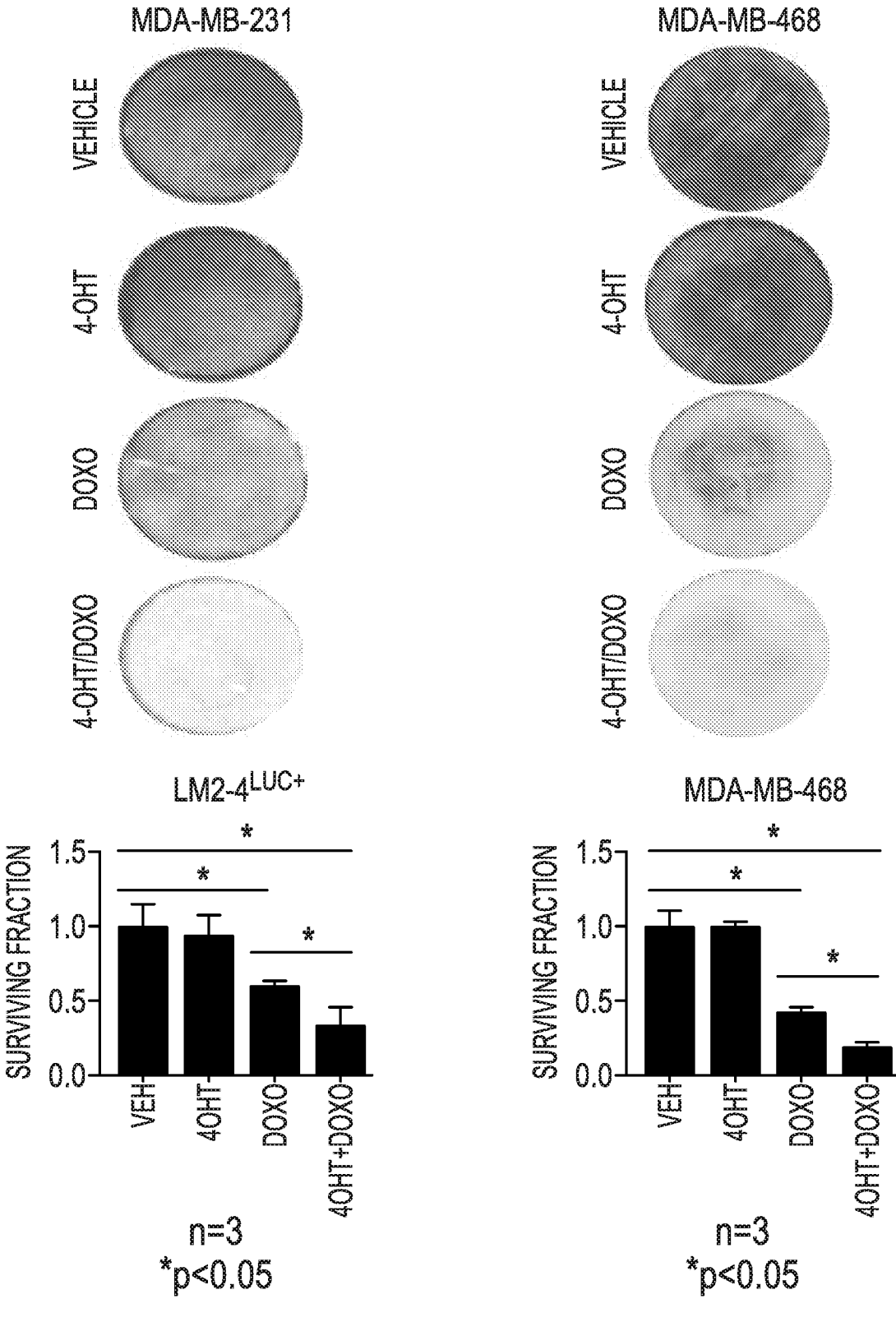
Figure 22C:
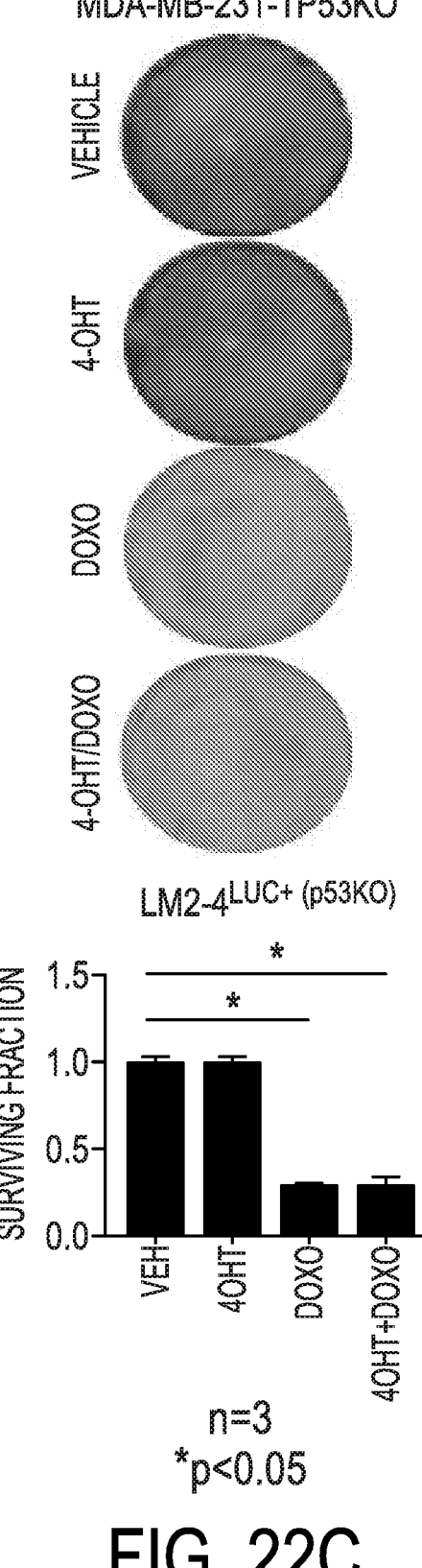

FIGS. 22A-C. (A) Phase contrast microscopy. Cell killing is more pronounced when the drugs are combined. (B) Crystal violet assay demonstrates that cell killing is greater when the drugs are combined in two different triple negative breast cancer cell lines. (C) Crystal violet assay demonstrates that the enhanced cell killing effect is absent in the cell line where mutant p53 is knocked out.

Figure 23:
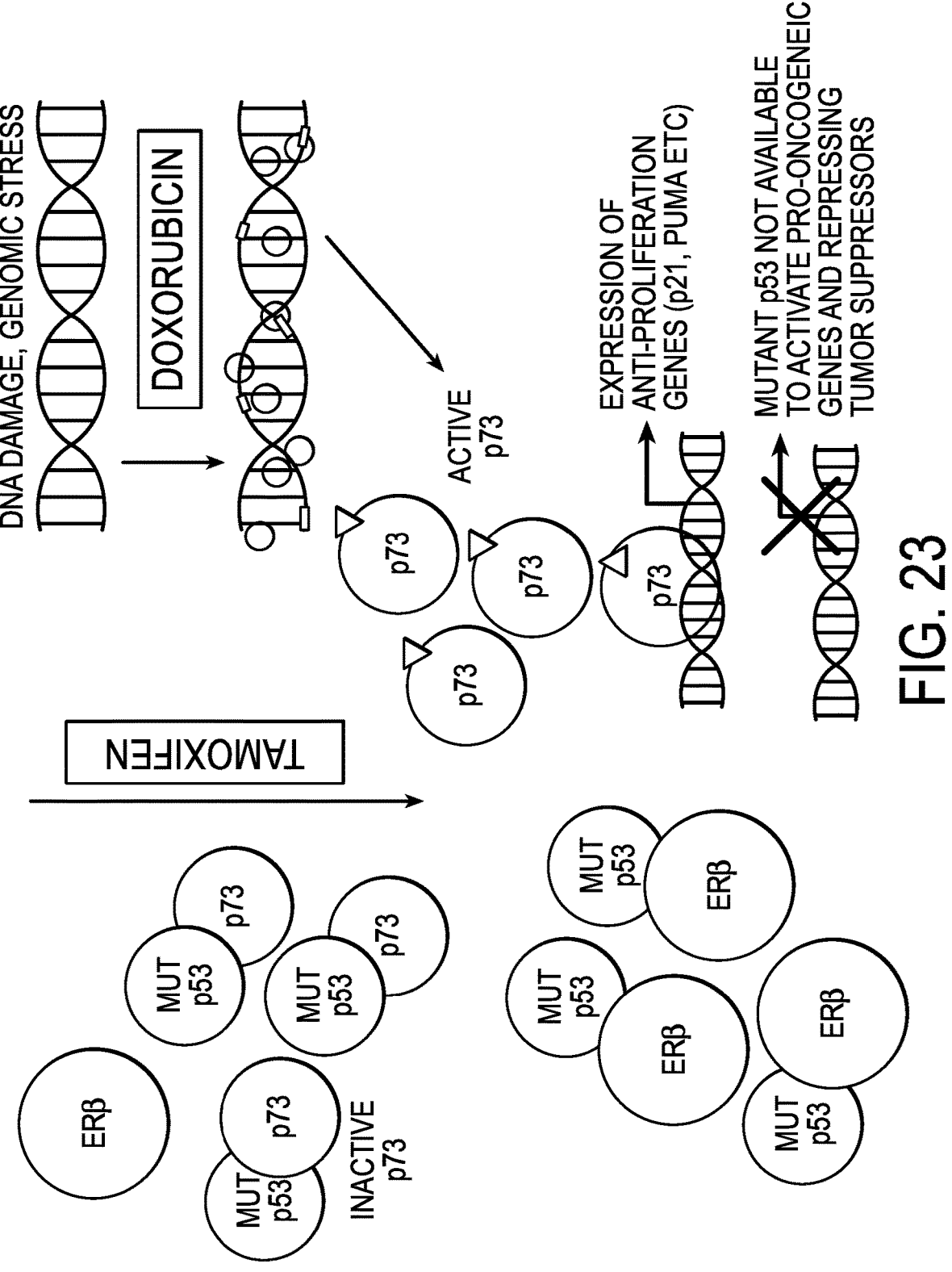

FIG. 23. Diagram of mechanism of action. Mutant p53 binds and constrains p'73, a tumor suppressor. When treated with tamoxifen, ERβ levels increases leading to increased sequestration of mutant p53 leading to reactivation of p73. Such reactivation is further increased because of response to DNA damage caused by Doxorubicin treatment. The activated p73 exerts its tumor suppressor activity.

Figure 24A:
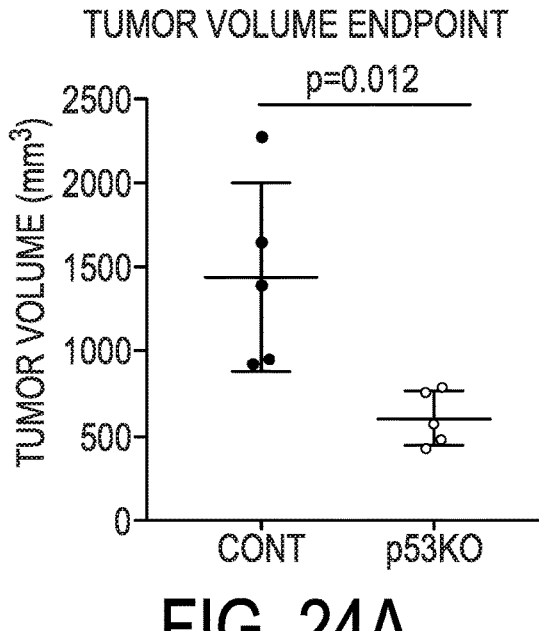
Figure 24B:
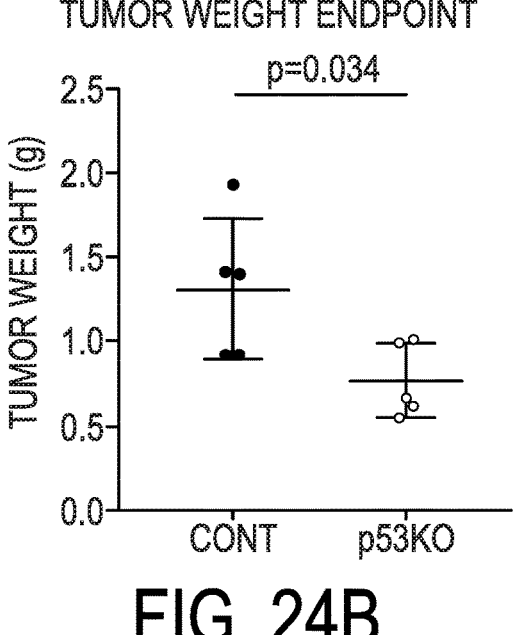

FIGS. 24A-B. Growth of TNBC tumors in an in vivo tumor xenograft model, as measured by tumor volume (A) and tumor weight (B) is decreased when mutant TP53 is knocked out.

Figure 25A:
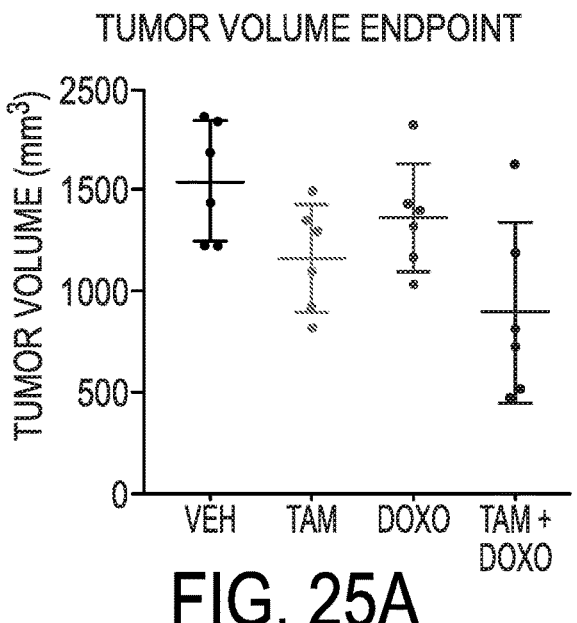
Figure 25B:
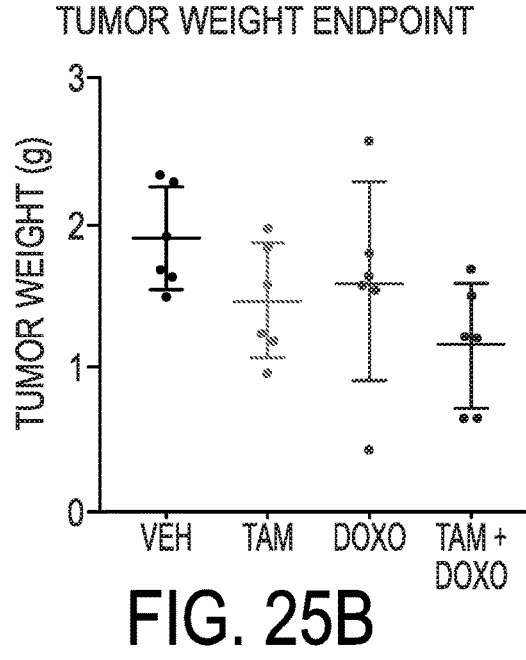

FIGS. 25A-B Growth of TNBC tumors in an in vivo tumor xenograft model, as measured by tumor volume (A) and tumor weight (B) is decreased when a combination of tamoxifen and doxorubicin is administered.

DETAILED DESCRIPTION

A first aspect of the present invention is directed to a method for inducing cancer cell death. This method comprises selecting a population of cancer cells expressing estrogen-receptor β (ERβ) and mutant tumor protein 53 (TP53), and administering, to the population of cancer cells, an agent that increases ERβ protein expression in an amount effective to induce cancer cell death in the population of cancer cells.

The method of inducing cancer cell death can be carried out in vitro, in vivo, or ex vivo to a subject.

Accordingly, a related aspect of the present invention is directed to a method for treating a subject having cancer. This method comprises selecting a subject having a cancer that is characterized by cancer cells expressing estrogen-receptor β (ERβ) and mutant tumor protein 53 (TP53), and administering, to the selected subject, an agent that increases ERβ protein expression in an amount effective to induce cell death in the cancer cells of the subject, thereby treating the subject having cancer.

In accordance with these aspects of the present invention, the cancer and cancer cells to be treated include any cancer characterized by cancer cells expressing the ERβ and a mutant TP53. As described herein, it has been discovered the ERβ binds to oncogenic mutant TP53 (mTP53) and antagonizes mTP53 oncogenic activity, thereby inducing cancer cell apoptosis.

Cancers

In one embodiment, the cancer is triple-negative breast cancer. "Triple negative breast cancer" (TNBC) refers to a cancer characterized by breast cancer cells that are negative for the estrogen receptor (ER), progesterone receptor (PR) and the HER2/neu (HER2) receptor. The "triple negative" status for breast cancer cells is generally associated with a poor prognosis in early breast cancer patients. Treatment options for TNBC are limited to chemotherapy, radiation and surgery, because, as a result of its triple negative status, this breast cancer is unresponsive to hormone modulation with selective estrogen receptor modulators or SERMs, aromatase inhibitors, or selective estrogen receptor degraders or SERDs. However, the discovery (i) that ERβ antagonizes mTP53's oncogenic function, (ii) that agents, such as tamoxifen, enhance this ERβ-mTP53 interaction, and (iii) that this combination of ERβ expression and mTP53 is found in 70-80% of TNBC patients, opens the door to a new line of therapy for a large subset of TNBC patients.

In one embodiment, the cancer is basal-like breast cancer. Basal-like breast cancer is similar to triple-negative breast cancer because the cancer cells often do not have receptors for estrogen, progesterone, and HER2. However, basal-like breast cancer can differ from TNBC by changes in other proteins that are not similarly affected in TNBC.

Other cancers known to express ERβ and mutant TP53 that will also benefit from treatment with an agent that increases the protein expression of ERβ include, without limitation, ovarian cancer, lung cancer, glioma, and colon cancer. Other cancers that may express ERβ and mutant TP53 and therefore will also benefit from treatment with an agent that increases the protein expression of ERβ include, without limitation, pancreatic cancer, bone cancer, brain cancer, cervical cancer, gallbladder cancer, gastrointestinal cancer, neck cancer, throat cancer, thyroid cancer, liver cancer, melanoma, bladder cancer and leukemia.

In an embodiment, a population of cancer cells is selected from the group consisting of a population of triple-negative breast cancer cells, a population of ovarian cancer cells, a population of lung cancer cells, a population of glioma cells, and a population of colon cancer cells.

Therapeutic Agents that Increase ERβ Protein Expression

In accordance with this aspect of the present invention, the therapeutic agent is an agent that increases ERβ protein expression, which in turn increases ERβ-mutant TP53 interaction and decreases mutant oncogenic activity. As described herein, it has been unexpectedly found that tamoxifen increases the expression of ERβ when administered to cancerous cells. Thus, in one embodiment, the agent that increases ERβ expression is tamoxifen.

In one embodiment, the agent that increases ERβ expression is a tamoxifen metabolite. In one embodiment, the tamoxifen metabolite is endoxifen. In another embodiment, the tamoxifen metabolite is 4-hydroxy tamoxifen. In another embodiment, the agent is a structural analogue of tamoxifen. In another embodiment, the agent is a derivative of tamoxifen. Suitable tamoxifen metabolites, derivative, and structural analogues are known and available in the art, see e.g., U.S. Pat. No. 6,096,874 to Wallace et al., U.S. Pat. Nos. 4,536,516, 5,457,113, 5,047,431, 5,441,986, 5,426,123, 5,384,332, 5,453,442, 5,492,922, 5,462,937, 5,492,926, 5,254,594.

In another embodiment, the agent that increases ERβ expression is fulvestrant (7-alpha-[9-(4,4,5,5,5-pentafluoropentylsulphinyl)nonyl]-estra-1,3,5(10)-triene-3, 17(3 diol) (Mishra et al., "Fulvestrant Inhibits Growth of Triple Negative Breast Cancer and Synergizes with Tamoxifen in ERα positive Breast Cancer by Up-regulation of ERβ," Oncotarget 7(35):56876-56888 (2016). Formulations of fulvestrant suitable for use in accordance with the methods described herein are known in the art (see e.g., US20040175402 to Gellert et al., U.S. Pat. No. 9,180,088 to Palepu, U.S. Pat. No. 8,466,139 to Evans et al., and U.S. Pat. No. 9,833,459 to Faraj). Metabolites, derivatives, and structural analogues of fulvestrant that similarly increase ERβ expression are also suitable for use in accordance with this aspect of the present invention.

Chemotherapeutic Drugs and Agents

In one embodiment, at least one chemotherapeutic drug is administered to the subject having cancer, or to the cancer cells themselves, in combination with the agent that increases ERβ protein expression. Suitable chemotherapeutic drugs include, but are not limited to, alkylating agents, such as the following: chlorambucil (an alkylating agent that interferes with DNA replication and RNA transcription leading to disruption of functioning of DNA), cyclophosphamide (an alkylating agent that interferes with DNA replication and RNA transcription leading to disruption of functioning of DNA), CCNU (Lomustine, a nitrosourea alkylating agent that interferes with DNA replication and RNA transcription, and protein synthesis), melphalan (a cell cycle-nonspecific alkylating agent that alkylates and impairs DNA replication, causing cell lysis), procarbazine (an alkylating agent that inhibits DNA, RNA, and protein synthesis), thiotepa (an alkylating agent that interferes with DNA replication and RNA transcription leading to disruption of functioning of DNA), BCNU (Carmustine, an alkylating agent that causes crosslinks and strand breaks in DNA), carboplatin (an alkylating agent that forms intra- and inter-strand crosslinks in DNA leading to DNA damage), and busulfan.

Suitable chemotherapeutic drugs also include, but are not limited to, antimetabolites, such as the following: methotrexate (inhibits folic acid reductase leading to DNA, RNA, and protein synthesis arrest), 6-mercaptopurine (purine antagonist that blocks DNA and RNA synthesis), gemcitabine (a pro-drug that is activated to 5-fluorouracil (5-FU) preferentially in tumor tissues), capecitabine (a pro-drug that is activated to 5-fluorouracil (5-FU) preferentially in tumor tissues), and 5-fluorouracil (interferes with DNA and RNA synthesis).

Suitable chemotherapeutic drugs also include, but are not limited to, anthracyclines such as: daunorubicin (inhibits DNA synthesis and has anti-mitotic and immunosuppressive properties), doxorubicin (binds to nucleic acids (DNA and RNA) by intercalation leading to genomic damage), idarubicin (intercalating analogue of daunorubicin), epirubicin (closely related to daunorubicin and doxorubicin and generates cytotoxic free radicals), and mitoxantrone (interacts with DNA and inhibits topoisomerase causing cell lysis).

Suitable chemotherapeutic drugs also include, but are not limited to, antitumor antibiotics such as: bleomycin (antitumor antibiotic that inhibits DNA and RNA synthesis).

Suitable chemotherapeutic drugs also include, but are not limited to, monoclonal antibodies such as Alemtuzumab (binds to CD52, a protein present on the surface of mature lymphocytes), Bevacizumab (slows the growth of new blood vessels by inhibiting vascular endothelial growth factor A (VEGF-A)), Cetuximab (chimeric mouse/human monoclonal antibody targeting the epidermal growth factor receptor (EGFR)), Gemtuzumab (monoclonal antibody to CD33 linked to a cytotoxic agent from the class of calicheamicins (potent anti-tumor antibiotics); used to treat acute myeloid leukemia), Ibritumomab (monoclonal antibody radioimmunotherapy treatment for relapsed or refractory, low grade or transformed B cell non-Hodgkin's lymphoma, a lymphoproliferative disorder), Panitumumab (fully human monoclonal antibody that is specific to the epidermal growth factor receptor (also known as EGF receptor, EGFR, ErbB-1 and HER1 in humans), Rituximab (a chimeric monoclonal antibody against the protein CD20, which is primarily found on the surface of immune system B cells, and when bound to CD20, triggers cell death; used to treat certain autoimmune diseases and types of cancer), Tositumomab, and Trastuxmab (also known as HERCEPTIN®, a monoclonal antibody used to treat breast cancer that is HER2 receptor positive).

Suitable chemotherapeutic drugs also include, but are not limited to, platinums, such as cisplatin (chemotherapy medication used to treat a number of cancers including testicular cancer, ovarian cancer, cervical cancer, breast cancer, bladder cancer, head and neck cancer, esophageal cancer, lung cancer, mesothelioma, brain tumors and neuroblastoma) and oxaliplatin (also known as ELOXATIN®, a cancer medication used to treat colorectal cancer, and often used together with fluorouracil and folinic acid (leucovorin) in advanced cancer).

Suitable chemotherapeutic drugs also include, but are not limited to, antimicrotubular agents, such as: eribulin (also known as HALAVEN® (Eisai Co.), E7389 and ER-086526, and US NCI designation NSC-707389; used to treat certain patients with breast cancer and liposarcoma), ixabepilone (INN (Bristol-Myers Squibb), also known as azaepothilone B, BMS-247550), vinorelbine (NVB, also known as NAVELBINE® among others, used to treat a number of types of cancer including breast cancer and non-small cell lung cancer), docetaxel ((DTX or DXL), also known as TAXOTERE® among others, used to treat a number of types of cancer including breast cancer, head and neck cancer, stomach cancer, prostate cancer and non-small-cell lung cancer; disrupts microtubular networks), and vincristine (also known as leurocristine and ONCOVIN® among others, is used to treat a number of types of cancer including acute lymphocytic leukemia, acute myeloid leukemia, Hodgkin's disease, neuroblastoma, and small cell lung cancer).

Suitable chemotherapeutic drugs also include, but are not limited to, antineoplastic agents, such as mutamycin (mitomycin), which selectively inhibits the synthesis of DNA. The guanine and cytosine contents correlate with the degree of mutamycin (mitomycin)-induced cross-linking. At high concentrations of the drug, cellular RNA and protein synthesis are also suppressed.

Suitable chemotherapeutic drugs also include, but are not limited to, topoisomerase inhibitors, which are chemical compounds that block the action of topoisomerases (topoisomerase I and topoisomerase II). Topoisomerase I and topoisomerase II are enzymes that control the changes in DNA structure by catalyzing the breaking and rejoining of the phosphodiester backbone of DNA strands during the normal cell cycle.

Suitable chemotherapeutic drugs also include, but are not limited to, plant alkaloids such as vinca alkaloids (anti-mitotic and anti-microtubule alkaloid agents originally derived from the periwinkle plant *Catharanthus roseus* (basionym *Vinca rosea*) and other vinca plants; block beta-tubulin polymerization in dividing cells), taxanes such as paclitaxel (TAXOL®) and docetaxel (TAXOTERE®) (taxanes are a class of diterpenes originally identified from plants of the genus *Taxus* (yews), and feature a taxadiene core), albumin-bound paclitaxel, and epipodophyllotoxins such as etoposide and teniposide (naturally occurring substances in in the root of the American Mayapple plant (*Podophyllum peltatum*); some epipodophyllotoxin derivatives are currently used in the treatment of cancer, acting by inhibiting topoisomerase II). Suitable chemotherapeutic drugs also include, but are not limited to, PD-1 and PD-L1 check point inhibitors such as pembrolizumab (KEYTRUDA®).

In an embodiment, the chemotherapeutic drug is selected from the group consisting of: doxorubicin, carboplatin, cyclophosphamide, daunorubicin, epirubicin, 5-fluorouracil, gemcitabine, eribulin, ixabepilone, methotrexate, Mutamycin, mitoxantrone, vinorelbine, paclitaxel, albumin-bound paclitaxel, docetaxel, thiotepa, vincristine, and capecitabine.

Methods of Administration

In one embodiment, the method for treating a subject having cancer that is characterized by cancer cells expressing estrogen-receptor β (ERβ) and mutant tumor protein 53 (TP53) comprises administering, to the subject, an agent that increases ERβ protein expression in combination with doxorubicin. In one embodiment, the method comprises administering the combination of tamoxifen and doxorubicin.

When administering the at least one chemotherapeutic drug in combination with an agent that increases ERβ protein expression, the administering can be carried out in vitro, in vivo, or ex vivo to a subject. When administering the at least one chemotherapeutic drug in combination with an agent that increases ERβ protein expression, the normal, monotherapeutic dose of the chemotherapeutic drug is significantly reduced. In one embodiment, the dose of the chemotherapeutic agent for the subject being treated is reduced by 5%, 10%, 15%, 20%, 25%, 30%, 35%, 40%, 45%, 50%, or >50% of the monotherapeutic dose of that subject having cancer.

The agent that increases ERβ protein expression and the at least one chemotherapeutic drug can be administered simultaneously or sequentially to the subject having cancer. In one embodiment, the agent that increases ERβ protein expression is administered prior to the administering of the at least one chemotherapeutic agent, i.e., 1, 2, 3, 4, 5, 6, 7, 8, 9, 10, 11, 12, 13, 14, 15, 16, 17, 18, 19, 20, 21, 22, 23, 24 hours or >24 hours prior the administration of the chemotherapeutic agent(s). In another embodiment, the chemotherapeutic agent is administered prior to the administering the agent that increases ERβ protein expression, i.e., 1, 2, 3, 4, 5, 6, 7, 8, 9, 10, 11, 12, 13, 14, 15, 16, 17, 18, 19, 20, 21, 22, 23, 24 hours or >24 hours prior the administration of the agent that increases ERβ protein expression.

In accordance all aspects of the present invention, the subject being treated is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs and the like).

In practicing this and other aspects of the present invention that involve administering a therapeutic agent, e.g., an agent that increases ERβ protein expression, the administering step is be carried out systemically or via direct or local administration. By way of example, suitable modes of systemic administration include, without limitation orally, topically, transdermally, parenterally, intradermally, intramuscularly, intraperitoneally, intravenously, subcutaneously, or by intranasal instillation, by intracavitary or intravesical instillation, intraocularly, intraarterialy, intralesionally, or by application to mucous membranes. Suitable modes of local administration include, without limitation, catheterization, implantation, direct injection, dermal/transdermal application, or portal vein administration to relevant tissues, or by any other local administration technique, method or procedure generally known in the art. The mode of affecting delivery of agent will vary depending on the type of therapeutic agent and the cancer or other condition to be treated.

Another aspect of the present invention is directed to a method for increasing estrogen receptor β (ERβ) expression levels in a subject in need thereof. This method comprises selecting a subject having low ERβ levels, and administering, to the subject, tamoxifen in an amount effective to increase ERβ protein levels in the subject.

As described herein, it has unexpectedly been found that tamoxifen can increase ERβ protein levels. Thus, the administration of tamoxifen to a subject having a low ERβ protein levels will aid in the treatment this deficiency and conditions associated with ERβ deficiencies. Individuals that will benefit from such therapy include, without limitation, individuals having a neurodegenerative disease such as Alzheimer's disease (Tian et al., "Estrogen Receptor Beta Treats Alzheimer's Disease," *Neural Regen. Res.* 8(5):420-426 (2013)), individuals have a neurological condition including, without limitation, depression or schizophrenia; individuals having a cardiovascular condition (Pedram et al., "Estrogen Receptor-13 Prevents Cardiac Fibrosis," *Mol. Endocrinol.* 24(11): 2152-65 (2010); Pedram et al., "Estrogen Inhibits Cardiac Hypertrophy: Role of Estrogen Receptor-Beta to Inhibit Calcineurin," *Endocrinology* 149(7): 3361-9 (2008); Babiker et al., "Estrogen Receptor Beta Protects the Murine Heart against Left Ventricular Hypertrophy," *Aterioscler Thromb Vasc Biol.* 26(7): 1524-30 (2006)) individuals having colorectal cancer (Williams et al., "Estrogen Receptor beta as Target for Colorectal Cancer Prevention," *Cancer Lett.* 372(1):48-56 (2016)).

In one embodiment, the tamoxifen therapy is administered systemically. In another embodiment, the tamoxifen therapy is administered locally to target the particular organ, tissue, or cells where the ERβ deficiency requires correction.

Another aspect of the present invention is directed to a method for treating a subject having cancer. This method comprises selecting a subject having a cancer characterized by cancer cells expressing estrogen-receptor β (ERβ) and wildtype (WT) tumor protein 53 (TP53), and administering, to the subject, an agent that inhibits ERβ and TP53 binding interaction in an amount effective to induce cell death is the cancer cells of the subject, thereby treating the subject having cancer.

In accordance with this aspect of the present invention, the cancer and/or cancer cells to be treated include any cancer characterized by cancer cells expressing the ERβ and a wildtype TP53. As described herein, it has been discovered the ERβ binds to wildtype TP53 and inhibits its tumor suppressor activity. Thus, inhibition of the ERβ and wildtype TP53 binding interaction will enhance TP53 tumor suppressor function, thereby enhancing cancer cell death and treating the subject having cancer. Exemplary cancers where ERβ and wildtype TP53 are expressed together include, without limitation, triple-negative breast cancer, ovarian cancer, lung cancer, glioma, and colon cancer.

In accordance with this aspect of the present invention, the agent that inhibits ERβ and wildtype TP53 binding interaction is an ERβ selective antagonist. Suitable ERβ selective antagonists include, without limitation, 4-[2-Phenyl-5,7-bis(tiifluoromethyl)pyrazolo[1,5-a]pyrimidin-3-yl] phenol (PHTPP) and 2-phenyl-3-(4-hydroxyphenyl)-5,7-bis (trifluoromethyl)-pyrazolo[1,5-a]pyrimidine.

In another embodiment, the agent that inhibits ERβ and wildtype TP53 binding interaction is an ERβ selective agonist. Selective ERβ agonists include, without limitation, 5-androstane-3β-diol (Adiol), 8β-VE$_2$, apigenin, daidzein, DCW234, dehydroepiandrosterone, ERB-79, ERV-196, erteberel (LYS500307), FERb033, genistein, kaempferol, liquiritigenin, penduletin, prinaberel, s-equol ((s)-4',7-isoflavandiol), Inadazole-Br, Inadazole-C1, WAY166818, WAY-200070, and WAY-214156.

Another aspect of the present invention is directed to a method that comprises obtaining a cancer cell sample from a subject; detecting, in the sample, a level of estrogen-receptor β (ERβ) protein expression; and detecting, in the sample, a level of tumor protein 53 (TP53) protein expression. In an embodiment, wildtype TP53 protein expression is detected. In another embodiment, mutant TP53 protein expression is detected. In another embodiment, the method further comprises detecting a binding interaction between ERβ and the TP53 in the sample.

In one embodiment, the TP53 is a mutant form of TP53. In another embodiment, the TP53 is wildtype TP53. This method can be utilized to guide and/or identify a suitable course of treatment for the subject.

In accordance with this aspect of the present invention, if the cancerous sample tests positive for both the expression of ERβ and mutant TP53, then the subject's therapeutic regimen should be modified to include administration of an agent that increases the expression of ERβ. As described supra, suitable agents for increasing ERβ expression include, but are not limited to, tamoxifen, tamoxifen metabolites (e.g., 4-hydroxy and endoxifen), tamoxifen structural analogues, and tamoxifen derivative. Other agents suitable for increasing ERβ expression include fulvestrant and metabolites, analogues, and derivatives thereof.

If the cancerous sample tests positive for both the expression of ERβ and wildtype TP53, then the subject's therapeutic regimen should be modified or structured to include administration of an agent that inhibits the interaction of ERβ and wildtype TP53.

In one embodiment, an agent that inhibits this interaction is an ERβ selective antagonist. As described supra, suitable ERβ antagonists for inhibiting the interaction of ERβ and wildtype TP53 include, without limitation, 4-[2-Phenyl-5,7-bis(tifluoromethyl)pyrazolo[1,5-a]pyrimidin-3-yl]phenol (PHTPP), and 2-phenyl-3-(4-hydroxyphenyl)-5,7-bis(trifluoromethyl)-pyrazolo[1,5-a]pyrimidine.

In another embodiment, an agent that inhibits the interaction of ERβ and wildtype TP53 is a selective ERβ agonist. Selective ERβ agonists include, without limitation, 5-androstane-3β-diol (Adiol), 8β-VE$_2$, apigenin, daidzein, DCW234, dehydroepiandrosterone, ERB-79, ERV-196, erteberel (LYS500307), FERb033, genistein, kaempferol, liquiritigenin, penduletin, prinaberel, s-equol ((s)-4',7-isoflavandiol), Inadazole-Br, Inadazole-Cl, WAY166818, WAY-200070, and WAY-214156.

The presence of ERβ and TP53 expression can be detected in the cancer sample from the subject using methods well known to those of skill in the art. Suitable methods for measuring protein expression levels in a biological sample generally involve contacting the sample with at least one detectable reagent that is suitable for measuring protein expression, e.g., a labeled antibody or a primary antibody used in conjunction with a secondary antibody, and measuring protein expression level based on the level of detectable reagent in the sample after normalizing to total protein in the sample. Suitable methods for detecting ERB, mutant TP53 and wildtype TP53 protein expression level in a cancerous sample include, for example, immunoassays such as western blot, immunoprecipitation, enzyme-linked immunosorbent assay (ELISA), radioimmunoassay (RIA), or fluorescent activated cell sorting (FACS).

In one embodiment, the binding interaction between ERβ and TP53 is detected, and optionally quantified, in the cancerous sample. Detection of ERβ and TP53 binding interaction can be carried out using methods known to those of skill in the art, e.g., via immunoassays, coimmunoprecipitation assays, and co-purification assays, optionally combined with cross-linking to stabilize the binding. Identities of the isolated protein interacting partners can be characterized by, e.g., mass spectrometry. See e.g., Rout et al., *J. Cell. Biol.,* 148:635-651 (2000); Houry et al., *Nature,* 402:147-154 (1999); Winter et al., *Curr. Biol.,* 7:517-529 (1997).

An aspect of the invention is directed to an agent that increases ERβ protein expression in cancer cells for use in treating cancer. Preferably, treating the cancer comprises: selecting a population of cancer cells expressing estrogen-receptor β (ERβ) and mutant tumor protein 53 (TP 53), and administering, to said population of cancer cells, the agent. Preferably, the population of cancer cells is selected from the group consisting of: a population of triple-negative breast cancer cells, a population of ovarian cancer cells, a population of lung cancer cells, a population of glioma cells, and a population of colon cancer cells. Preferably, the population of cancer cells is a population of triple-negative breast cancer cells.

Preferably, said agent that increases ERß protein expression is tamoxifen, a tamoxifen metabolite, a tamoxifen analogue, or a tamoxifen derivative. Preferably, the tamoxifen metabolite is endoxifen.

Preferably, said agent that increases ERß protein expression is fulvestrant, a fulvestrant metabolite, a fulvestrant analogue, or a fulvestrant derivative.

Preferably, treating the cancer further comprises: administering one or more chemotherapeutic drugs to said population of cancer cells in combination with said agent that increases ERß protein expression.

Preferably, said chemotherapeutic drug is selected from the group consisting of: doxorubicin, carboplatin, cyclophosphamide, daunorubicin, epirubicin, 5-fluorouracil, gemcitabine, eribulin, ixabepilone, methotrexate, Mutamycin, mitoxantrone, vinorelbine, paclitaxel, albumin-bound paclitaxel, docetaxel, thiotepa, vincristine, and capecitabine. Preferably, the chemotherapeutic drug is doxorubicin.

Preferably, said administering is carried out in vivo.

Another aspect of the invention is directed to an agent that increases ERß protein expression for use in treating cancer.

Preferably, treating the cancer comprises: selecting a subject having a cancer that is characterized by cancer cells expressing estrogen-receptor β (ERß) and mutant tumor protein 53 (TP53), and administering, to the selected subject, the agent to induce cell death in said cancer cells.

Preferably, the cancer is selected from the group consisting of: triple-negative breast cancer, lung cancer, ovarian cancer, glioma, and colon cancer.

Preferably, the cancer is triple-negative breast cancer.

Preferably, said triple-negative breast cancer is a basal-like breast cancer.

Preferably, said agent increased ERß protein expression is tamoxifen, a tamoxifen metabolite, a tamoxifen analogue, or a tamoxifen derivative.

Preferably, the tamoxifen metabolite is endoxifen.

Preferably, said agent increased ERß protein expression is fulvestrant, a fulvestrant metabolite, a fulvestrant analogue, or a fulvestrant derivative.

Preferably, treating of the cancer comprises: administering, to the selected subject, one or more chemotherapeutic drugs in combination with said agent that increases ERß protein expression.

Preferably, said one or more chemotherapeutic drugs is administered at a dose that is at least 10% less than the dose administered to a patient as a monotherapy.

Preferably, said one or more chemotherapeutic drugs is administered at a dose that is at least 50% less than the dose administered to a patient as a monotherapy.

Preferably, said chemotherapeutic drug is selected from the group consisting: of doxorubicin, carboplatin, cyclophosphamide, daunorubicin, epirubicin, 5-fluorouracil, gemcitabine, eribulin, ixabepilone, methotrexate, Mutamycin, mitoxantrone, vinorelbine, paclitaxel, albumin-bound paclitaxel, docetaxel, thiotepa, vincristine, and capecitabine.

Preferably, the chemotherapeutic drug is doxorubicin.

Preferably, said subject is a human subject.

Another aspect of the invention is directed to Tamoxifen for use in increasing estrogen receptor ß (ERß) expression levels in a subject in need thereof.

Preferably, the use comprises: selecting a subject having low ERß levels, and administering, to said subject, tamoxifen to increase ERß protein levels in said subject.

Preferably, said subject has a neurodegenerative disease or a neurological disease.

Preferably, said subject has Alzheimer's disease.

Preferably, said subject has a cardiovascular condition.

Preferably, said subject has colorectal cancer.

Another aspect of the invention is directed to an agent that inhibits ERß and TP53 binding interaction for use in treating cancer.

Preferably, treating the cancer comprises: selecting a subject having a cancer that is characterized by cancer cells expressing estrogen-receptor β (ERß) and wildtype tumor protein 53 (TP53), and administering, to said subject, the agent to induce cell death in said cancer cells.

Preferably, the cancer is triple-negative breast cancer.

Preferably, said agent that inhibits ERß and TP53 binding interaction is an ERB selective antagonist.

Preferably, the ERß selected antagonist is selected from 4-[2-Phenyl-5,7-bis(tifluoromethyl)pyrazolo[1,5-a]pyrimidin-3-yl]phenol (PHTPP), and 2-phenyl-3-(4-hydroxyphenyl)-5,7-bis(trifluoromethyl)-pyrazolo[1,5-a]pyrimidine.

Preferably, said agent that inhibits ERß and TP53 binding interactions is an ERB selection antagonist.

Another aspect of the invention is directed to Estrogen-receptor ß (ERß) protein and tumor protein 53 (TP53) protein for use in diagnosing and/or treating cancer.

Preferably, the diagnosing and/or treating of the cancer comprises detecting, in a sample, the presence of estrogen-receptor ß (ERß) protein expression and tumor protein 53 (TP53) protein expression.

Preferably, wildtype TP53 is detected.

Preferably, mutant TP53 is detected.

Preferably, said detecting further comprises: detecting a binding interaction between ERß and TP53 in sample.

Preferably, said detecting is carried out using an immunoassay.

Preferably, the use further comprises: administering, to said subject, an agent that increases ERß protein expression in an amount effective to treat said cancer when the presence of ERß and mutant TP53 are detected.

Preferably, the agent that increases ERß protein expression is tamoxifen, a tamoxifen metabolite, a tamoxifen analogue, or a tamoxifen derivative.

Preferably, the tamoxifen metabolite is endoxifen.

Preferably, said agent that increases ERß protein expression is fulvestrant, a fulvestrant metabolite, a fulvestrant analogue, or a fulvestrant derivative tamoxifen.

Preferably, said agent that increases ERß protein expression is administered in combination with one or more chemotherapeutic agents.

Preferably, the use further comprises: administering, to said subject, an agent that inhibits ERß and TP 53 binding interaction in an amount effective to induce cell death is said subject when the presence of ERß and wildtype TP53 are detected.

Preferably, agent that inhibits ERß and TP53 binding interaction is an ERB selective antagonist.

6.1. Example 1: TP53 Status as a Determinant of Pro-Versus Anti-Tumorigenic Effects of Estrogen Receptor-Beta in Breast Cancer Introduction Anti-tumorigenic versus pro-tumorigenic roles of estrogen receptor-beta (ESR2, also referred to herein ERβ) in breast cancer (BC) remain unsettled. This example investigated the potential of TP53 status to be a determinant of the bi-faceted role of ESR2 and associated therapeutic implications for triple negative breast cancer (TNBC). ESR2-TP53 interaction was analyzed with multiple assays including in situ proximity ligation assay (PLA). Transcriptional effects on TP53-target genes and cell proliferation in response to knocking down or overexpressing ESR2 were determined. Patient survival according to ESR2 expression levels and TP53 mutation status was analyzed in the Basal-like/TNBC subgroup in METABRIC (n=308) and Roswell (n=46) patient cohorts by univariate Cox regression and log-rank test. All statistical tests were two-sided.

ESR2 interaction with WT and mutant TP53 caused pro-proliferative and anti-proliferative effects, respectively. Depleting ESR2 in cells expressing WT TP53 resulted in increased expression of TP53-target genes CDKN1A (control group mean=1 [SD=0.13] vs ESR2 depletion group mean=2.08 [SD=0.24]; p=0.003) and BBC3 (control group mean=1 [SD=0.06] vs ESR2 depleted group mean=1.92 [SD=0.25]; p=0.003); however expression of CDKN1A (control group mean=1 [SD=0.21] vs ESR2 depleted group mean=0.56 [SD=0.12]; p=0.02) and BBC3 (control group mean=1 [SD=0.03] vs ESR2 depleted group mean=0.55 [SD=0.09]; p=0.008) was decreased in cells expressing mutant TP53. Overexpressing ESR2 had opposite effects. Tamoxifen increased ESR2-mutant TP53 interaction leading to reactivation of TP73 and apoptosis. High levels of ESR2 expression in mutant TP53-expressing Basal-like tumors is associated with better prognosis (METABRIC cohort: log-rank p=0.001; HR=0.26, 95% Confidence interval=0.08 to 0.84, univariate Cox p=0.02).

This example demonstrates that TP53 status is a determinant of the functional duality of ESR2. The study suggests that ESR2-mutant TP53 combination prognosticates survival in TNBC revealing a novel strategy to stratify TNBC for therapeutic intervention potentially by repurposing tamoxifen.

Background

TNBC, most of which are composed of a basal-like BC molecular subtype, do not express estrogen receptor-alpha (ERα), progesterone receptor (PR), or human epidermal growth factor 2 (HER-2) receptor. Therefore, currently available targeted therapies for BC are not effective against these very aggressive tumors. This, coupled with the long-term ineffectiveness of cytotoxic chemotherapy, makes it urgent to discover new therapeutic targets and strategies to treat TNBC. Although ERα is not expressed, ESR2 is expressed in about 60-80% of TNBC. Furthermore, unlike luminal BCs where TP53 is wild type in majority of cases, TP53 is mutated in about 80% of TNBC. ERα's role as a pro-tumorigenic factor in BC is well established and these studies have shown that ERα is capable of binding and functionally inactivating WT TP53 in luminal BC. ERα-TP53 crosstalk resulting in cooperation or antagonism has also been reported. However, the role of ESR2 in breast cancer has been elusive. Although anti-proliferative role for ESR2 has been proposed primarily based on overexpression of exogenous ESR2 cDNA in cancer cell lines including overexpression in a TNBC cell line to show antagonism toward mutant TP53, data from other studies do not fit this paradigm. For example, treatment of ovariectomized mice with an ESR2-specific agonist resulted in increased cell proliferation to a similar extent that was observed upon treatment with 17β-estradiol (17β-estradiol. Further, markers of cell proliferation co-localize with ESR2 in mammary epithelial cells and in TNBC. Both these observations are inconsistent with an anti-proliferative role for ESR2. More recently, ESR2 has been shown to have a pro-proliferative role in BC stem cells. On the other hand, ESR2 is reported to alleviate the inhibitory effect of ERα on TP53-mediated transcriptional regulation. While some retrospective studies on BC tissues showed that ESR2 is an indicator of favorable prognosis, pro-tumorigenic functions of ESR2 were observed in other studies. Only some of these divergent effects could be attributed to expression of specific isoforms and their cellular location. Such inconsistent observations suggest that ESR2 may have bi-faceted functions depending on the cellular context. However, the mechanisms underlying such bi-faceted functions of ESR2 remain unknown.

Somatic mutations in TP53 are very frequent and are clonally dominant, compared to other genes in TNBC. In addition to losing tumor suppressor properties and exerting dominant-negative regulation over any remaining WT TP53, certain mutant TP53s are known to acquire oncogenic gain-of-function (GOF) properties. Cellular functions mediated by mutant TP53 are context-dependent and include increased invasiveness, angiogenesis, abnormal epigenetic regulation, enhancement of "sternness" and therapeutic resistance. This example analyzed the interaction between ESR2 and TP53 signaling and addressed whether TP53 status could be a determinant of pro-versus anti-proliferative functions of ESR2 impacting clinical outcome in Basal-like/TNBC patients.

Materials and Methods

Proximity Ligation Assay (PLA)

PLA is a sensitive and specific in situ protein-protein interaction assay where signals generated by primary and secondary antibodies are amplified by rolling circle replication of circular DNA generated by antibody-liked oligonucleotides, followed by fluorescent labeling to produce punctuate fluorescent dots (Soderberg O, et al. Nat Methods 2006; 3(12):995-1000). PLA was performed using the Duolink II (Olink Bioscience)/Millipore-Sigma reagents and protocol.

Immunohistochemical Staining and Scoring of the Human BC Tissue Micro Array (TMA)

A tissue micro-array (TMA) was constructed using three 1-millimeter tissue cores (triplicates) from tumor specimens and controls from eligible patients, who had surgeries performed between 1995 and 2008 at Roswell Park Comprehensive Cancer Center (Roswell), Buffalo, N.Y. The TMAs used in this study were generated from pre-existing paraffin blocks, and as per the Institutional Review Board they are "exempt" as they contain no patient identifiers. After staining with TP53 and ESR2 antibodies, TMA slides were digitally scanned using Aperio Scanscope (Aperio Technologies, Inc., Vista, Calif.), and nuclear ESR2 and TP53 immunohistochemistry (IHC) signals were quantitatively scored. The High/Low expression classification was determined by the median of the observed patient-level IHC H-Scores.

Analysis of Molecular Taxonomy of Breast Cancer International Consortium (METABRIC) Data METABRIC clinical data including survival data, mRNA expression data, TP53 mutation status and PAM50 subtype information was previously published (Pereira B, et al. Nat Commun 2016; 7:11479; Curtis C, et al. Nature 2012; 486(7403):346-52) and was downloaded from the World Wide Web at cbioportal.org. Overall survival and breast cancer-specific survival (BCSS), defined as the time of diagnosis to the time of a BC-related death, were used for the survival analyses in the Basal-like subgroup (n=308).

Statistical Analyses

All P values are interpreted as described in 2016 ASA P Value Statement (Wasserstein R L, et al. The American Statistician 2016; 70(2):129-133). Statistical significance of comparison of relative gene expression, cell growth, cell cycle and apoptosis assays were determined by Student's t-test. Statistical significance of BCSS from METABRIC was tested using Univariate cox analysis (treating ESR2 log 2 expression values as a continuous variable) or log-rank test (defining two or three patient groups according to low or high ESR2 expression). All statistical tests were two-sided. p values less than 0.05 were deemed statistically significant throughout, with no adjustment for multiplicity.

Supplementary Materials and Methods

Cell lines and culturing. MCF 10A, MCF-7, ZR-75-1, T-47D, CAL-51, MDA-MB-231, MDA-MB-468, MDA-MB-231-LM2.4$^{Luc}$, SK-BR-3, BC3-WT TP53, BC3-shTP53 cells were cultured in Dulbecco's Modified Eagle's medium (DMEM 10-013-CV Corning Cellgro) supplemented with 10% fetal bovine serum (FBS 10437-028 Gibco), penicillin (50 IU/ml), and streptomycin (50 g/ml). All cell lines were grown at 37° C., under 5% CO$_2$, in a humidified incubator. MCF 10A cells were maintained in DMEM/F12 with L-Glutamine (Invitrogen #11330-032) medium (500 ml) containing 5% Horse Serum (Invitrogen), 10 μg/mL insulin (Sigma), 20 ng/mL Epidermal growth factor (EGF) (Peprotech) 0.5 μg/mL Hydrocortisone (Sigma), 0.1 μg/mL Cholera toxin (Sigma) and penicillin and streptomycin (Gibco). Suitable cell lines can be obtained from commercial or publicly available sources such as the ATCC. For this example, the following cell lines were used: MCF-7, MDA-MB-231, MDA-MB-231-LM2.4$^{Luc+}$, SK-BR-3, CAL-51, BC3-WT TP53, BC3-shTP53. All cell lines were authenticated by short tandem repeat (STR) analysis.

siRNA transfections. Specific siRNAs were transiently transfected using Lipofectamine 2000 and 3000 as per the manufacturer's instructions (ThermoFisher Scientific). Cells were transfected with a final concentration of 120 nM stealth control or ESR2-specific siRNA (Invitrogen #12935-300) or TP73-specific siRNA (80 nM). Cells were harvested 48 hours post-siRNA-transfection for further analysis. Sequence information of siRNAs is set forth in Table 1 below.

TABLE 1

| | Oligonucleotide primers used | |
|---|---|---|
| Primer | | Sequence (5'-3')/ Reference |
| ESR2-1 (ERβ1) Cloning Primers | CtHA-NotI-Forward | CCATAGCGGCCGCCACCATGGAT ATA AAA AC TCACCATCTAGC (SEQ ID NO: 1) |
| | CtHA-MluI-Reverse | GGTCA ACG CGT TCA AGC GTA ATC TGG AAC ATC GTA TGG GTA AGC GTA ATC TGG AAC ATC GTA TGG GTA CTG AGA CTG TGG GTT CTG GGA GC (SEQ ID NO: 2) |
| RT-PCR Primers | Pan-ERβ-RT-Forward1 | CCT ATG TAG ACA GCC ACC ATG AAT (SEQ ID NO: 3) |
| | Pan-ERβ-RT-Reverse1 | CCC ACC TCC CAA GTT AGT GAC ATT (SEQ ID NO: 4) |
| | HA-ERβ-RT-Forward | GCT TTG GTT TGG GTG ATT GCC A (SEQ ID NO: 5) |
| | HA-ERβ-RT-Reverse | CGT TCA AGC GTA ATC TGG AAC (SEQ ID NO: 6) |
| | ERβ1, 2, 4, 5-RT-Forward and Reverse 'Triple Primers': Forward | CGATGCTTTGGTTTGGGTGAT (SEQ ID NO: 7) |
| | ERβ1-RT-Reverse | GCCCTCTTTGCTTTTACTGTC (SEQ ID NO: 8) |
| | ERβ2, 4, 5-RT-Reverse | CTTTAGGCCACCGAGTTGATT (SEQ ID NO: 9) |
| | β-Actin-RT-Forward | ATG GGT CAG AAG GATTCC TAT GT (SEQ ID NO: 10) |
| | β-Actin-RT-Reverse | AAG GTC TCA AAC ATG ATCTGG G (SEQ ID NO: 11) |
| | p21-RT-Forward | GAG ACT CTC AGG GTC GAA AAC G (SEQ ID NO: 12) |
| | p21-RT-Reverse | GAT GTA GAG CGG GCC TTT GA (SEQ ID NO: 13) |
| | PUMA-RT-Forward | ATG CCT GCC TCA CCTTCA TC (SEQ ID NO: 14) |
| | PUMA-RT-Reverse | TCA CAC GTC GCT CTCTCT AAA CC (SEQ ID NO: 15) |
| | BTG2-RT-Forward | GTG AGC GAG CAG AGGCTT AAG (SEQ ID NO: 16) |
| | BTG2-RT-Reverse | GAGCCCTTGGACGGCTTT (SEQ ID NO: 17) |
| | NOXA-RT-Forward | ATG AAT GCA CCT TCA CAT TCC T (SEQ ID NO: 18) |
| | NOXA-RT-Reverse | TCC AGC AGA GCT GGA AGT CGA (SEQ ID NO: 19) |
| | CD44-RT-Forward | CCA CGT GGA GAA AAA TGG TC (SEQ ID NO: 20) |
| | CD44-RT-Reverse | CAT GGC GCA GGT CTG TGA C (SEQ ID NO: 21) |
| | VEGFα-RT-Forward | AAC ACA GAC TCG CGT TGC AA (SEQ ID NO: 22) |
| | VEGFα-RT-Reverse | CGG CTT GTC ACA TCT GCA AGT (SEQ ID NO: 23) |
| ChIP Primers | ChIP-Nonspecific (NS)-Forward | CAG AGT GAG ACC TTG TCT GTC TCC (SEQ ID NO: 24) |
| | ChIP-Nonspecific (NS)-Reverse | CAG AAG ATG CAT GCA ACA GCA CCT TG (SEQ ID NO: 25) |
| | p21-ChIP-Forward | CAG CT GTG GCT CTG ATT GG (SEQ ID NO: 26) |
| | p21- ChIP-Reverse | CCT CAC CTG AAA ACA GGC AGC (SEQ ID NO: 27) |
| | PUMA-ChIP-Forward | GCGAGACTGTGGCCTTGTGT (SEQ ID NO: 28) |
| | PUMA-ChIP-Reverse | CGT TCC AGG GTC CAC AAA GTC (SEQ ID NO: 29) |

TABLE 1-continued

| | Oligonucleotide primers used | |
|---|---|---|
| Primer | | Sequence (5'-3')/ Reference |
| siERβ#1 sequence | ESR2 | CCC UGC UGU GAU GAA UUA CAG CAU U (SEQ ID NO: 30) |
| siERβ#2 sequence | ESR2-HSS103380, ThermoFisher | CCU UUA GUG GUC CAU CGC CAG UUA U (SEQ ID NO: 31) |
| siTP73 | siTP73-AM16708, ThermoFisher | GGG ACU UCA ACG AAG GAC Att (SEQ ID NO: 32) |

Antibodies and reagents. Antibodies and reagents are set forth in Table 2 below.

TABLE 2

| | Antibody | Company (Cat. No.) |
|---|---|---|
| Erβ | H-150 | Santa Cruz (sc-8974x) |
| | 68-4 | Millipore (05-824) |
| | 14C8 | Abcam (ab288) |
| | MC10 | Wu, X et al., J Cellular Biochem. 2012. 113: 711-723 |
| TP53 | DO1 | Santa Cruz (sc-126) |
| | FL393 | Santa Cruz (sc-6243) |
| | Pab240 | Santa Cruz (sc-99) |
| | PAb421 | Calbiochem (OP03) |
| | CM1 | Leica Biosystem (NCL-p53-CM1) |
| TP73 | H-79 | Santa Cruz (sc-7957x) |
| | 5B429 | Imgenex (IMG-246) |
| | Anti-p73 | Bethyl Laboratories (A300-126A) |
| | p73 (D3G10) | Cell Signaling (14620) |
| FLAG | Anti-FLAG | Sigma (F1804) |
| HA | HA.11 | Covance (MMS-101P) |
| p21 | Anti-p21 | Santa Cruz (sc-397) |
| PUMA | Anti-PUMA | Sigma (P4618) |
| | H-136 | Santa Cruz (sc-28226) |
| β-actin | Anti-β-actin | Sigma (A5441) |
| PARP | Anti-PARP | Cell Signaling (9542) |
| p21 | p21 Waf1/Cip1 (12D1) | Cell Signaling (2947) |
| BIM | Anti-Bim | Cell Signaling (2933) |
| Caspase 3 | Anti-Caspase-3 | Cell Signaling (9662) |
| BID | Anti-Bid | Cell Signaling (2002) |
| BAX | Bax (D2E11) | Cell Signaling (50230) |
| Western blot secondary | HRP-anti-rabbit | Millipore (12-348) |
| Antibodies | HRP-anti-mouse | Millipore (12-349) |
| Immunofluorescence secondary antibodies | Alexa Fluor 488 anti-mouse | Invitrogen (A11001) |
| | Alexa Fluor 594 anti-rabbit | Invitrogen (A11012) |
| Immunohistochemistry secondary antibodies | HRP-conjugated anti-rabbit HRP-conjugated anti-mouse | DAKO (K4003) Leica (PV-6114) |
| IgG negative controls | Normal mouse IgG | Millipore (12-371) |
| | Normal rabbit IgG | Millipore (12-370) |

Plasmid constructs. Wild type human TP53 (pRc/CMV hp53) and pCR3.1/hERα expression plasmids were used. The pCR3.1/p53 construct was generated by cloning full-length p53 cDNA (HindIII & XbaI fragment) from pRc/ CMV hp53 plasmid into pCR3.1 vector. The human ERβ1cDNA clone was also used. The full-length ERβ was amplified and cloned into BamHI and XhoI restriction sites of pCR3.1 vector. For truncated ERβ mutants, PCR products of respective sizes were cloned into pCR3.1 vector, followed by sequence verification by dideoxy sequencing. N-terminally-FLAG-tagged-human-ESR2 full-length plasmid was used. HA-tagged ESR2 full-length expression vector was generated by cloning HA-tagged human ESR2 cDNA into the pLVX-Tight-PuroTet-regulated vector (Clontech). The vector was constructed via a PCR approach using high-fidelity reverse transcriptase, Accuscript™ (Agilent Technologies; 600180), high-fidelity thermostable polymerase, Phusion™ (New England Biolab, F-530), and specific primers (Table 1) that were designed to amplify the full length sequence of human ESR2 (NM_001437). A 2×HA-tag-encoding sequence (1×=YPYDVPDYA) (SEQ ID NO: 33) was incorporated into the reverse primer to add a C-terminal tag. Total RNA isolated from MCF-7 cells was used as template for the PCR reaction. The amplified PCR products were cloned into the NotI and MluI sites of pLVX-Tight-Puro Vector. The integrity of the selected clone was verified by sequencing.

Transient transfections. For transient transfection of plasmid constructs, Xtremegene 9 (Roche) was used, as per the manufacturer's instructions. Cells were harvested 48 hours post-transfection for analysis. Empty vectors corresponding to the transfected cDNA expression plasmids were used as controls.

Generation of inducible ESR2 shRNA stable cells. The SMART inducible lentiviral shRNA VECTOR was transduced into MCF-7 and MDA-MB-231 cells as per the manufacturer's protocol (Dharmacon, USA). Lentiviral Particles titrations were performed on MCF-7 and MDA-MB-231 cells with serial 3-fold dilutions of lentiviral particles (V3SH7675-01EG2100-SMART vector inducible Human ESR2 mCMV-TurboGFPshRNA, Dharmacon USA) with 4 μg/mL polybrene concentrations. Combination of three shRNA sequences (A+B+C=10 μl) was mixed with transduction medium. 25 μL volumes of each dilution were transfer to cells and incubated overnight (16-20 hours). After 20 hours, 75 μl DMEM (10% FBS) medium was added to cells without removing old medium. 1 μg/mL freshly dissolved doxycycline containing DMEM was added into cells after 24 hours and further incubated for 48 hours. Vector titer was determined based on the positive GFP population. Positive GFP cell population was further grown to get individual clones that were used for the final experiments. Sequence information for the three shRNAs used are as follows: SMART vector inducible Human ESR2 mCMV-TurboGFPshRNA

```
A.
                            (SEQ ID NO: 34)
TGCTGGGAATGCTGTAATT

B.
                            (SEQ ID NO: 35)
CAGCGCAGAAGTGAGCATC

C.
                            (SEQ ID NO: 36)
GGATATTCATGGTGGCTGT
```

RNA isolation, cDNA synthesis, semi-quantitative end-point PCR, and quantitative real time PCR (qRT-PCR) assays. Total cellular RNA was isolated using TRizol reagent (Invitrogen) as per the manufacturer's protocol and quantified using a Nanodrop 8000 spectrophotometer. Isolated RNA was treated with DNAse I (Amplification grade, Invitrogen) and used for cDNA synthesis. The first strand cDNA pool was synthesized using 1 µg of total RNA and BioRad's iScript™ cDNA synthesis kit (170-8891) in a 20 µl reaction volume. A portion of the first strand cDNA products (5-10%) were amplified using target-specific primers (for primer sequences see Table 1). For semi-quantitative analysis of relative transcript levels reactions were carried out using AccuPrime™ Taq DNA Polymerase system (Invitrogen, 12339-016) in BioRad's iCycler thermocycler for 20-30 cycles with the cycling parameters of: Initial denaturation, 94° C.×2 minutes, Denaturation, 94° C.×30 minutes, Annealing, 58° C.×45 minutes, Extension, 68° C.×45 minutes, Final extension, 72° C.×5 minutes. qRT-PCR was performed using either FastStart Universal SYBR Green mastermix (Roche) or iScript™ Reverse Transcription Supermix for RT-qPCR (BIO-RAD) in a 10 µl reaction in Applied Biosystem's ABI Prism 7300 Real time PCR machine. 50° C. for 15s (1 cycle); 95° C. for 10 min (1 cycle); 95° C. for 15 s, followed by 60° C. for 45s (35 cycles). Dissociation curves were used to confirm the detection of a single amplicon. Primer efficiencies were calculated from a dilution curve and determined to be with the acceptable range (90-110%). Data acquisition and analysis was carried out by ABI's 7000 system sequence detection software V1.4. The relative target levels were determined by the ΔΔCT method (Livak, K J, Schmittgen T D. Analysis of relative gene expression data using real-time quantitative PCR and the 2(−Delta C(T)) Method. Methods 2001; 25(4): 402-8), using β-actin mRNA as reference gene endogenous controls. All experimental and control groups were performed in biological and technical triplicates. Error bars are representative of standard deviation, as indicated in the figure legends. Statistical analyses were performed by two tailed student t-test using 'Graphpad Prism 7.0'.

Glutathione S-Transferase (GST) Pull-Down assay. The GST and wild type and mutant GST-ESR1 and GST-TP53 constructs were expressed in BL21 (DE3) pLySs bacteria (Stratagene) and immobilized on Glutathione-Sepharose 4B GST-tagged protein purification resin (GE Healthcare Biosciences, Piscataway, N.J.) as previously described (Liu, W., et al. J Biol Chem 2006; 281(15): 9837-40). Full length and truncated ESR2 proteins were in vitro translated and [$^{35}$S] methionine-labeled using TNT T$_7$ Quick coupled transcription translation system (Promega). [$^{35}$S]-labeled proteins were incubated with ~4 µg of GST (negative control) or GST proteins bound to sepharose beads in 500 µl of NENT buffer (20 mM Tris-HCl at pH 8.0, 100 mM NaCl, 1 mM EDTA, 0.5% NP-40 containing 0.5% non-fat dry milk) for 2 hours at 4° C. The beads were washed four times with NENT buffer and bound proteins eluted with SDS-sample buffer were separated by SDS-PAGE. The gels were fixed, dried and subjected to fluorography.

Co-Immunoprecipitation (Co-IP) assay. Cells were rinsed twice with phosphate-buffered saline (PBS) and lysed in NENT buffer (20 mM Tris-HCl at pH 8.0, 100 mM NaCl, 1 mM EDTA, 0.5% NP-40) for 30 min by end-over-end mixing at 4° C. cOmplete™ Protein inhibitor cocktail (Roche, 11873580001) or Halt protease inhibitor cocktail (ThermoFisher Scientific, 78420) and phosphatase inhibitors (1 mM sodium orthovanadate and 10 mM sodium fluoride) were included in the lysis and wash buffers. For Co-IP with TP53, extracts were cleared by centrifugation at 12,000 g for 15 min at 4° C. and further pre-cleared by rocking for 2 hours at 4° C. with agarose-conjugated mouse IgG (Santa Cruz Biotechnology). Precleared extract was immunoprecipitated with agarose conjugated anti-TP53 (DO-1AC; Santa Cruz Biotechnology) or equivalent amount of mouse IgG overnight at 4° C. The agarose beads containing bound proteins were washed three times with lysis buffer and boiled in SDS-sample buffer. For all other Co-IPs, the extracts were cleared by centrifugation for 10 min at 10,000 rpm at 4° C. and lysate was pre-cleared with Recombinant Protein G Agarose beads (Invitrogen, 15920-010) for 1 hour at 4° C. with rotation. 2.5 mg of pre-cleared lysate was immunoprecipitated with 5 µg of the indicated antibody or control IgG overnight at 4° C. with rotation. The antigen-antibody complexes were captured with protein G-Agarose beads for 3 h at 4° C. with rotation, washed 4 times in NENT buffer, eluted with SDS-PAGE sample buffer. Immunoprecipitated proteins were resolved by SDS-PAGE-western blotting, using the ECL Chemiluminescent method (ThermoFisher Scientific 32106).

Cell cycle analysis. Cells were subjected to cell cycle distribution analysis 48 hours post-transfection. Propidium iodide (PI) (Sigma Aldrich-P4170) was used for staining total cellular DNA. Flow cytometry was performed on a FACScan cytometer (Pharmingen), and the data were analyzed using ModFit software.

Apoptosis analysis. APC Annexin V (BD Pharmingen; 550474) and FITC Annexin V (Invitrogen V13242) kits were used for flow cytometric analysis of cells undergoing apoptosis. For analyzing effect of ESR2 knockdown, cells were transiently transfected with either ESR2 siRNA or non-specific (NS) siRNA for 48 hours. In the case of cells stably expressing ESR2shRNA, cells were treated with or without doxycycline for 48 hours to induce shRNA expression. For overexpression of ESR2, cells were transiently transfected with FLAG-ESR2 for 48 hours. Cells were subsequently washed with PBS followed by Annexin and PI staining as per manufacturer protocol. Stained cells were analyzed by FACS Calibur flow cytometer and CellQuest Pro software (BD Bioscience) and Winlist3D 8.0.

Clonogenic growth assay. 48 hours post-transfection, approximately 2000 cells/cm$^2$ were seeded and allowed to grow for 8-10 days. At this point, cells were fixed with 10% formaldehyde solution for 15 minutes at room temperature. Subsequently, cells were stained with 0.1% crystal violet solution for 15 minutes at room temperature. Unabsorbed crystal violet dye was washed away by submerging the plate several times in running water. Plates were completely air dried at ambient temperature for several hours and photographed. For quantitation purposes, the absorbed dye, which is proportional to cell mass, was extracted with 10% acetic acid solution. 100 µl of extract per sample was loaded into 96-well plates, and the absorbance at 595 nm was measured using a Synergy 2 (BioTek) plate reader.

Chromatin immunoprecipitation (ChIP) assay. ChIP assay was carried out as previously described (Liu W, et al. PLoS One 2011; 6(12):e29466). Briefly, cells were fixed with 1.5% Formaldehyde for 10 minutes at 37° C. Cell lysis was done using 1 ml ChIPlysis buffer per $5 \times 10^6$ cells. Chromatin shearing was carried out in batch using cup-horn attachment in MisonixSonicator 3000 (Misonix, NY) set at medium power for total of 20 minutes (intermittent pulses of 10 seconds ON 20 seconds OFF). Chromatin fragments equivalent of $1-2 \times 10^6$ cells and 2.5-5 µg of either species matched control-IgG or specific primary antibody was used per ChIP reaction. Chromatin-bound protein-antibody complex was harvested using Protein-A-agarose/salmon sperm DNA (Millipore; 16457). Immunoprecipitated chromatin samples were analyzed through real-time q-PCR as stated above. A region downstream of CDKN1A/p21 promoter sequence was used as endogenous control for the relative quantitation of immunoprecipitated chromatin fragments (Details of the primers are provided in Table 1). The promoter occupancy by transcription factor (s) of interest was analyzed as qRT-PCR.

Proximity ligation assay (PLA). In situ PLA was carried out using the Duolink II reagent kit (Olink Bioscience) and supplier's protocol. Briefly, 10,000 cells were seeded on 12 mm coverslips (Thermo Fisher Scientific) in 24-well plates. After 12-24 h, cells were fixed with freshly prepared 2% paraformaldehyde (Sigma) solution in PBS, pH 7.4 at room temperature for 20 minutes. Subsequently, the coverslips were washed twice with 1 ml of PBS, blocked and permeabilized with a solution containing 2% BSA and 0.1% Triton-X-100 in PBS, pH 7.4, for 1 hour at room temperature, followed by nuclear permeabilization using a buffer containing 1% BSA and 0.1% NP40 in PBS, pH 7.4, for 15 minutes at room temperature. Mouse and rabbit primary antibodies were diluted appropriately in antibody dilution buffer (supplied in the kit) and were applied to the coverslips in an open droplet manner and incubated at room temperature for 1 hour in a humidified chamber. The remainder of the protocol, which included secondary probe hybridization, ligation, and amplification, were carried out as per the manufacturer's instructions. Coverslips were mounted with the supplied mounting media containing DAPI. Photographs were taken with an AXIOSKOP (Carl Zeiss, Germany) fluorescent microscope fitted with a Hamamatsu 3CCD digital camera and ImagePro Plus Software. Subsequently, Blob-Finder image analysis software (developed by Centre for Image Analysis, Uppsala University) was used to quantify the PLA signals.

For PLA on archived TNBC tissue, a harmonized antigen retrieval protocol for both TP53 and ESR2 (determined by immunohistochemistry with TP53 antibody FL393 and ESR2 antibody, MC10) was developed. Antigen retrieval was conducted for 40 minutes in steamer with EDTA buffer followed by a 20 minute cooling at ambient temperature. Endogenous peroxidase was quenched with aqueous 3% $H_2O_2$ for 10 minutes and washed with PBS/T. Serum free protein block (Dako) was applied for 5 minutes. Primary antibodies for TP53 and ESR2 were added and incubated at room temp for one hour followed by washing with PBS/T. Rest of the PLA protocol and image analysis were as described above.

Generation of TP53 knockout cells using CRISPR/Cas9. Mutant TP53 knockout (MDA-MB-231-TP53KO) cells were generated in collaboration with the Genome Engineering and iPSC center at Washington University School of Medicine. MDA-MB-231-LM2.4$^{Luc+}$ cells were nucleofected with Cas9 and a TP53-specific sgRNA (5'-

TCCTCAGCATCTTATCCGAGNGG-3') (SEQ ID NO: 37). Cells were single cell-sorted and genomic DNA was extracted. DNA was amplified using the following forward and reverse primers: 5'-CCATGAGCGCTGCTCAGAT-3' (SEQ ID NO: 38) and 5'-TCATGGGGTTATAGG-GAGGTCA-3' (SEQ ID NO: 39). Clones were screened for frameshifts by sequencing the target region with Illumina-MiSeq at approximately 500× coverage. After genomic screening, two clones which showed indels resulting in a frameshift mutation were additionally screened for mutant TP53 protein, confirming a complete knock out of mutant TP53 in both clones. One clone was selected to be used in the current experiments. Lack of TP53 protein expression was confirmed by immunoblotting.

Immunohistochemical Staining and Scoring of the Human Breast Cancer Tissue Micro Array (TMA).

TMA Construction: Three 1-millimeter tissue cores from each formalin-fixed paraffin embedded donor blocks were precisely arrayed into a new recipient paraffin block that included tumor specimens and controls. Eligible patients had surgeries performed between 1995 and 2008 at Roswell Park Comprehensive Cancer Center (Roswell) Buffalo, N.Y. Specimens for controls within the TMA consisted of multiple cores of normal tissue from 10 different organs including heart, colon, kidney, adrenal, ovary, myometrium, brain, thyroid, lung, and prostate thereby representing more than 20% of all the cores in a TMA. Appropriate Institutional Review Board approval consistent with federal, state and local requirements was obtained for this project and clinical and outcome data was de-identified.

Immunohistochemistry (IHC): For antigen retrieval slides containing serial sections of triple negative breast cancer (TNBC) TMA were heat-treated and endogenous peroxidase was quenched with aqueous 3% $H_2O_2$ for 10 minutes. Slides were then loaded on a Dako autostainer where they were treated with serum free protein block (DAKO, cat #X0909) for 5 minutes followed by reaction with primary antibodies against TP53 (FL-293 or CM1) and ESR2 (14C8) for one hour. Secondary antibodies, HRP-conjugated anti-rabbit (DAKO, cat #K4003) and anti-mouse (Leica, cat #PV-6114) were used for 30 minutes. Slides were developed by the DAB chromagen (DAKO, cat #K3468) for 10 minutes and finally, counterstained with hematoxylin, dehydrated, cleared and cover-slipped.

Aperio Slide Scanning and Image Analysis: TMA slides were digitally scanned using AperioScanscope (Aperio Technologies, Inc., Vista, Calif.) with 20× bright-field microscopy. These images are then accessible using Spectrum (Aperio Technologies, Inc., Vista, Calif.), a web-based digital pathology information management system. Slide images are automatically associated to a digital slide created in the Digital Slide table in Spectrum. Once slides are scanned, Aperio Image Scope version 11.2.0.780 (Aperio Technologies, Inc., Vista, Calif.) was used to view images for image analysis. Slide image data field were populated, images were examined for quality and were amended as necessary. An annotation layer was created for each core of interest in the TMA. Invasive tumor cell□only regions were identified and annotated to appropriately represent the heterogeneity of staining of each TMA core for image analysis. Care was taken to avoid including areas of carcinoma in situ and regions with staining artifacts. When possible, representative areas of tumor were selected for analysis with a minimum target of 30 cells per TMA core. Areas of target cells for image analysis were circled using the free form pen tool and areas to be excluded were marked using the negative free form pen to reduce cells irrelevant regions from image analysis calculations. Image analysis data was exported from Spectrum as a tab delimited .csv file and converted to a .xls file and formatted using Microsoft Excel 2010.

Quantitative scoring of nuclear ESR2 and TP53 Immunohistochemistry signals: The nuclear segmentation factor parameter was set to account for brown stain in the nuclear compartment and the nuclear threshold type was set to adaptive, in which allows the algorithm to adjust thresholds based on the strength of the staining. The Nuclear Algorithm detects the positive (DAB) nuclear staining for the individual tumor cells and quantifies their staining intensity. Cell nuclei are individually classified as 0—none, 1+—weak, 2+—moderate, and 3+—strong. The algorithm uses color de☐convolution that separates the hematoxylin and DAB stains, thereby providing stain separation. The analysis results provided the total number of detected cells, the percentage of cells per class (0, 1+, 2+ and 3+) and the percentage of positive stained cells along with the average staining intensity of the positive nuclei as a score of 0, 1+, 2+ and 3+. The H-score score equals=1*(%1+)+2*(%2+)+3*(%3+) with the score is between 0 and 300, where 300 represents 100% of cells being 3+. The counterstain hematoxylin, a blue stain, was applied for morphologic detail of the surrounding tissue to help identify nuclear and cytoplasmic compartments of cells for analysis.

Statistical analyses: Statistical analyses of experiments in cell models: Statistical analyses were performed using the two-tailed Student's t-test comparisons of relative gene expression, cell growth, cell cycle and apoptosis assays. p values less than 0.05 were deemed statistically significant throughout, with no adjustment for multiplicity.

Statistical analysis of METABRIC (Molecular Taxonomy of Breast Cancer International Consortium) data: All statistical analyses for determining clinical significance ESR2/TP53 combination in METABRIC were performed using WinSTAT (http://www.winstat.com/). Breast cancer-specific survival (BCSS), defined as the time of diagnosis to the time of a breast cancer-related death was used for the survival analyses, and statistical significance was tested using Univariate cox analysis (Table 4). For analyzing the Roswell cohort of TNBC patient tumors, differences in clinical characteristics between the expression classes were tested using Fisher's Exact and Wilcoxon Rank Sum tests as appropriate. All P values are two sided and are interpreted as described in 2016 ASA P Value Statement. Statistical significance of comparison of relative gene expression, cell growth, cell cycle and apoptosis assays were determined by two-tailed Student's t-test. p values less than 0.05 were deemed statistically significant throughout, with no adjustment for multiplicity.

Statistical analysis of TMA data: Up to three tissue samples per patient were obtained from three separate Tissue Micro Arrays. Marker expression levels in the samples were obtained as described above. Sample records with no cells staining positive were considered to contain no tumor tissue and were excluded from the analysis. Sample-level expression was quantified as the H-Score, the weighted arithmetic mean of the intensity level [0,1,2&3] in the sample, weighted by the percentage of cells at each intensity. Patient-level expression was quantified as the arithmetic mean of the available sample-level scores. The High/Low expression classification was determined by the median of the observed patient-level H-Scores. Differences in clinical characteristics between the expression classes were tested using Fisher's Exact and Wilcoxon Rank Sum tests as appropriate. Overall Survival (OS) was defined as the number of months between diagnosis and death from any cause. Progression Free Survival (PFS) was defined a time from diagnoses to documentation of disease progression or death, whichever came first. Patients with no event were censored at the date of last follow up. Differences in OS and PFS between the expression classes were tested with a log rank test and displayed using Kaplan-Meier plots. Median follow up time was about 77 months, estimated by the Reverse Kaplan Meier method (Shuster J J. Median follow-up in clinical trials. J Clin Oncol 1991, 9(1):191-2; Schemper M, Smith T L. A note on quantifying follow-up in studies of failure time. Control Clin Trials 1996, 17(4):343-6). All P values are two sided and are interpreted as described in 2016 ASA P Value Statement. (Wasserstein R L, Lazar Na. The ASA's statement on p-Values: Context, process, and purpose. The American Statistician 2016; 70(2):129-133). P values less than 0.05 were deemed statistically significant throughout, with no adjustment for multiplicity.

Samples were first stratified at the median TP53 Nuclear H Score. Within the TP53 groups, the samples were further stratified at the median ESR2 Nuclear H-Score, as shown in Tables 3 and 4 below.

TABLE 3

Tumor size: TP53-high (surrogate for mutant TP53) breast cancer patients stratified at the median ESR2 nuclear H-Score.

| | ESR2 H Score | | |
| Size | Low | High | All |
| --- | --- | --- | --- |
| N | 12 | 11 | 23 |
| mean | 3.71 | 1.80 | 2.80 |
| Std | 2.61 | 0.46 | 2.11 |
| Med | 2.80 | 1.60 | 2.00 |
| Min | 1.50 | 1.30 | 1.30 |
| Max | 11.00 | 3.00 | 11.00 |

TABLE 4

Tumor stage: TP53-high (surrogate for mutant TP53) breast cancer patients stratified at the median ESR2 nuclear H-Score

| | ESR2 H Score | | | | | |
| | Low | | High | | All | |
| Stage | n = | % | n = | % | n = | % |
| --- | --- | --- | --- | --- | --- | --- |
| 1 | 1 | 8.33 | 9 | 81.82 | 10 | 43.48 |
| 2 | 10 | 83.33 | 2 | 18.18 | 12 | 52.17 |
| 3 | 1 | 8.33 | . | . | 1 | 4.35 |

Results

Direct Interaction of ESR2 with Both WT and Mutant TP53

This example has demonstrated that ESR2 binds directly to TP53. PLA showed that ESR2 is in complex with WT TP53 in situ in MCF-7, ZR-75-1 (luminal breast cancer cells), and CAL-51 (TNBC cells) (FIGS. 1A-C) as well as with mutant TP53 in MDA-MB-231, MDA-MB-468 (TNBC cells), and SK-BR-3 (HER2-overexpressing cells) (FIGS. 1D-F), and T-47D (luminal breast cancer cells) (FIG. 9A). Such interaction was considerably reduced when ESR2 was silenced (FIGS. 1A-F, right panels; FIG. 9B-C). In MCF-7, MDA-MB-231, and SK-BR-3 cells transfected with FLAG-ESR2, PLA signals were specifically localized to the cells expressing FLAG-ESR2 (FIGS. 10A-C). Co-immuno-precipitation assays further confirmed the specific interaction of endogenous mutant and WT TP53 with the endogenous ESR2 and the exogenously expressed FLAG-ESR2 (FIGS. 1G-K). FIG. 19A shows quantification of PLA data in FIGS. 1A-M.

Figure 20:
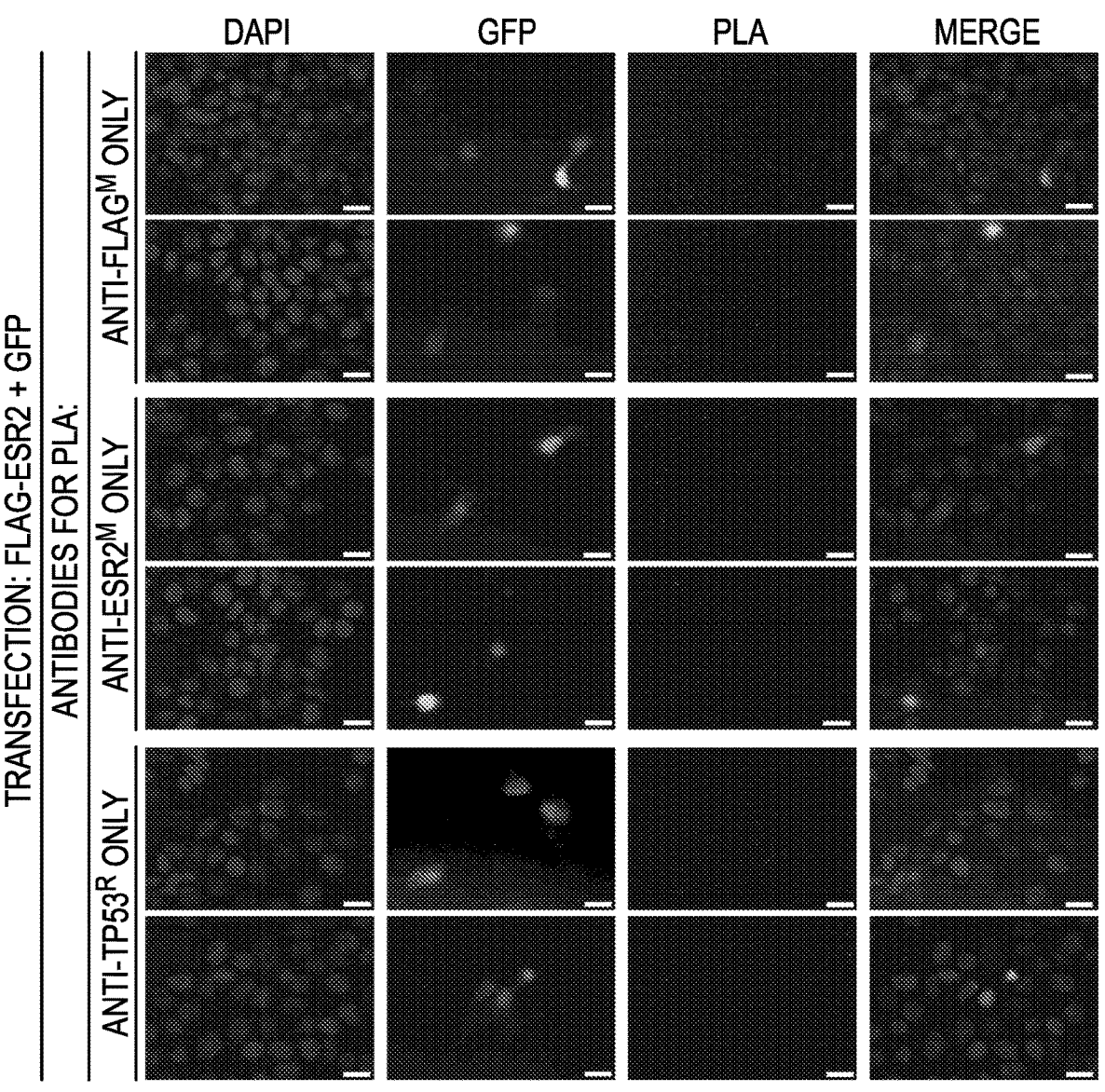

FIG. 20 shows the negative control PLA with single primary antibodies. PLA was performed with single primary antibodies (anti-FLAG, anti-ESR2 (MC10), and anti-TP53 (FL393) in MCF-7 cells co-transfected with either an empty vector or FLAG-ESR2 plasmid along with $1110^{th}$ amount of a GFP expression construct (pBabe-eGFP). Two sets of images are provided for each condition. DAPI was used as a nuclear stain. Antibodies used for PLA and the plasmids transfected are shown on the left side.

Reciprocal cell-free GST-pull down assays showed that the region of ESR2 containing the C and D domains (amino acid residues: 149-248) was necessary and sufficient to bind to TP53, whereas the C-terminal regulatory domain of TP53 (amino acid residues: 361-393) was the minimal region required for interaction with ESR2 (FIGS. 1L-M, and FIGS. 11A-E). Collectively, these protein-protein interaction data demonstrate that ESR2 and TP53 are found in one complex and are capable of binding directly to one another.

Figure 2A:
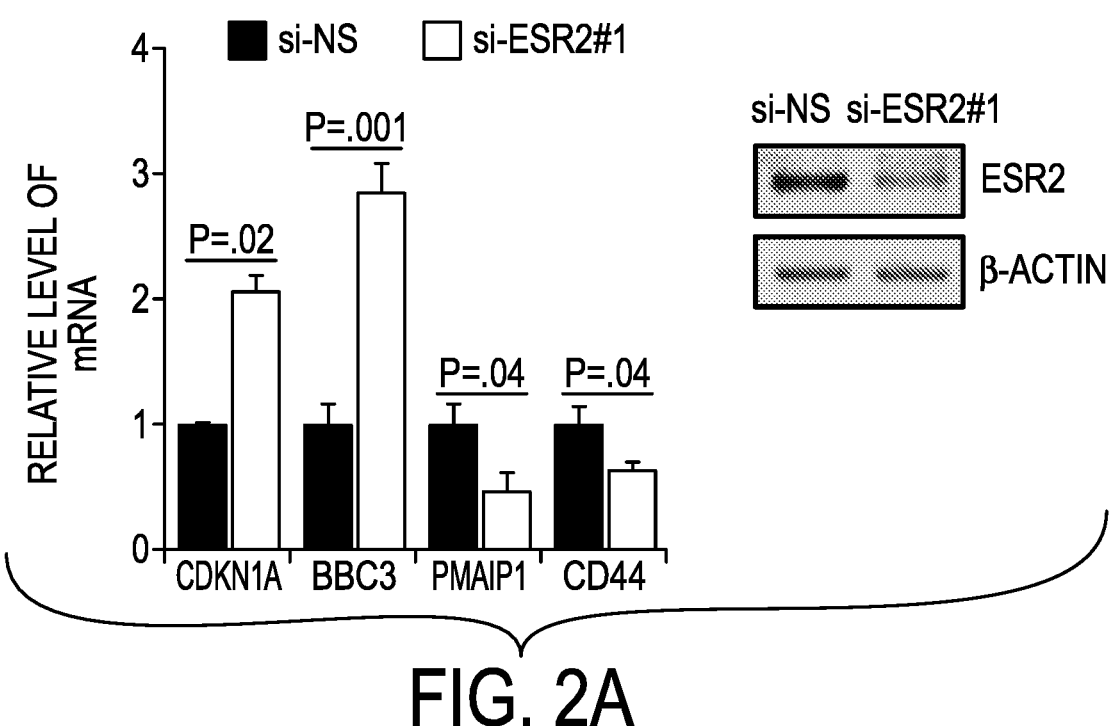
Figure 2B:
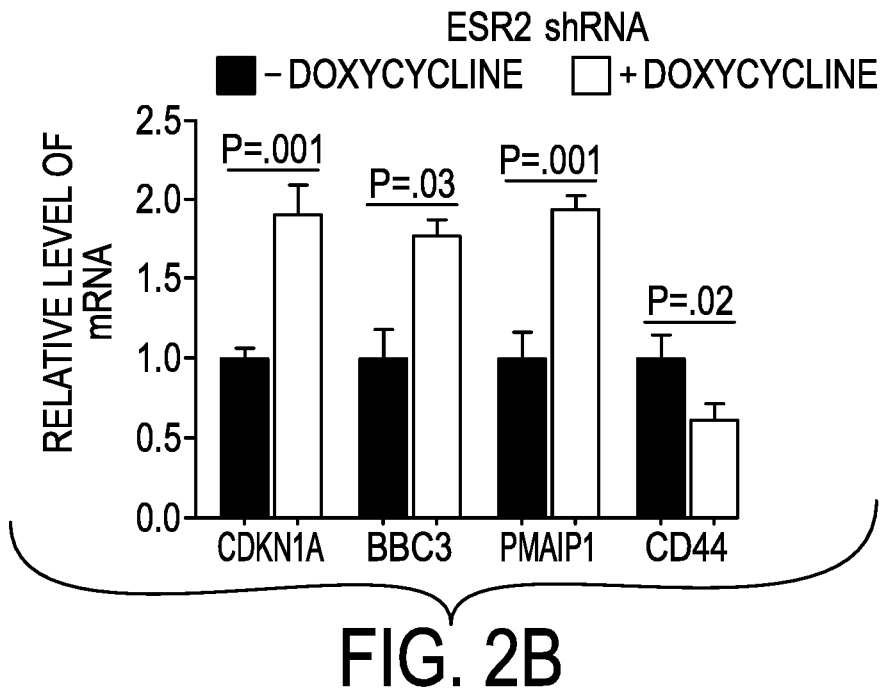
Figure 2C:
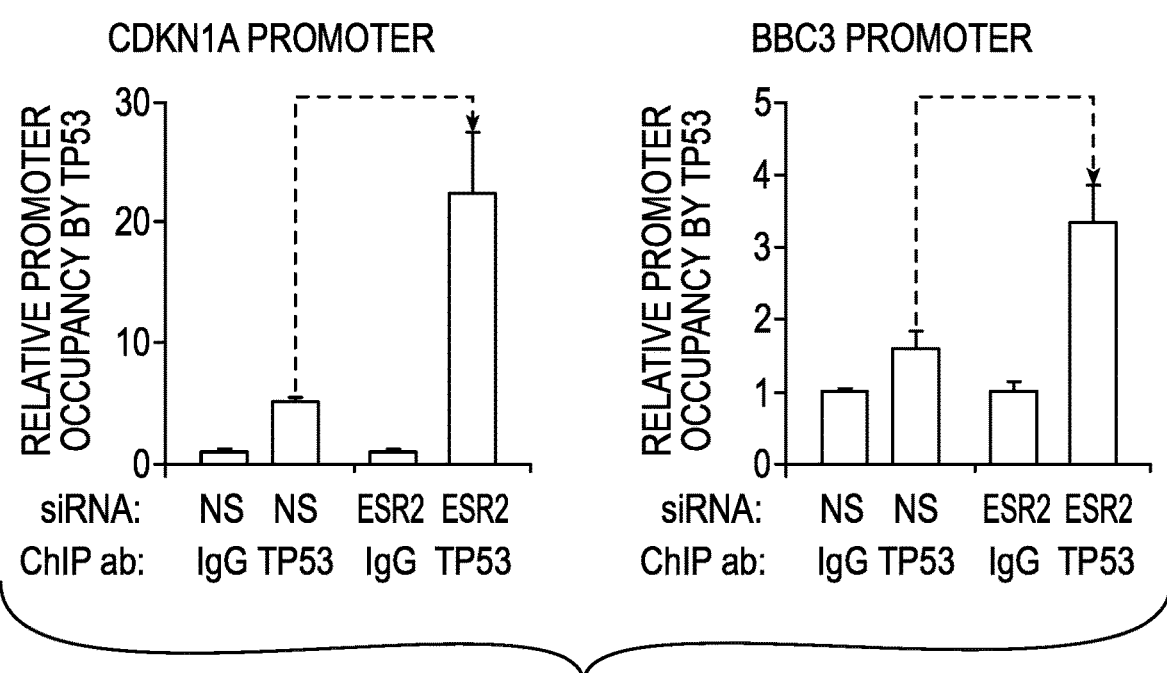
Figure 2D:
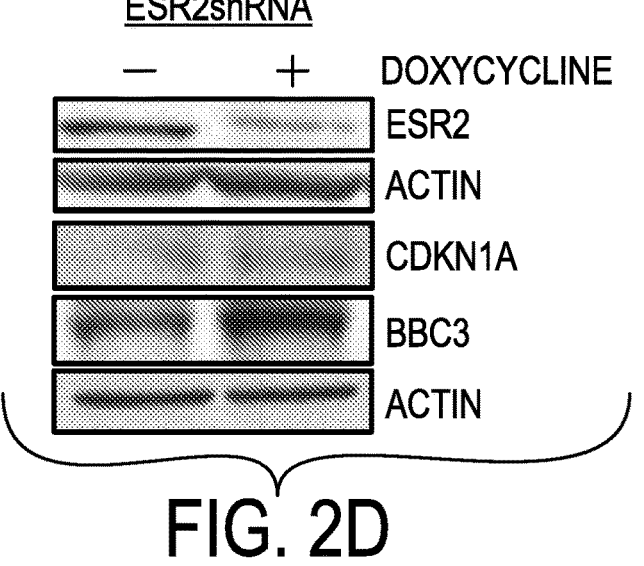
Figure 2E:
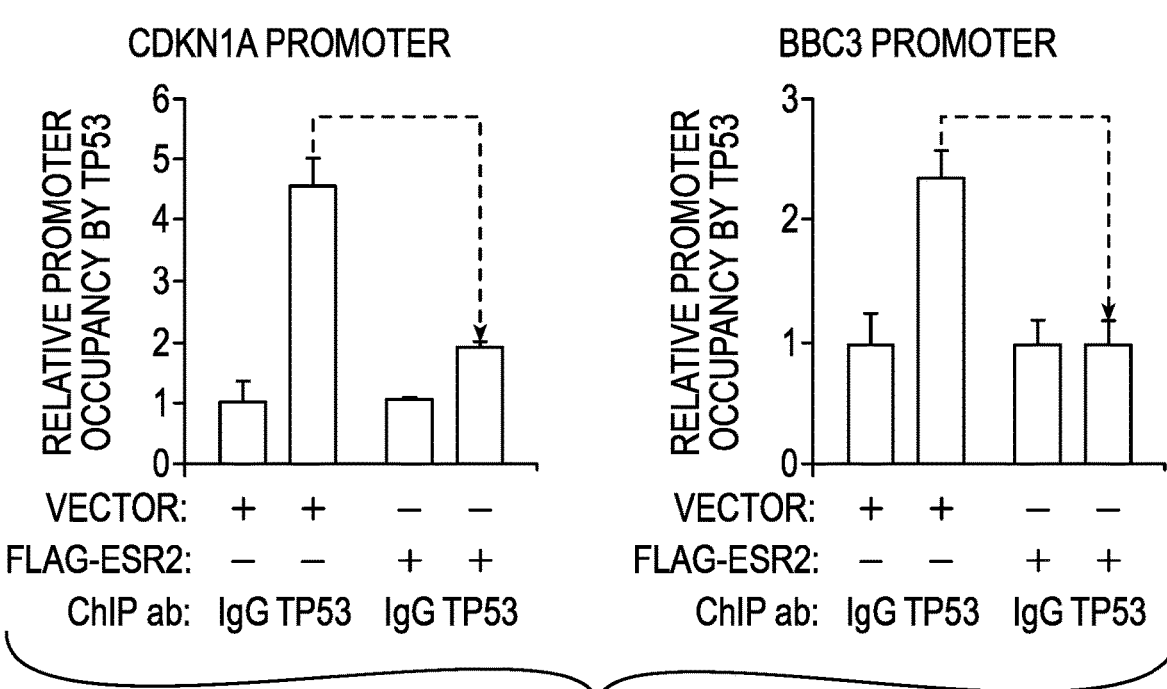
Figure 2F:
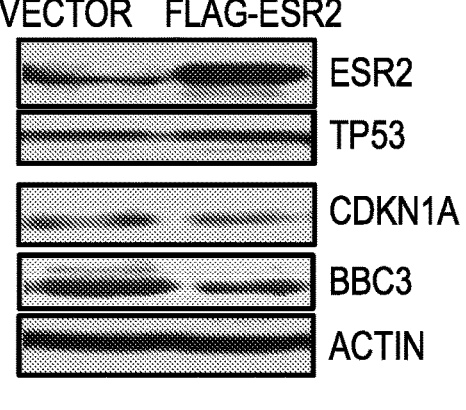

Effect of ESR2 on TP53-Target Gene Expression and Cell Proliferation in the WT TP53 Context It was tested whether the direct protein-protein interaction between ESR2 and WT TP53 might inhibit TP53's function as a transcriptional regulator. First, it was confirmed with qRT-PCR and immunoblotting that ESR2 is expressed in measurable levels in multiple BC cell lines expressing either WT TP53 or mutant TP53 and can be reproducibly knocked down with multiple RNAi approaches and overexpressed (FIGS. 12A-E). Upon silencing ESR2 expression in MCF-7 cells, the mRNA levels of CDKN1A (p21), BBC3 (PUMA), and PMAIP1 (NOXA), (genes activated by TP53) were induced, while the levels of CD44 (gene repressed by TP53) mRNA were reduced (FIGS. 2A-B). Similar data were obtained in ZR-75-1, another luminal BC cell line expressing WT TP53 (FIGS. 2G, H). Opposite effects on transcript levels were observed when ESR2 was overexpressed in these cells (FIGS. 2F, I, J). These data show that endogenous ESR2 is capable of blocking both the transcriptional activation and repression by TP53.

qChIP assays showed that knocking down of ESR2 in MCF-7 cells resulted in enhanced TP53 recruitment to CDKN1A and BBC3 promoters (FIG. 2C) resulting in their increased expression (FIG. 2D). On the contrary, there was 3 to 4-fold reduction in TP53 recruitment to these promoters following overexpression of FLAG-tagged-ESR2 or HA-tagged ESR2 (FIG. 2E and FIG. 13A, respectively) and concomitant reduction in CDKN1A and BBC3 protein levels (FIG. 2F).

Figures 3A, 3B:
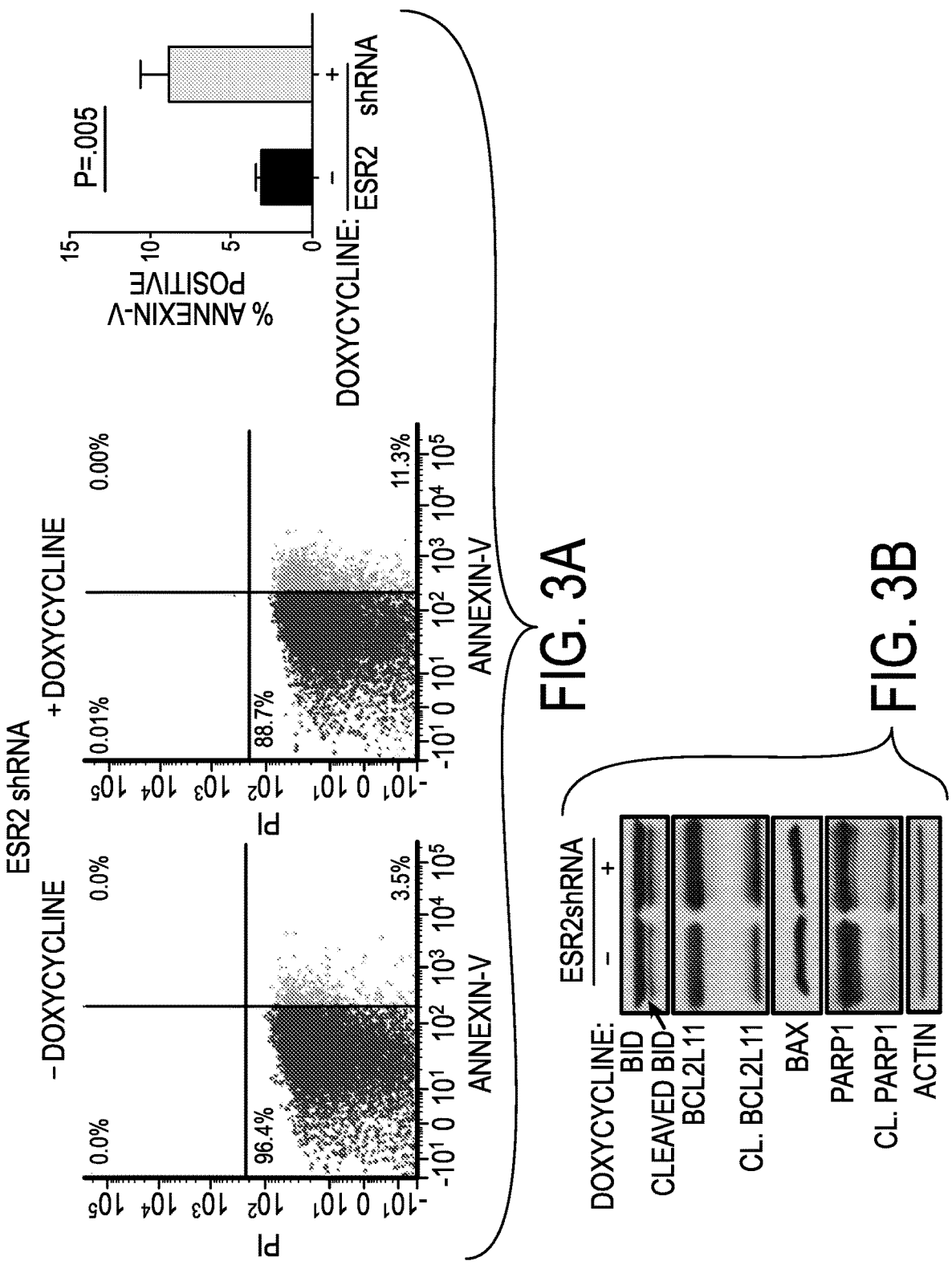
FIGS. 3A-H. Effect of ESR2 on cell proliferation in the WT TP53 context. A) Apoptosis in MCF7shESR2 stable cells treated with or without 1 µg/ml doxycycline (to induce ESR2 shRNA) for 48 hours was analyzed by flow cytometry after double-staining with Annexin V-FITC and PI. Bar graph (right panel) shows fold change of Annexin+/PI-cells. B) Expression of active apoptosis markers: cleaved BID, cleaved BCL2L11, BAX, and cleaved PARP1 proteins in MCF-7ESR2 shRNA stable cells with or without 1 µg/ml doxycycline for 48 hours to induce ESR2 shRNA expression was analyzed by immunoblotting. C) Apoptosis in ZR-75-1 cells following ESR2 #2 siRNA knockdown for 48 hours was analyzed by flow cytometry after double-staining the cells with Annexin V-FITC and PI. Bar graph (far right panel) shows fold change of Annexin+/PI-cells. D) Expression of active apoptosis markers: cleaved BID, cleaved BIM, BAX, and cleaved PARP proteins in ZR-75-1 with or without ESR2 #2 siRNA knockdown for 48 hours was analyzed by immunoblotting. E) Quantification of flow cytometry analysis of MCF-7 cells stained with PI for cell cycle distribution, with or without knockdown with ESR2 #1siRNA for 48 hours. F) Quantification of flow cytometry analysis of CAL-51 cells stained with PI for cell cycle distribution, with or without knockdown with ESR2 #2 siRNA for 48 hours was performed. G) MCF-7 cells with or without knockdown with ESR2 #1 siRNA were subjected to clonogenic assay. Top panel: bar graph shows quantification of average absorbance of three independent experiments. Bottom panel: representative image of colonies stained with crystal violet are shown. H) A model for the pro-tumorigenic role of ESR2 in the WT TP53 setting is shown. Showing two prototypic TP53-targets, CDKN1A and BBC3 does not imply these are the only proteins participating in the ESR2-TP53 signaling crosstalk. All 'p' values were determined by two-tailed Student's t-test. Error bars represent standard deviation (SD). si-NS=non-specific siRNA; siESR2=ESR2-specific siRNA; PI=Propidium Iodide; Cl. BCL2L11=Cleaved BCL2L11.
Figures 3C, 3D:
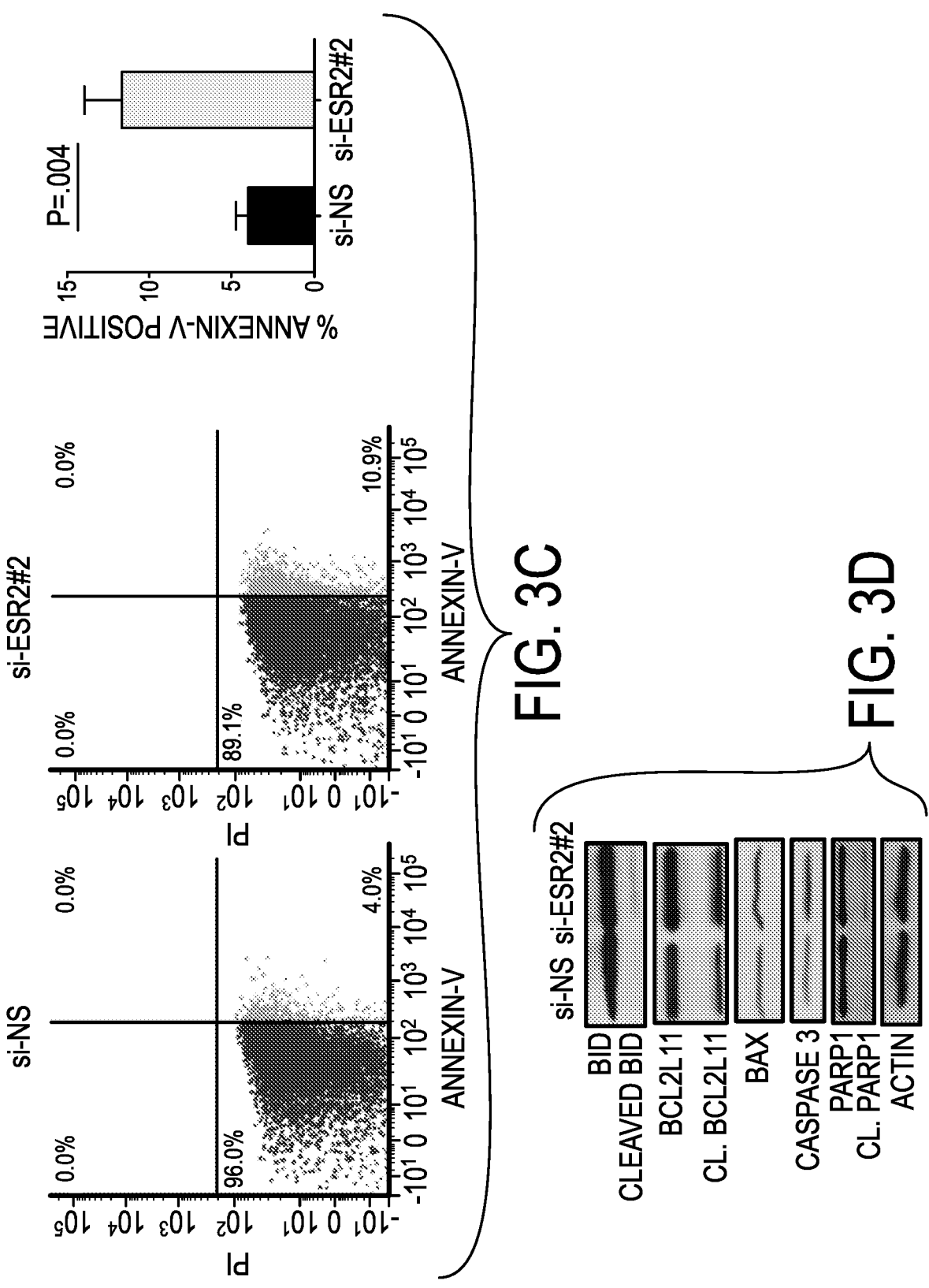

Consistent with the repressive effect of ESR2 on TP53 transcriptional targets, induction of ESR2 knockdown resulted in increased apoptosis in MCF-7 compared to control cells (FIG. 3A) and pro-apoptotic proteins such as BAX, un-cleaved and cleaved BID, BCL2L11/BIM, and cleaved poly (ADP-ribose) polymerase (PARP1) were increased (FIG. 3B). Similar results were obtained with ZR-75-1 cells (FIGS. 3C-D).

Figure 3E:
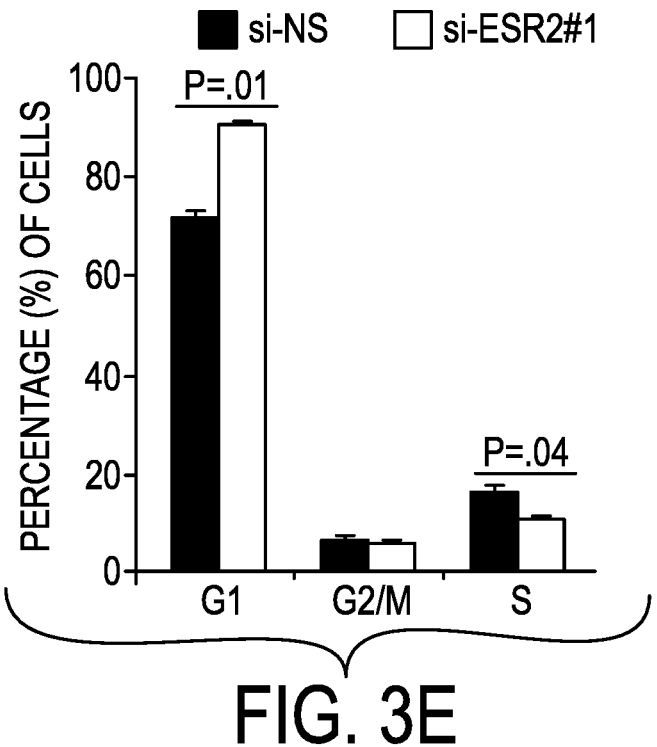
Figure 3F:
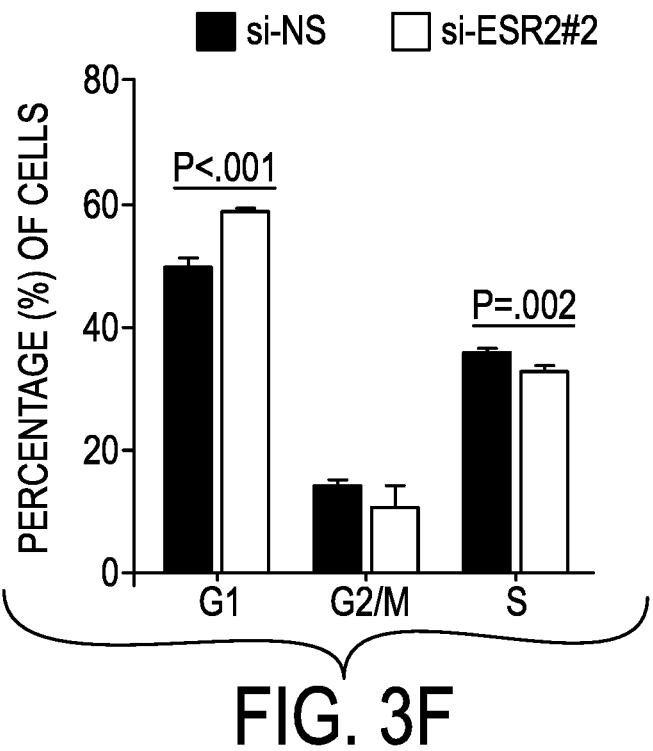
Figure 3G:
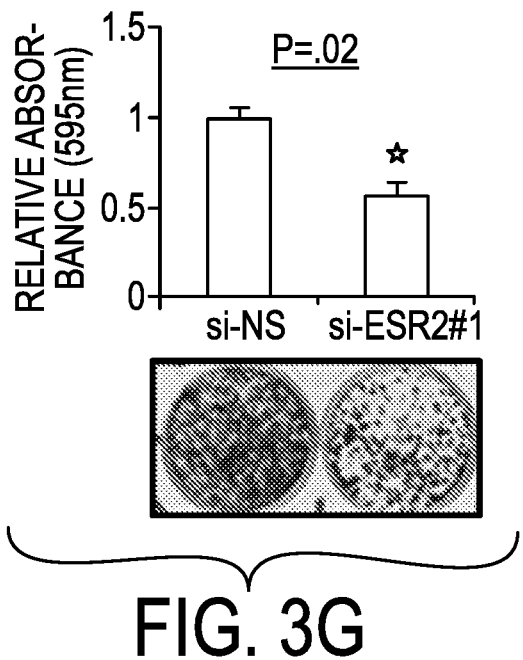
Figure 3H:
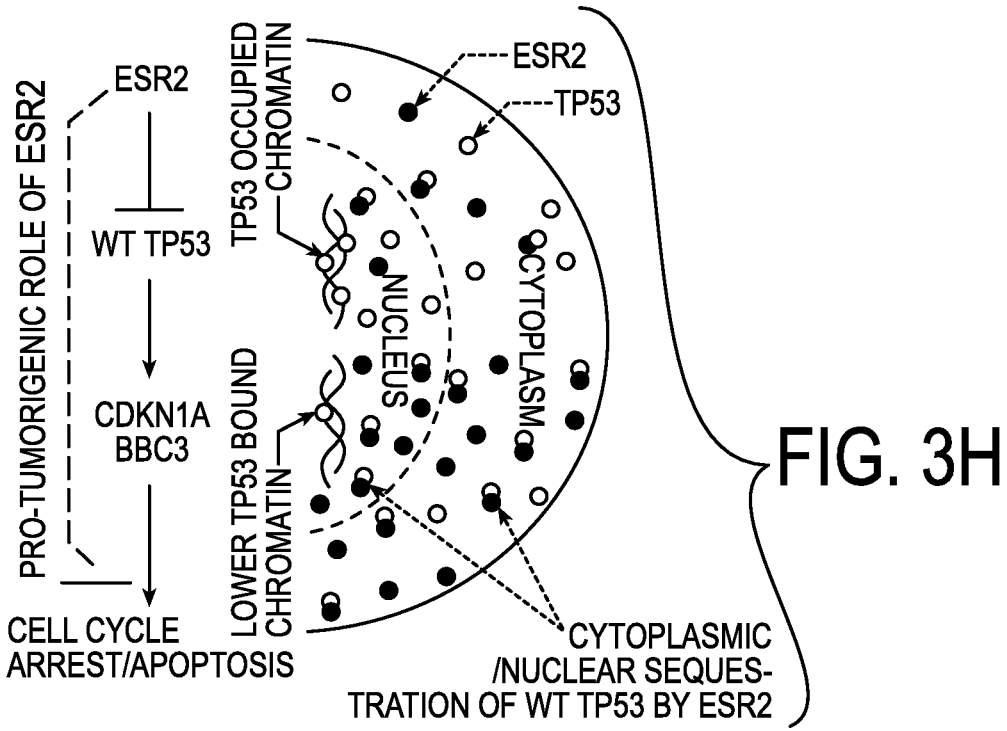

Furthermore, cell cycle arrest in the G1-phase was increased whereas the S-phase was decreased when ESR2 expression was silenced in MCF-7 and CAL-51 (FIGS. 3E-F). Colony formation assays showed that cell proliferation was considerably reduced in ESR2-knocked down cells (FIG. 3G). Collectively, these data show that ESR2 has a pro-proliferative effect in BC cells expressing WT TP53 (FIG. 3H).

Figure 4A:
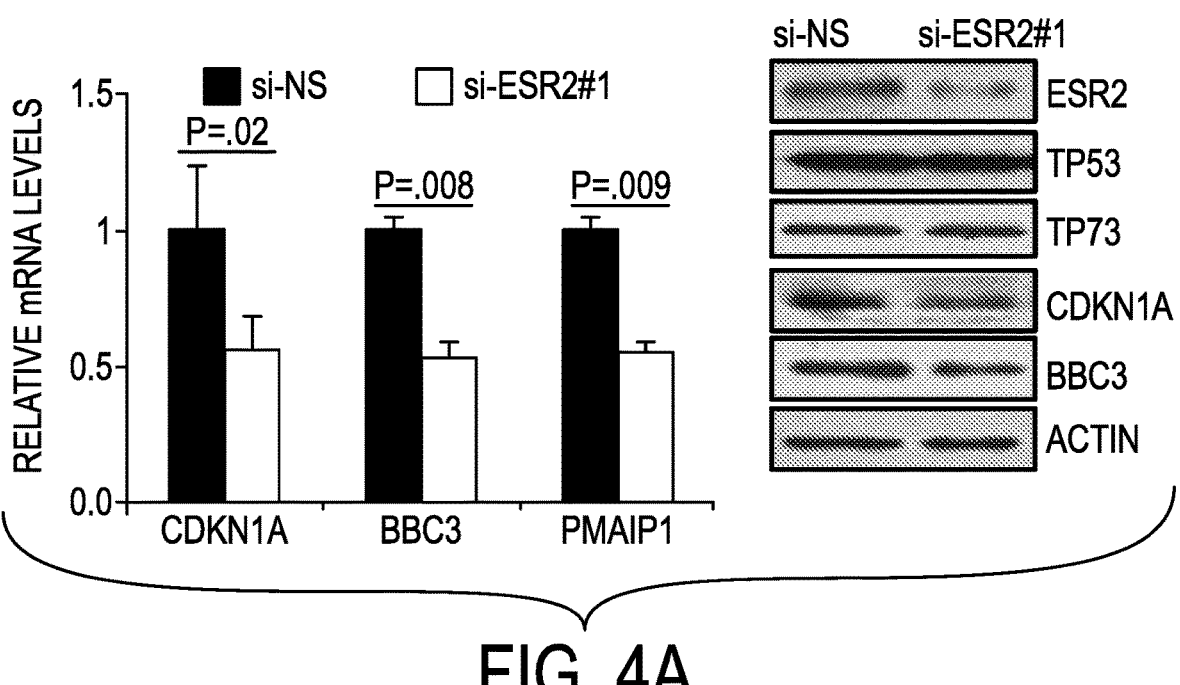
FIGS. 4A-H. Effect of ESR2 on cell proliferation in the mutant TP53 context. A) TP53 target gene expression in MDA-MB-231 cells with or without knocking down ESR2 with ESR2 siRNA #1 for 48 hours was determined by qRT-PCR. Right panel: Expression of ESR2, TP53, TP73, CDKN1A, and BBC3 proteins in MDA-MB-231 cells post-ESR2 knockdown with siRNA #1 for 48 hours was analyzed by immunoblotting. B) TP53 target gene expression in MDA-MB-231ESR2shRNA cells treated with or without 1 µg/ml doxycycline for 48 hours to induce ESR2shRNA expression was determined by qRT-PCR. C) MDA-MB-231 cells with or without knocking down ESR2 with siRNA #2 for 48 hours were double-stained with Annexin V-FITC and PI for flow cytometry analysis of apoptosis. Right panel: Quantification of flow cytometry analysis of MDA-MB-231 cells with or without knocking down ESR2 with siRNA for 48 hours. D) MDA-MB-231 cells with or without ESR2 knockdown with ESR2siRNA #1 for 48 hours were stained with PI for analyzing cell cycle with flow cytometry. E) TP53-target gene expression in MDA-MB-468 cells with or without ESR2 knockdown with ESR2 siRNA #2 for 48 hours was determined by qRT-PCR. F) MDA-MB-468 cells with or without knocking down ESR2 with siRNA #2 for 48 hours were double-stained with Annexin V-FITC and PI for assaying apoptosis by flow cytometry. Bar graph (far right panel) shows fold change of Annexin+/PI-cells. G) TP53-target gene expression in SK-BR-3 cells with or without ESR2 knockdown with ESR2 siRNA #2 for 48 hours was determined by qRT-PCR. Right panel: Expression of ESR2, p21, and PUMA proteins in SK-BR-3 cells with or without knocking down ESR2 with siRNA #2 for 48 hours was analyzed by immunoblotting. H) TP53-target gene expression in T-47D cells with or without ESR2 knockdown with ESR2 siRNA #2 for 48 hours was determined by qRT-PCR. Right panel: Expression of ESR2, CDKN1A, and BBC3 proteins in T-47D cells with or without knocking down ESR2 with siRNA #2 for 48 hours was analyzed by immunoblotting. All 'p' values were determined by two-tailed Student's t-test. Error bars represent standard deviation (SD). siESR2=ESR2-specific siRNA; qRT-PCR=quantitative real time PCR. PI=Propidium Iodide.
Figure 4B:
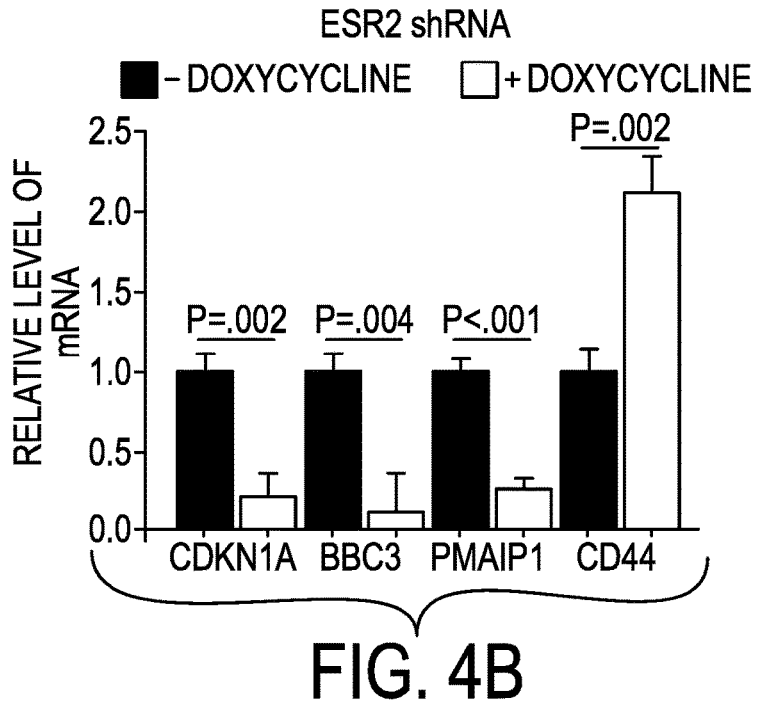
Figure 4C:
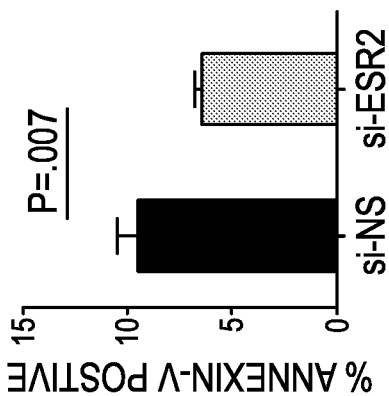
Figure 4C:
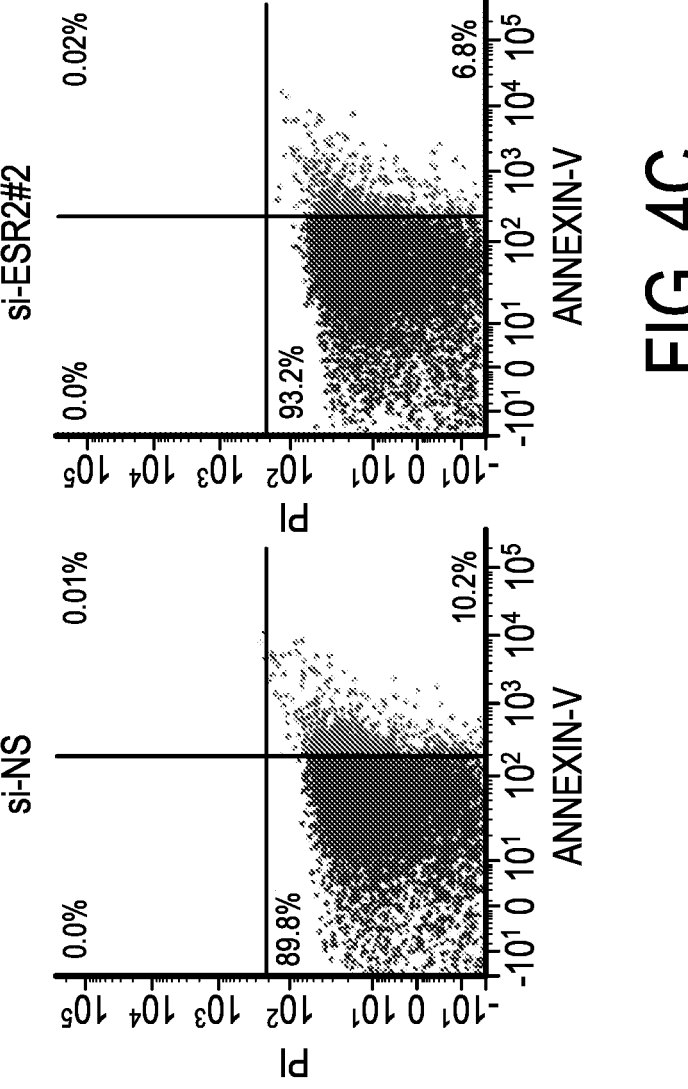
Figure 4D:
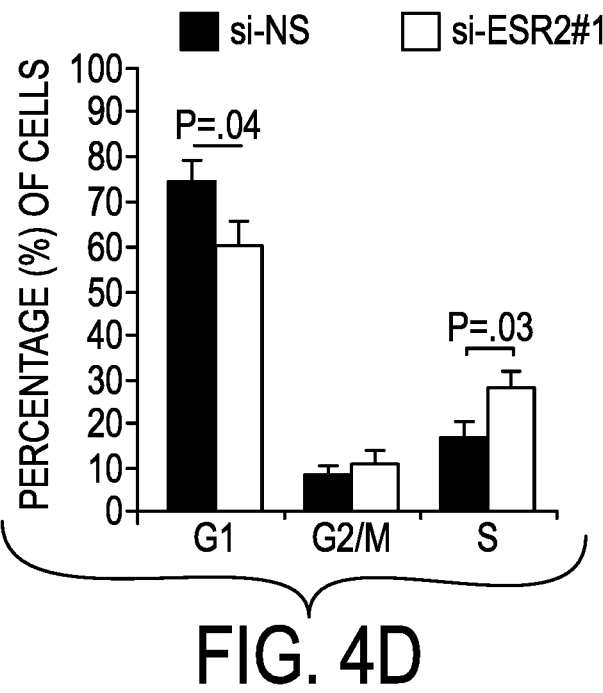
Figure 4E:
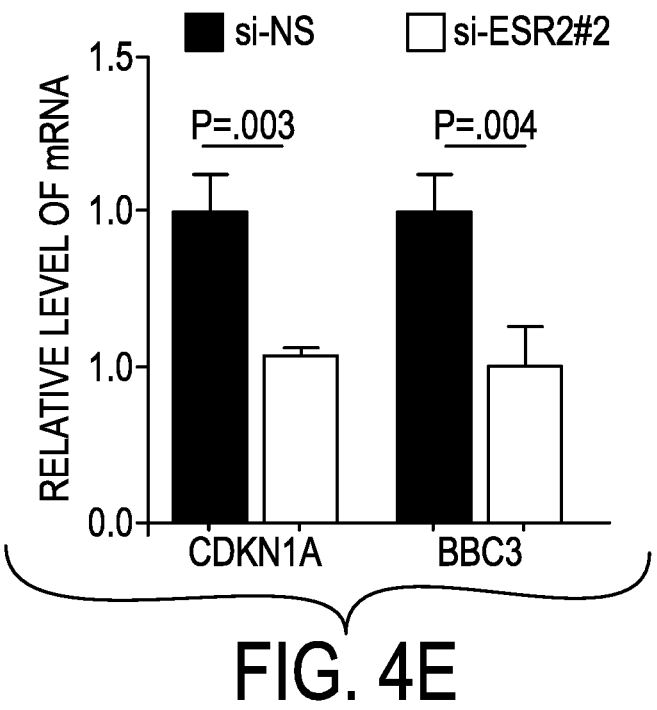
Figure 4F:
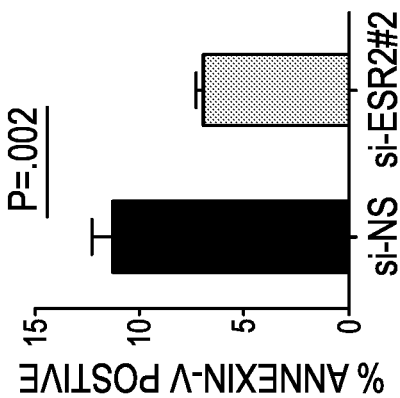
Figure 4F:
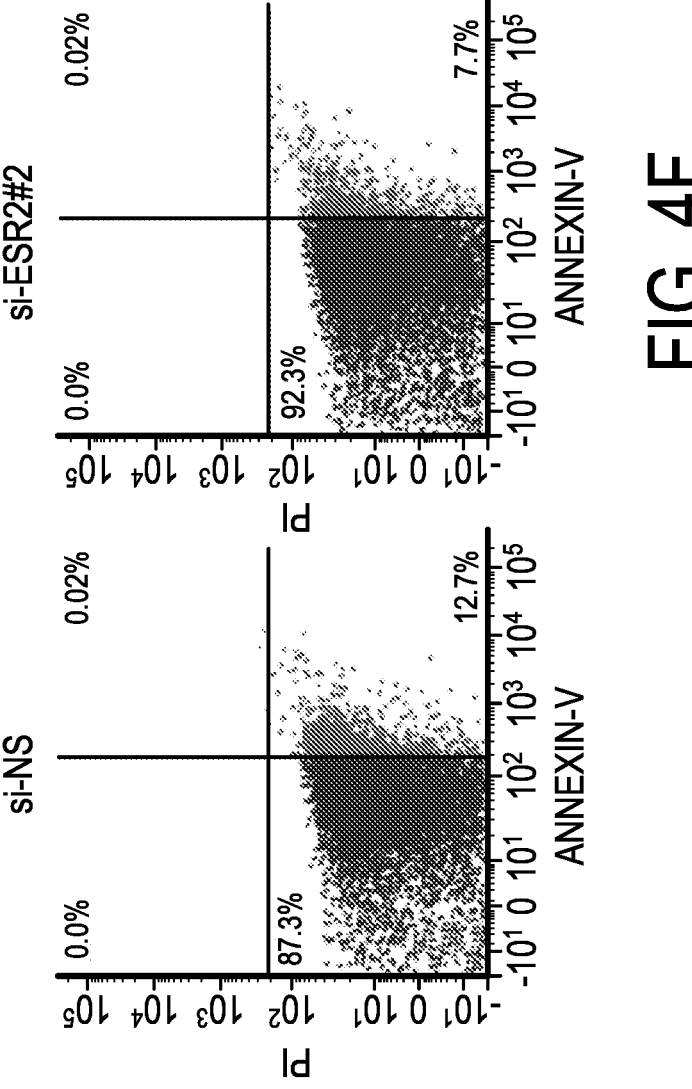
Figure 4G:
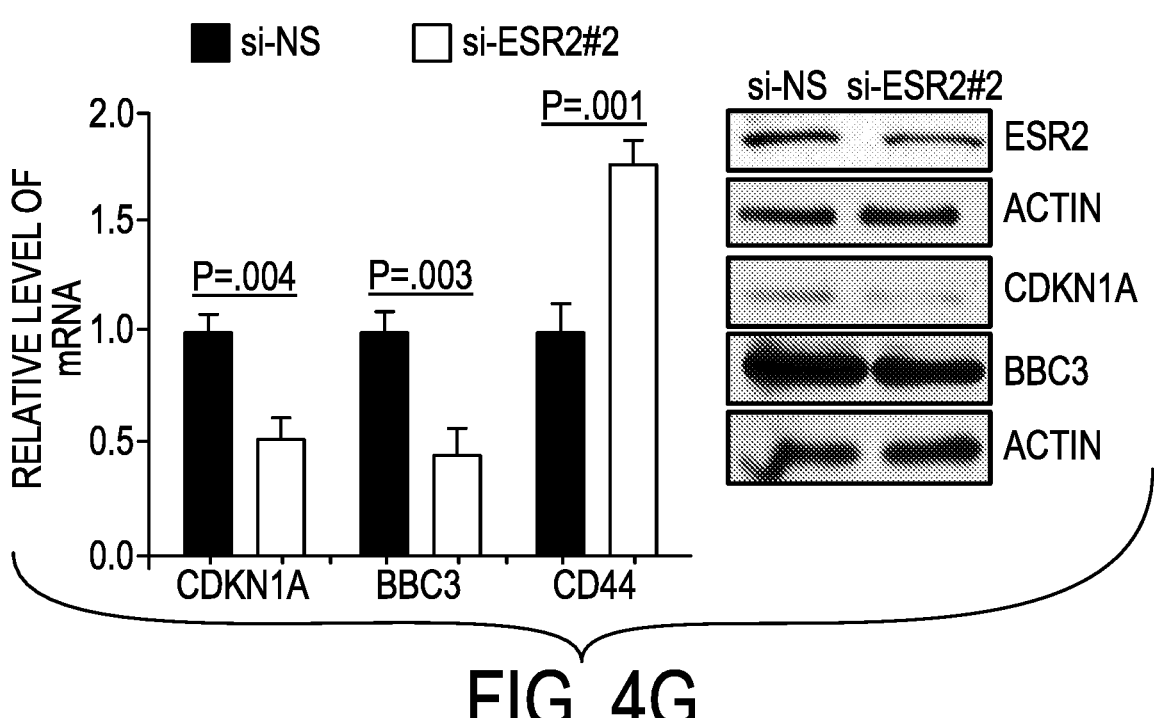
Figure 4H:
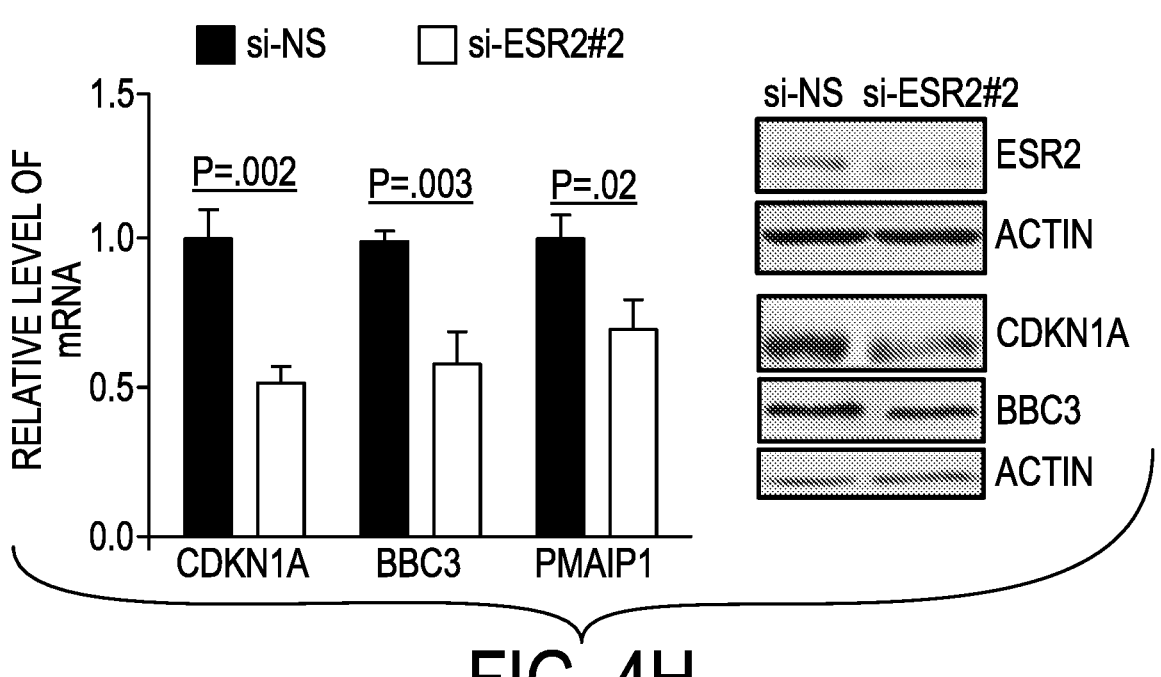
Figure 13A:
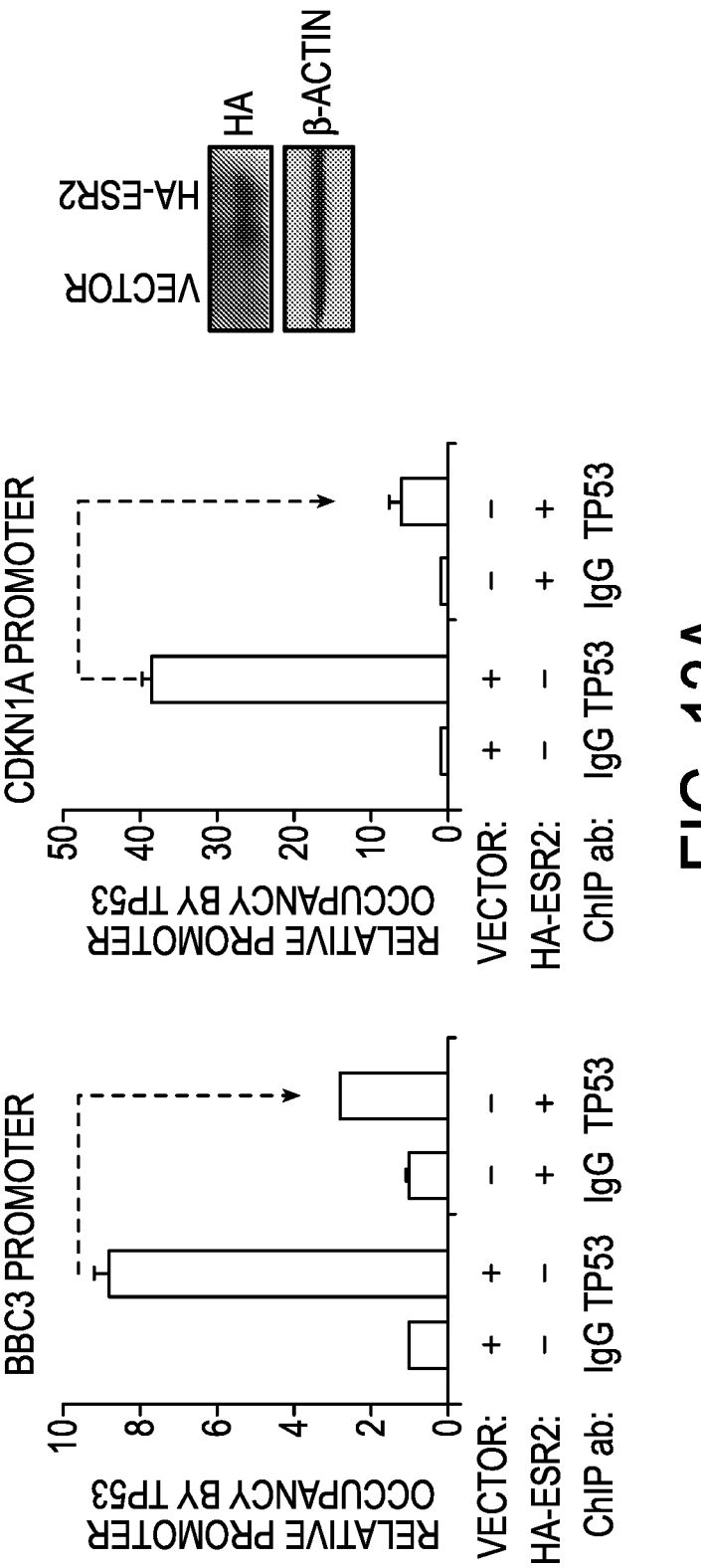
Figures 13B, 13C:
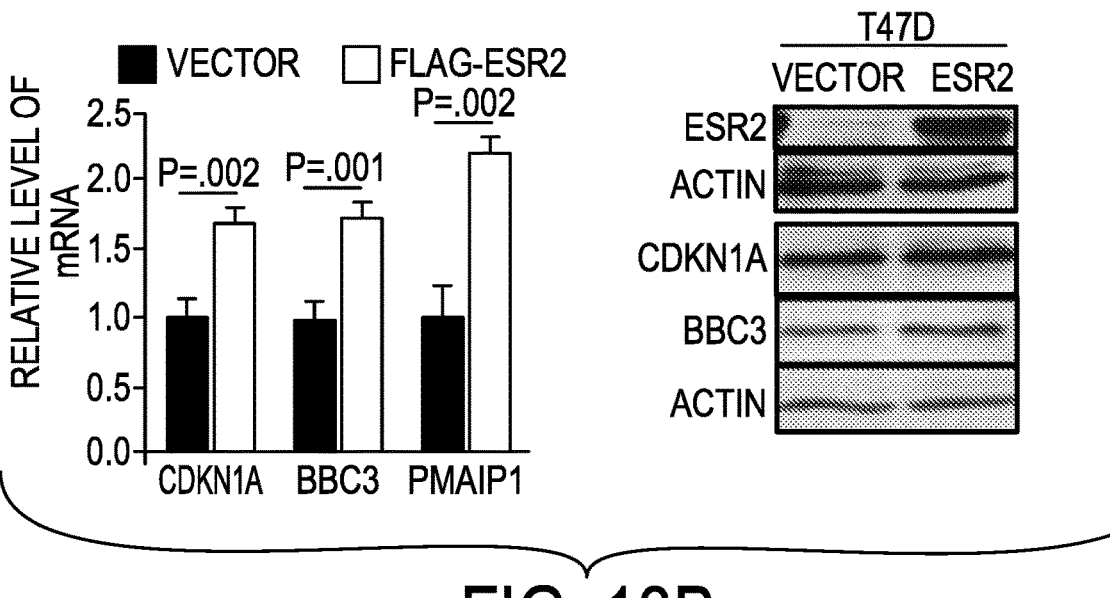
Figure 13D:
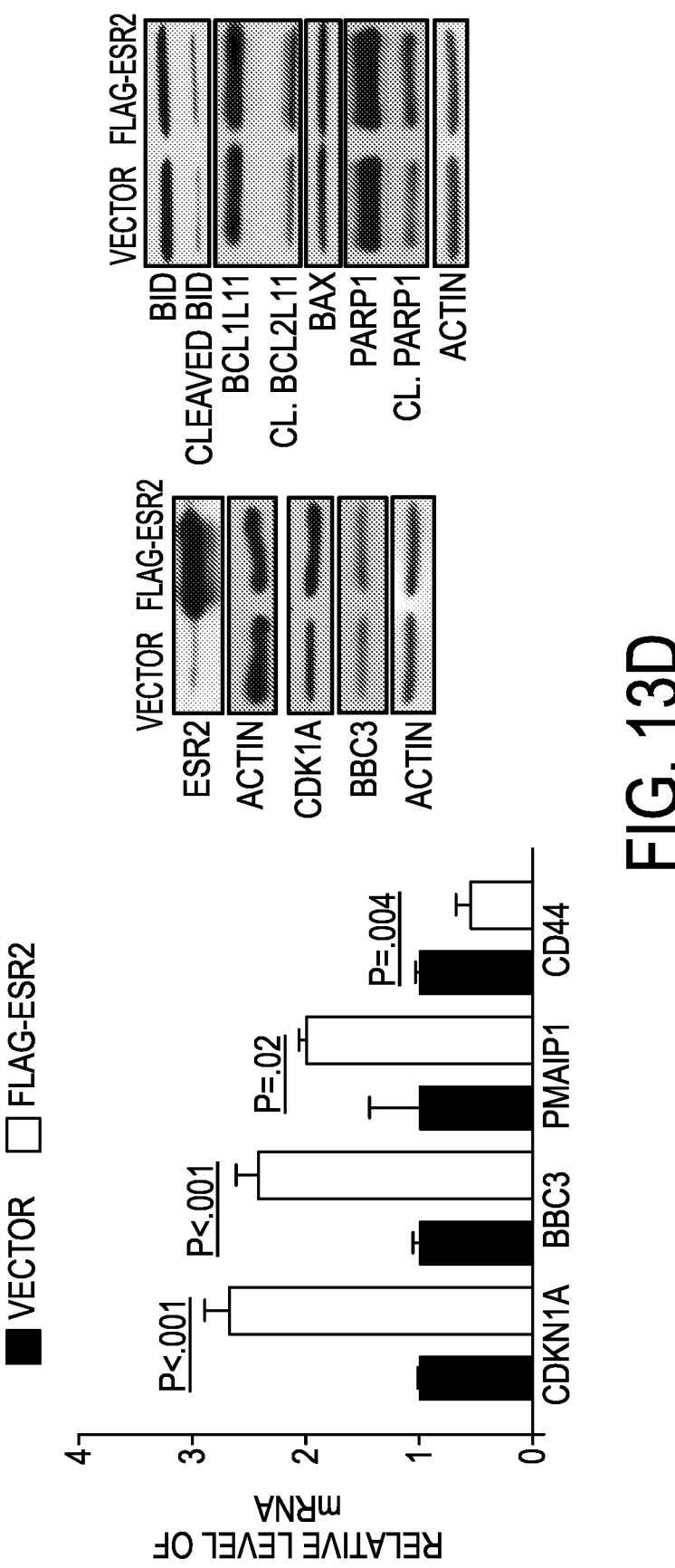
Figure 13E:
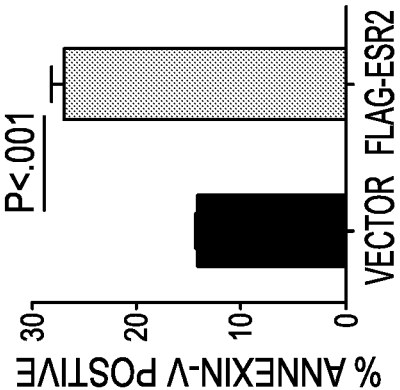
Figure 13E:
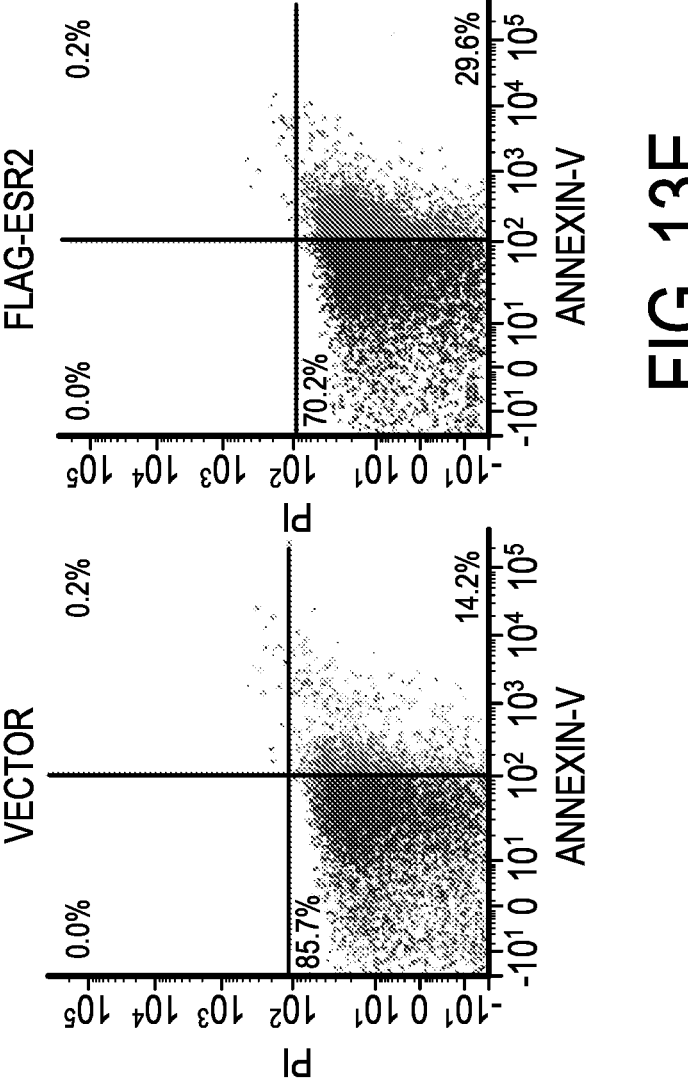

Effect of ESR2 on TP53-Target Gene Expression and Cell Proliferation in the Mutant TP53 Context Unlike in the case of BC cells expressing WT TP53 where increased expression of TP53-target genes CDKN1A (control group mean=1 [SD=0.13] vs ESR2 depletion group mean=2.08 [SD=0.24]; p=0.003) and BBC3 (control group mean=1 [SD=0.06] vs ESR2 depleted group mean=1.92 [SD=0.25]; p=0.003) was observed (FIG. 2G), depleting ESR2 in MDA-MB-231 TNBC cells expressing mutant TP53 resulted in decreased expression of TP53-target genes (FIGS. 4A-B, and FIG. 13C). For example, expression of CDKN1A (control group mean=1 [SD=0.21] vs ESR2 depleted group mean=0.56 [SD=0.12]; p=0.02) and BBC3 (control group mean=1 [SD=0.03] vs ESR2 depleted group mean=0.55 [SD=0.09]; p=0.008) was decreased (FIG. 4A). Similar data were obtained from MDA-MB-468, SK-BR-3, and T-47D cells (FIGS. 4E, 4G, and 4H, respectively). Consistent with the effect on gene expression, there was decreased apoptosis (FIGS. 4C, F) and decreased cell cycle arrest (FIG. 4D) upon depletion of ESR2. Opposite results were obtained when exogenous FLAG-ESR2 was overexpressed in T-47D (FIG. 13B) and MDA-MB-231 (FIGS. 13D-E). Thus, contrary to the pro-proliferative effect of ESR2 in BC cells expressing WT TP53, ESR2 is anti-proliferative in BC cells expressing mutant TP53.

Diametrically Opposite Effects of ESR2 in TNBC Cells Expressing Mutant Versus WT TP53

Since the opposite effects elicited by ESR2 in the context of WT versus mutant TP53 could be due to expression of other proteins and signaling pathways that are different in these cell lines, representing different sub-types of BC, rather than determined by the TP53 context per se. To rule out this possibility, the TP53-dependent duality of ESR2 function was analyzed in the following TNBC cell lines where ESR2 is the only ER expressed: MDA-MB-231 expressing mutant TP53 (R280K); isogenic MDA-MB-231-TP53 knockout with TP53 knockout (generated by CRISPR/Cas-9) (FIGS. 14A-B); BC3-WT TP53 cells expressing WT TP53; isogenic BC3-shTP53 cells where TP53 was stably knocked down; and CAL-51 cells expressing endogenous WT TP53.

Figure 5A:
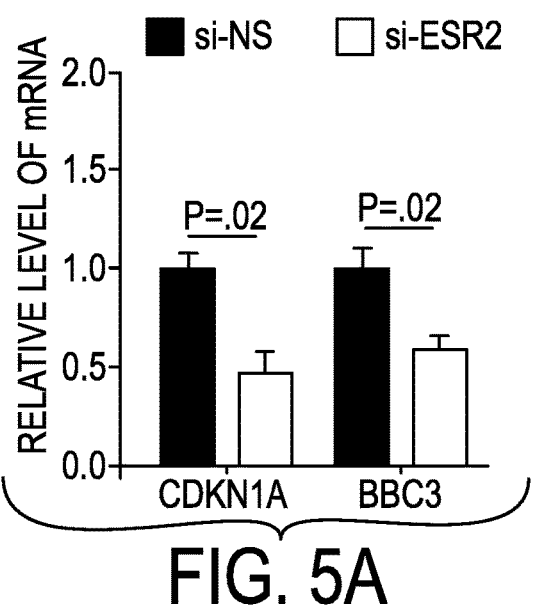
FIGS. 5A-G. Comparison of ESR2 effects in TNBC cells expressing mutant versus WT TP53. A) TP53-target gene expression in MDA-MB-231 with or without knocking down ESR2 with siRNA #2 for 48 hours was determined by qRT-PCR. B) TP53-target gene expression in MDA-MB-23-TP53KO with or without knocking down ESR2 with siRNA #2 for 48 hours was determined by qRT-PCR. C) TP53 target gene expression in MDA-MB-231-TP53KO cells following ESR2 knockdown along with or without transfection with WT TP53 cDNA for 48 hours was determined by qRT-PCR. D) TP53-target gene expression in BC3-WT TP53 cells with or without knocking down ESR2 with ESR2 siRNA #2 for 48 hours was determined by qRT-PCR. Right panel: Expression of CDKN1A, BBC3, and BID proteins in BC3-WT TP53 cells transfected with or without knocking down ESR2 with siRNA #2 for 48 hours were analyzed by immunoblotting. E) TP53-target gene expression in BC3-WT TP53 cells 48 hours post-transfection with or without FLAG-ESR2 was determined by qRT-PCR. F) TP53-target gene expression in BC3-shTP53 cells with and without knocking down ESR2 with siRNA #2 for 48 hours was analyzed by qRT-PCR. G) TP53-target gene expression in CAL-51 cells 48 hours post-transfection with or without FLAG-ESR2 was determined by qRT-PCR. Right panel: Expression of CDKN1A1, and BBC3 proteins in BC3-WT TP53 cells transfected with or without knocking down ESR2 with ESR2 siRNA #2 for 48 hours was analyzed by immunoblotting. All 'p' values were determined by two-tailed Student's t-test. Error bars represent standard deviation (SD). siESR2=ESR2-specific siRNA; qRT-PCR=quantitative real time PCR.
Figure 5B:
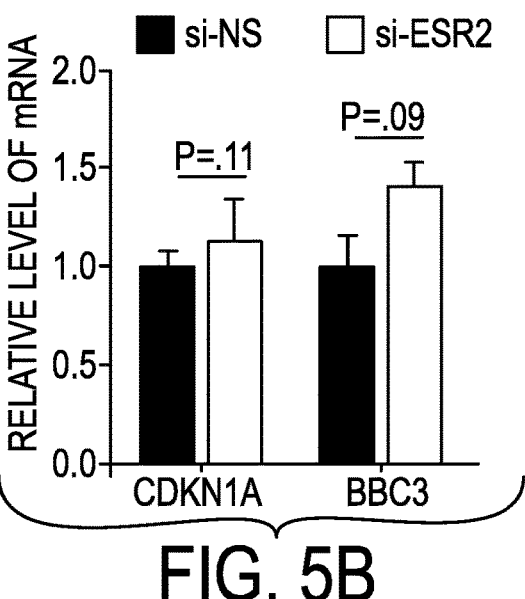
Figure 5C:
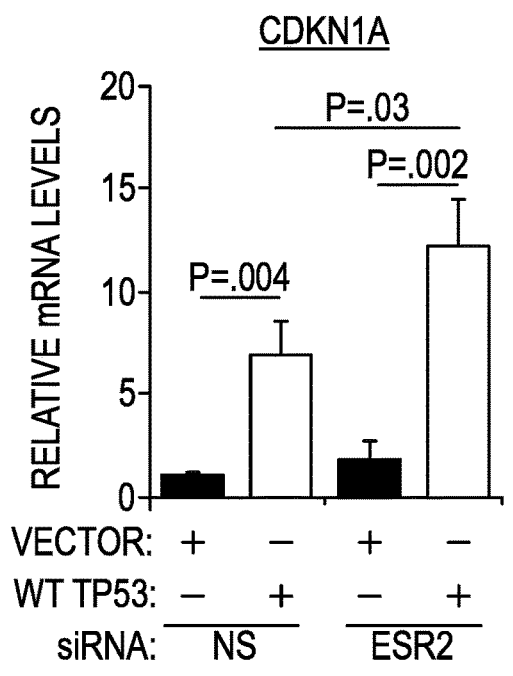
Figure 5C:
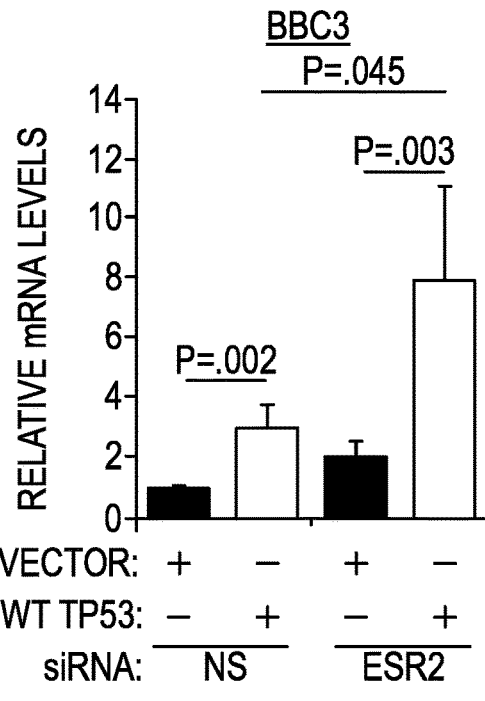

Unlike in the parental MDA-MB-231 cells (FIG. 5A), ESR2 depletion did not have a statistically significant effect on transcription of TP53-target genes in TP53KO cells (FIG. 5B). When the isogenic TP53KO cells were transfected with WT TP53 cDNA, transcription of both CDKN1A and BBC3 (FIG. 5C) was increased, and when ESR2 was depleted, there was further increase in these transcripts, reminiscent of luminal BC cells expressing endogenous WT TP53. Knocking down ESR2 in either null-TP53 or WT TP53 cells did not affect TP53 protein levels (FIG. 14C), ruling out the possibility that changes in TP53 levels caused by ESR2 depletion could have contributed to the ESR2-mediated effects on transcription of CDKN1A and BBC3.

Figures 5D, 5E:
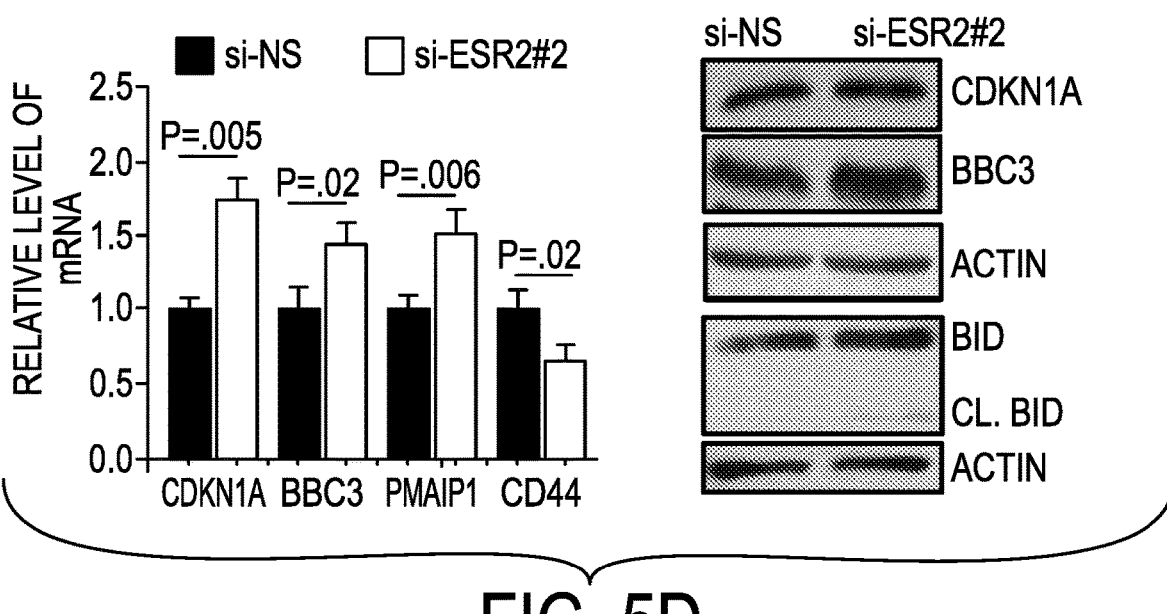
Figure 5F:
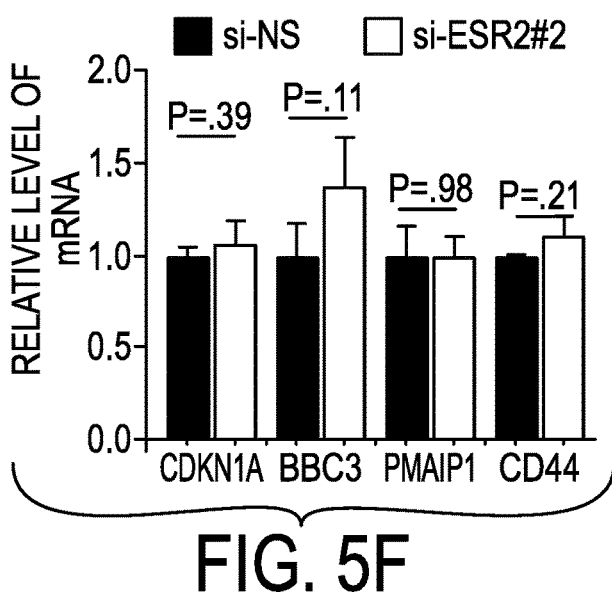
Figure 5G:
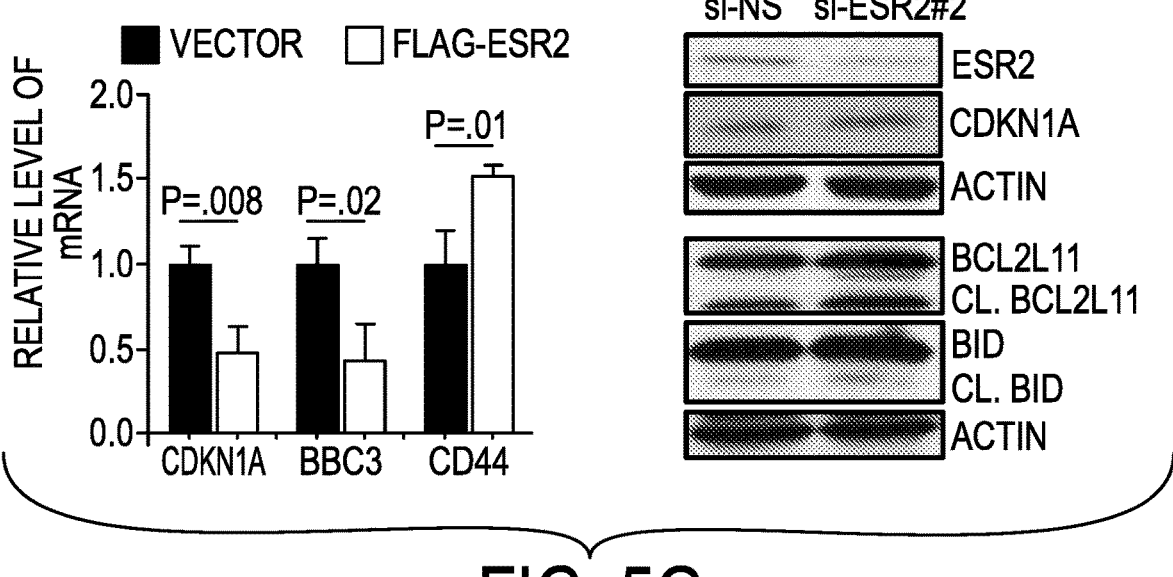

Compared to MDA-MB-231, the BC3 TNBC cell line expressing endogenous WT TP53 (BC3-WT TP53) showed complementary response to manipulating ESR2 levels (depletion versus overexpression) (FIGS. 5D-E). Furthermore, similar to the isogenic MDA-MB-231-TP53KO cells, isogenic BC3-shTP53 cell line where WT TP53 was stably depleted did not show any effect on TP53-target gene expression when ESR2 was depleted (FIG. 5F). Moreover, CAL-51 cells showed similar effects as observed in BC3-WT TP53 cells (FIG. 5G). These data show that ESR2 is pro-proliferative in TNBC cells expressing WT TP53 and anti-proliferative in those expressing mutant TP53. Both these effects are TP53-dependent.

Figure 6A:
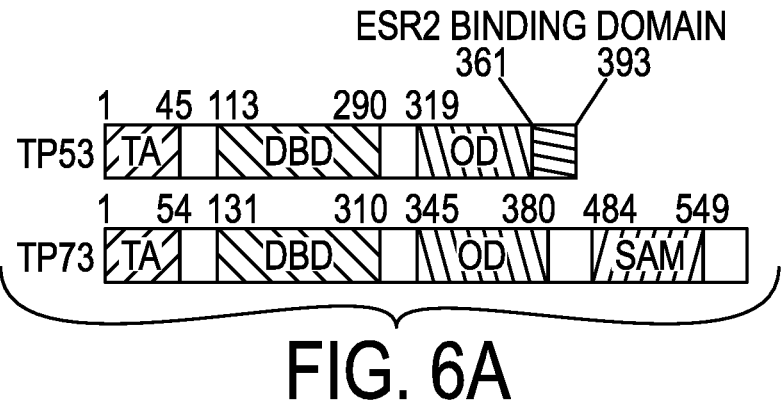
Figure 6B:
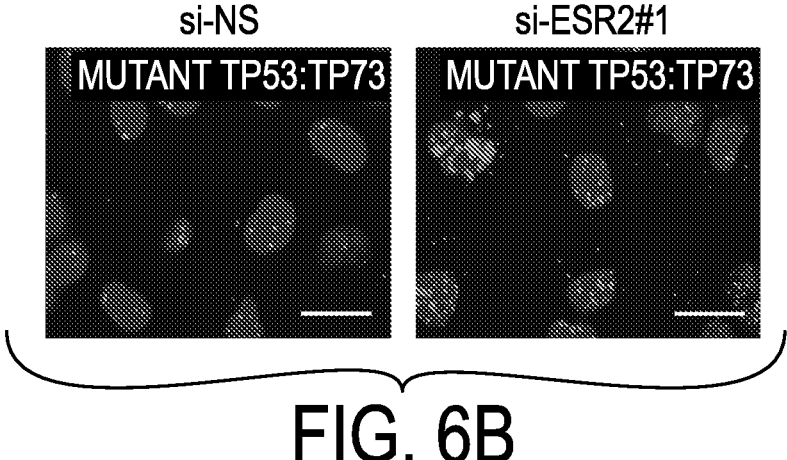
Figure 6C:
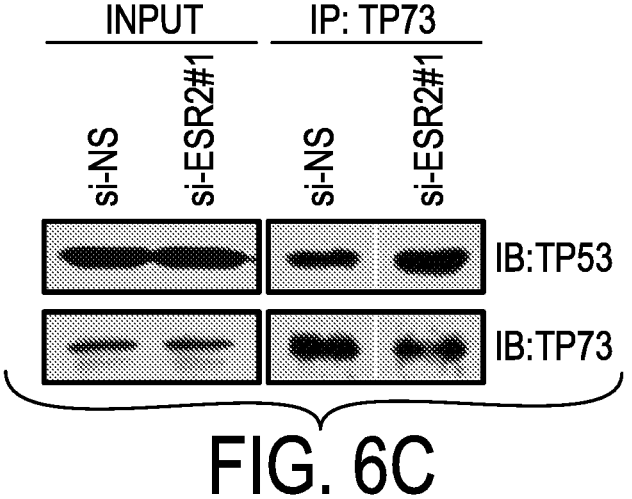

Effect of Sequestration of Mutant TP53 by ESR2 on Mutant TP53-TP73 Complex and TP73 Activation One of the major tumorigenic gain-of-functions of mutant TP53 is its ability to bind and inactivate tumor suppressor TP73, a member of the TP53 family (FIG. 6A). CDKN1A, BBC3, and PMAIP1 have been reported to be transcriptional targets of TP73. As TP73 deregulation is a frequent event in BC and is expressed in MDA-MB-231 cells, ESR2 may sequester and prevent mutant TP53 from binding and inhibiting tumor suppressor TP73, leading to TP73 activation and its enhanced recruitment to TP53/TP73-target gene promoters. PLA showed interaction between endogenous TP73 and mutant TP53 in MDA-MB-231, MDA-MB-468, and SK-BR-3 cells and the interaction was increased when ESR2 was depleted (FIGS. 6B, G, and I) while the opposite was observed in ESR2-overexpressing cells (FIGS. 7A-B). Furthermore, co-immunoprecipitation assay showed that TP73 binding to mutant TP53 was increased in ESR2-depleted cells (FIG. 6C) indicating sequestration of mutant TP53 by ESR2 leads to reduced TP73-mutant TP53 interaction.

FIGS. 15A-B show the effect of overexpression of ESR2 on mutant TP53-TP73 interaction. MDA-MB-231 cells (FIG. 15A) and SKBR-3 cells (FIG. 15B) were transfected with FLAG-ESR2 and were subjected to PLA using a mouse anti-TP53 antibody (DO-1) and a rabbit anti-TP73 antibody (H-79). An additional staining for ESR2 (using mouse anti-FLAG-Alexa[488]) was incorporated during the amplification stage of PLA to delineate transfected from untransfected cells. White dotted line delineates the boundary of ESR2 overexpressing cells (also indicated with white arrowhead).

Figure 1A:
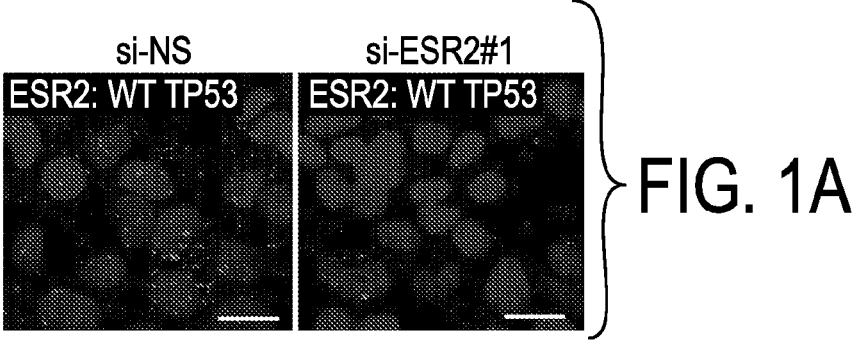
Figure 1B:
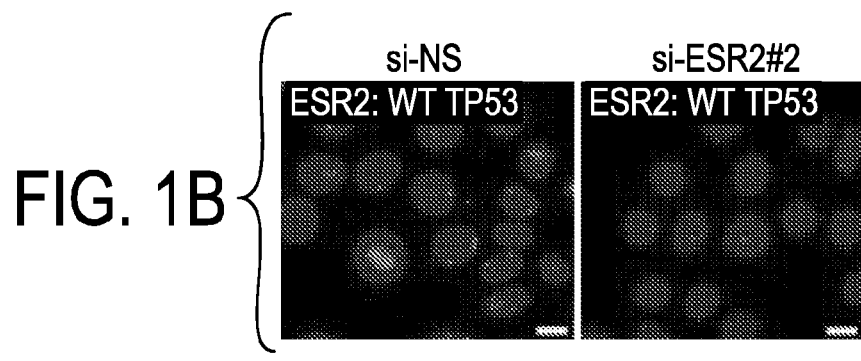
Figure 1C:
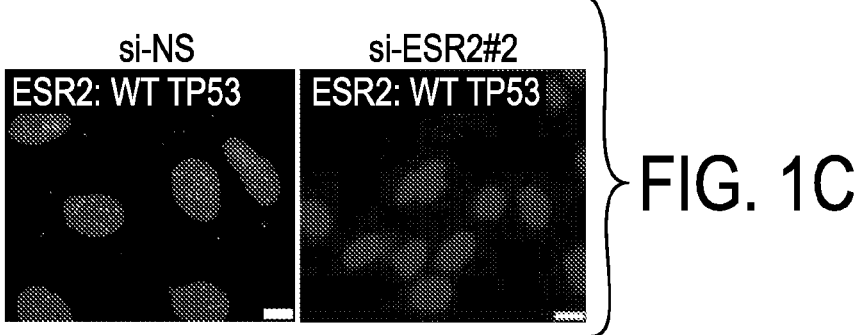
Figure 1D:
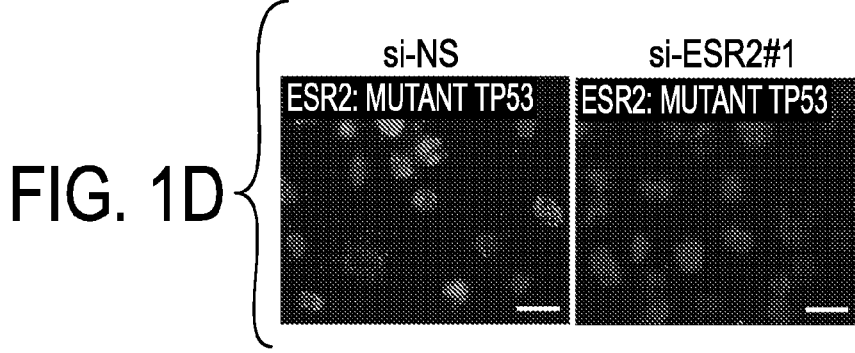
Figure 1L:
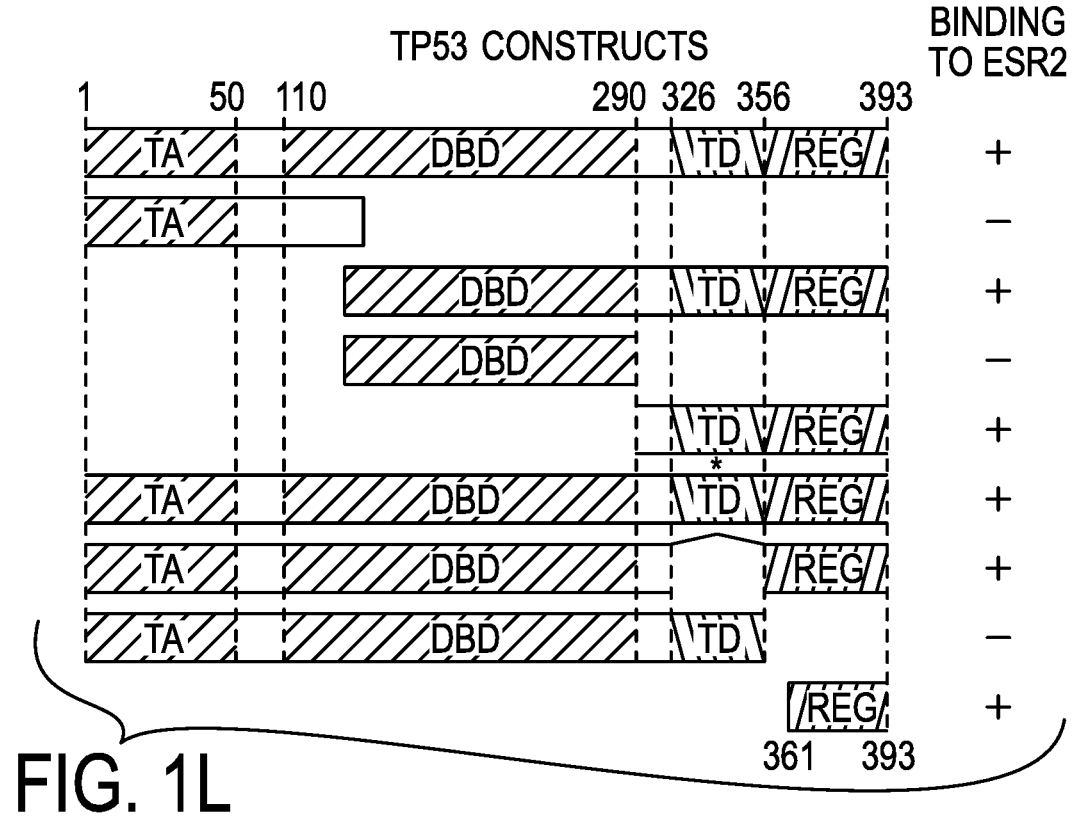
Figure 1M:
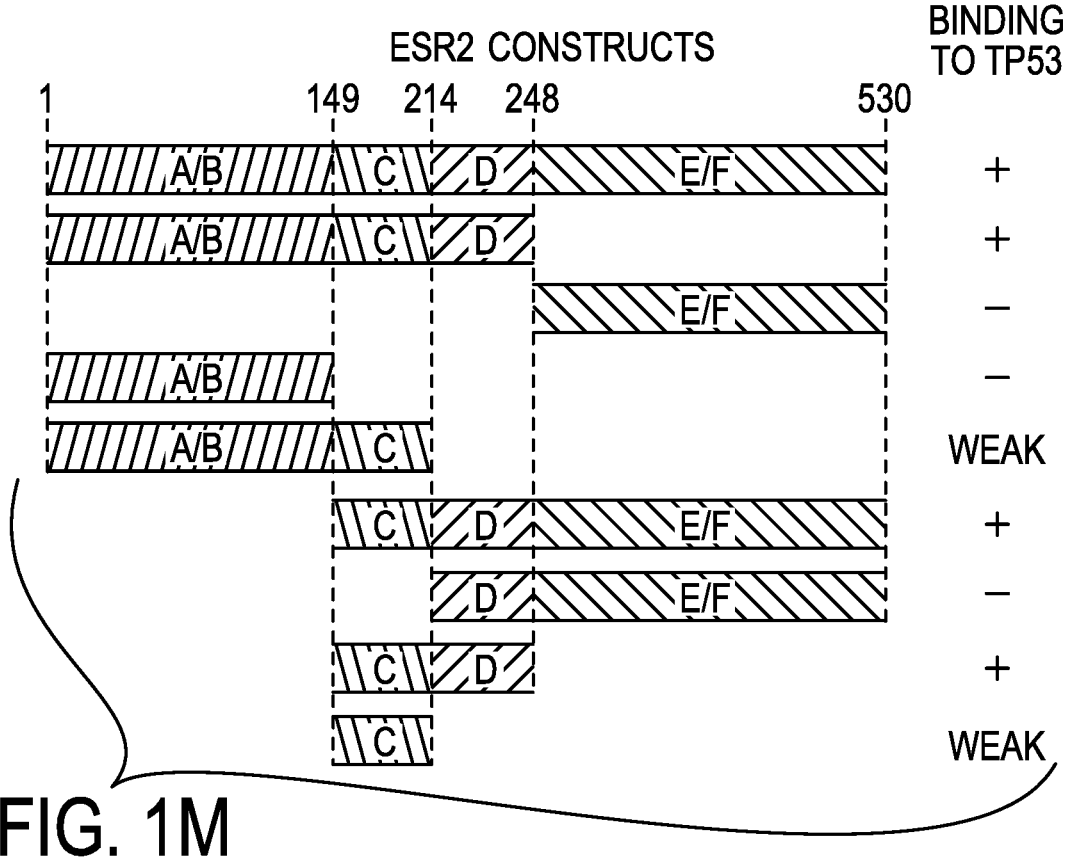
Figure 6F:
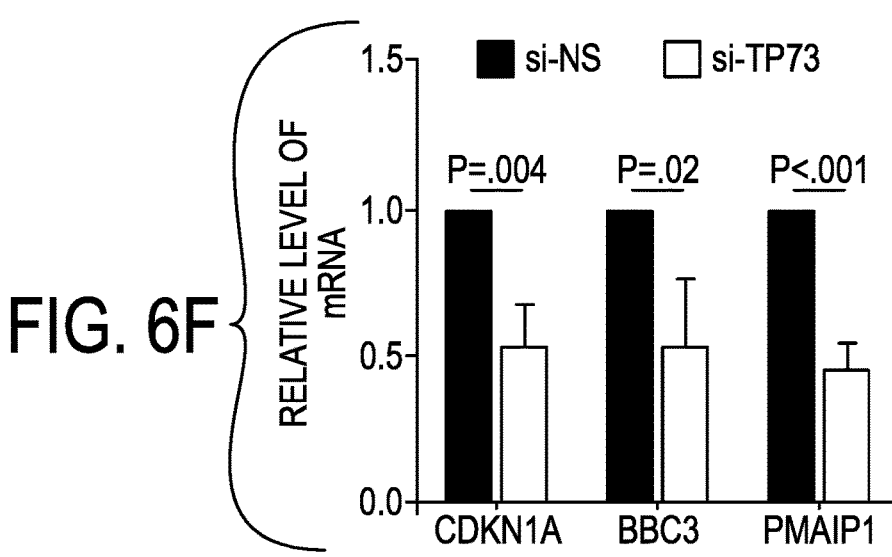
Figure 6G:
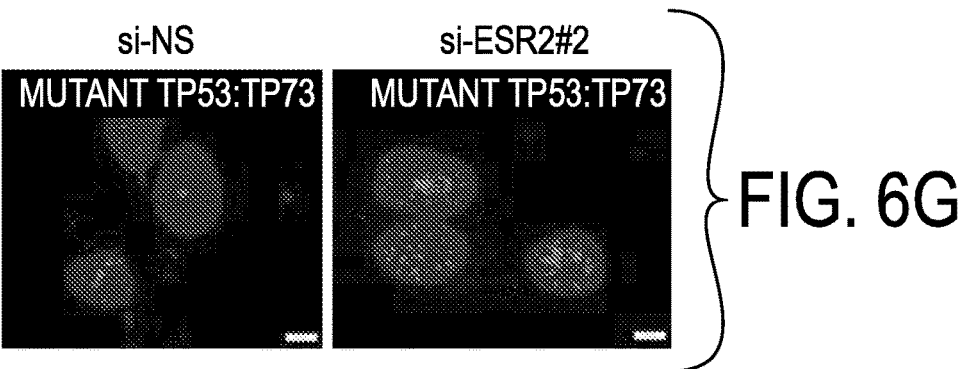
Figure 6H:
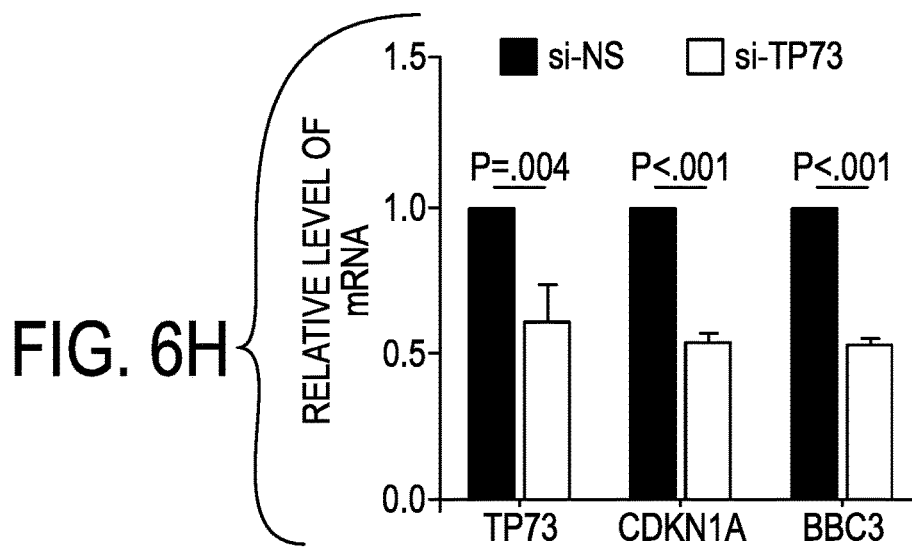
Figure 6I:
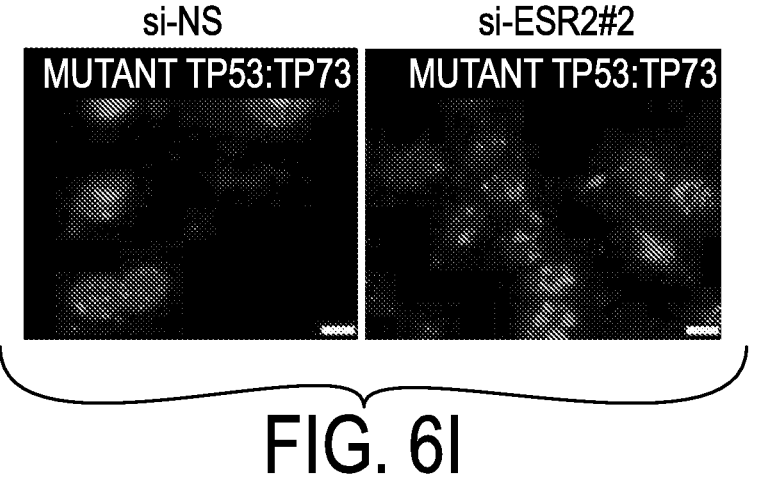
Figures 11A, 11B, 11C:
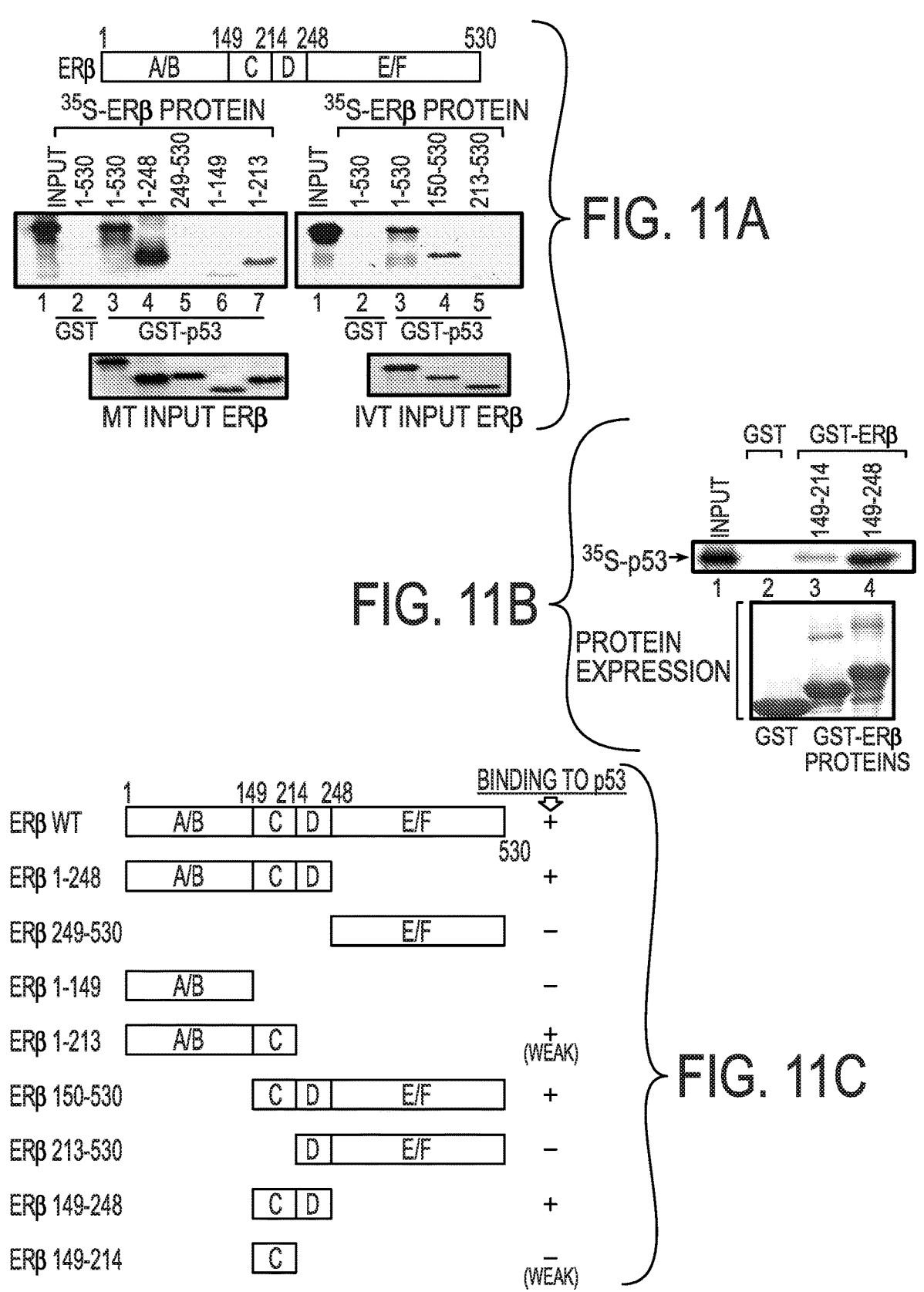
Figure 11D:
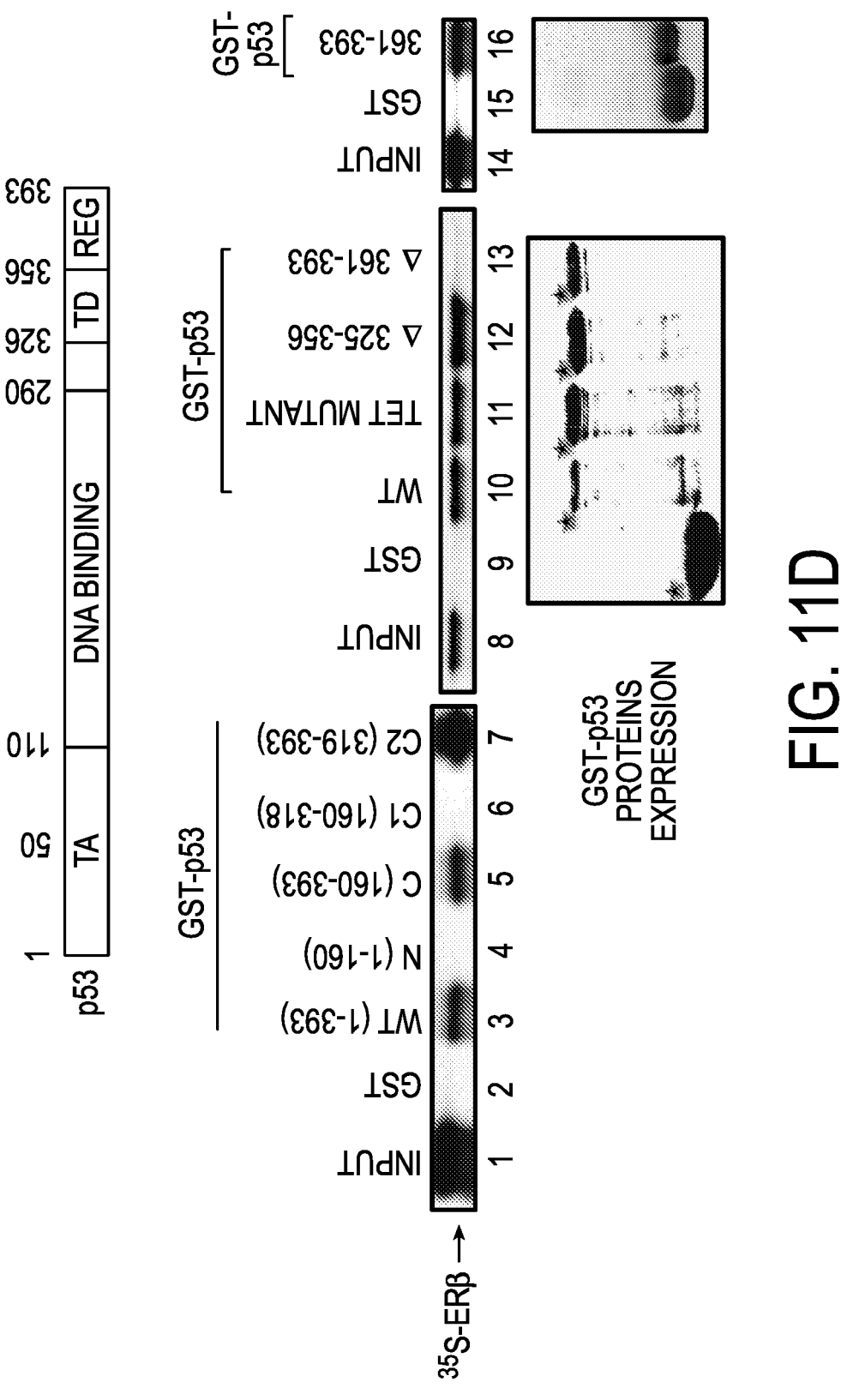
Figure 11E:
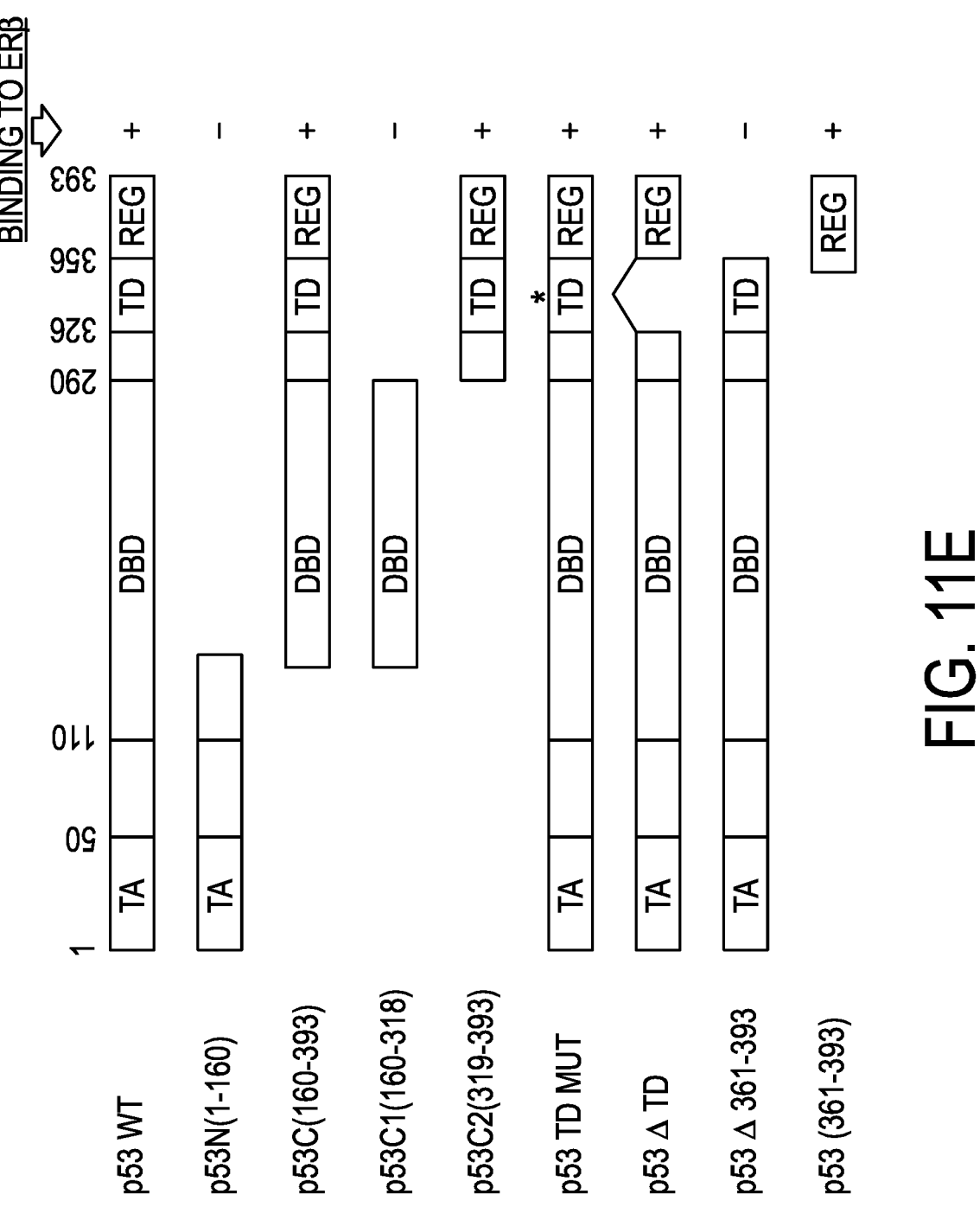
Figure 12C:
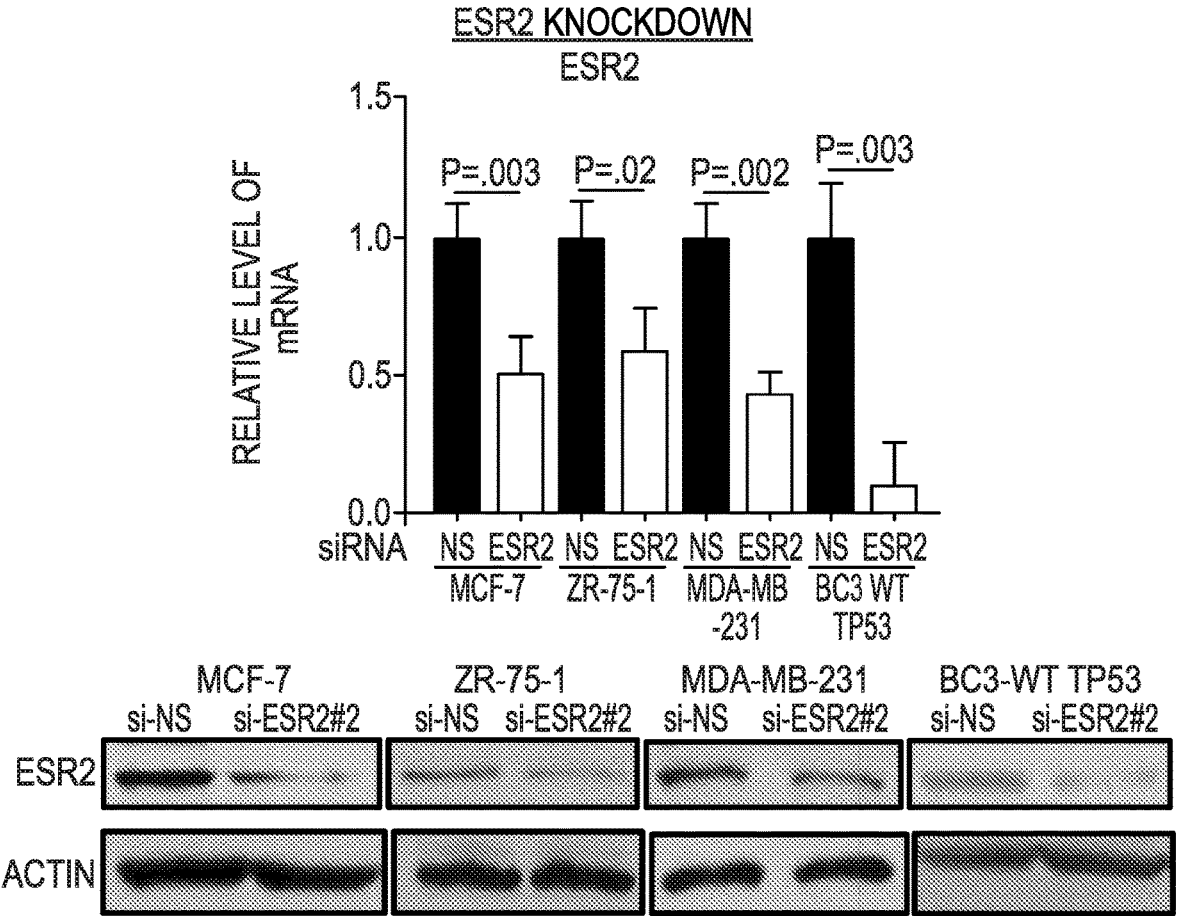
Figures 12D, 12E:
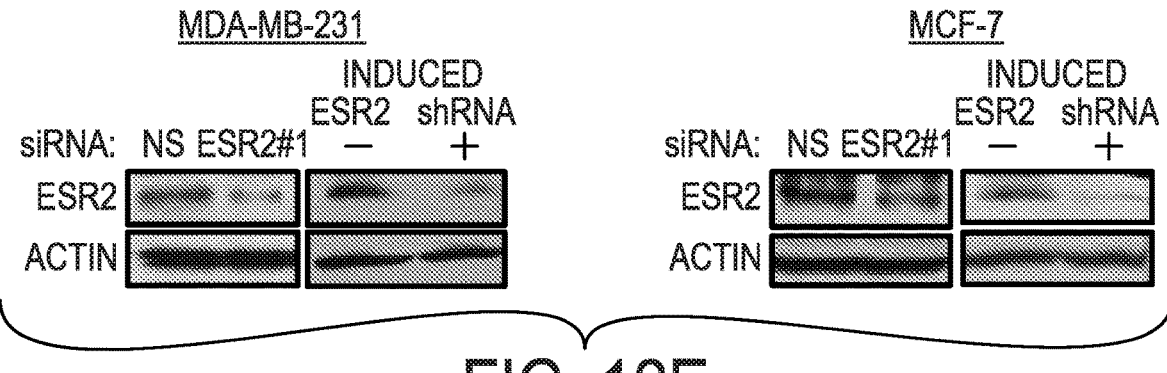

Interaction of endogenous ESR2 or exogenously overexpressed FALG-ESR2 with endogenous TP73 was considerably low (FIGS. 16A-C). The ability of ESR2 to discriminate between mutant TP53 and TP73 for binding could be a result of the lack of conservation in TP73 of the carboxy-terminal domain of TP53 (FIG. 6A) as this domain is minimally required for binding to ESR2 (FIG. 1L and FIGS. 11D-E). Indeed, qChIP assays showed that TP73 recruitment to CDKN1A and BBC3 promoters in MDA-MB-231 cells is decreased when ESR2 was depleted (FIG. 6D). Consistent with these observations, depleting TP73 decreased transcription of TP53 target genes (FIGS. 6E-F, H). FIG. 19B shows quantification of PLA data in FIGS. 6A-J.

Figure 6J:
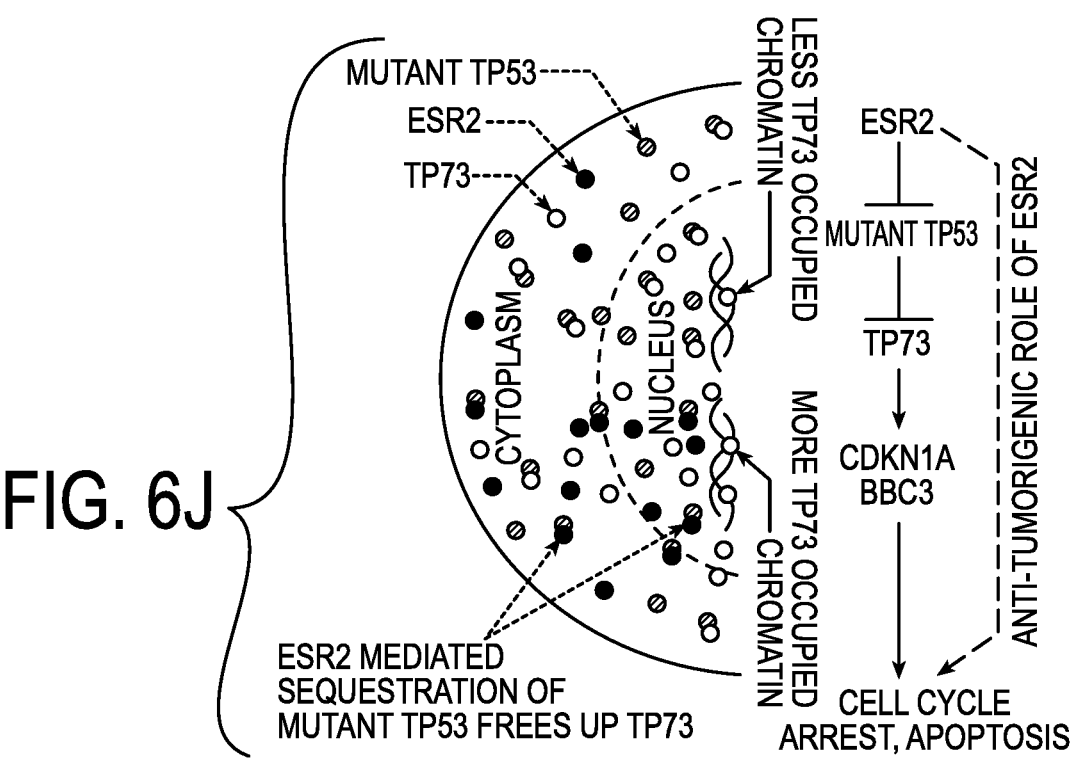

These data demonstrate that by sequestering mutant TP53, ESR2 de-represses TP73 leading to increased expression of its target genes that are anti-tumorigenic (FIG. 6J).

Effect of Tamoxifen on ESR2-Mutant TP53 Interaction and TP73 Activity

Figures 7E, 7F, 7G:
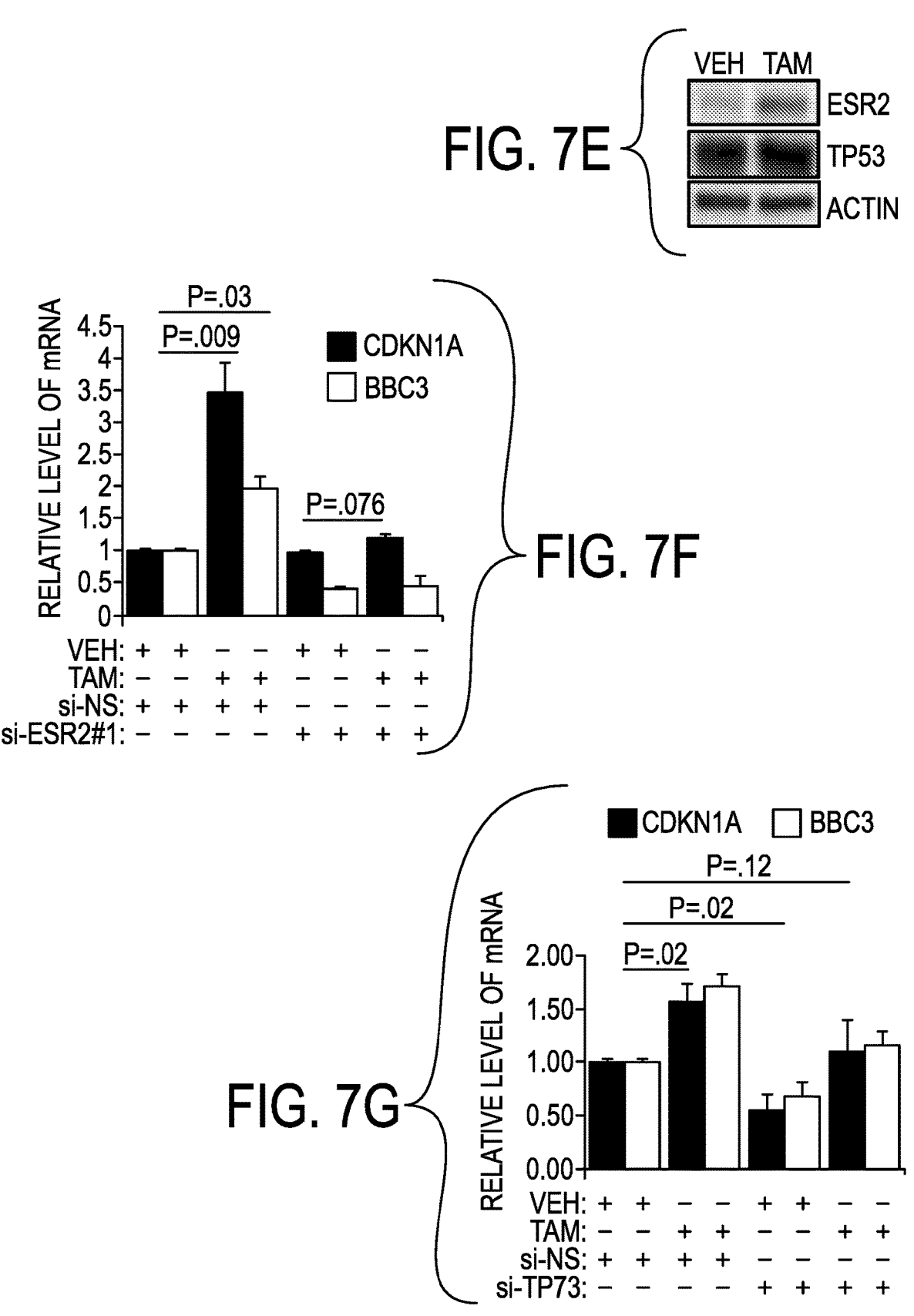

Tamoxifen is a competitive inhibitor of ESR1/ERα and is widely used to treat ESR1-positive BC whereas it is not standard-of-care for TNBC. However, there have been isolated reports on beneficial effects of tamoxifen therapy in certain cohorts of ESR1-negative BC. It has been reported that high levels of ESR2 in ESR1-negative BC and TNBC patient tumors were associated with good clinical outcome in response to tamoxifen therapy. In another study, expression of ESR2 along with its co-regulator was found to be predictive for benefit from tamoxifen therapy. Furthermore, fulvestrant was reported to synergize with tamoxifen to upregulate ESR2 in BC cells, and ESR2 enhanced the sensitivity of ESR1-positive BC cells to the anti-estrogenic effects of endoxifen, a metabolite of tamoxifen. However, the mechanistic basis for such beneficial effects of tamoxifen in TNBC remains undefined. This example shows that, surprisingly, treatment with 4-hydroxy tamoxifen leads to increased ESR2-mutant TP53 interaction in MDA-MB-231, MDA-MB-468, and SK-BR-3 cells (FIGS. 7A, C, and D, respectively). Concomitantly, there was decreased mutant TP53-TP73 interaction (FIG. 7B), which in turn, led to enhanced recruitment of TP73 to the PUMA gene promoter (FIG. 17A). ESR2 protein levels were increased after tamoxifen treatment (FIGS. 7E, H). Tamoxifen failed to enhance transcription of CDKN1A and BBC3 in the absence of ESR2 or TP73 in MDA-MB-231 cells (FIGS. 7F-G), MDA-MB-468 (FIGS. 7I-J), and SK-BR-3 cells (FIGS. 17B-C). FIG. 19C shows quantification of PLA data shown in the FIGS. 7A-J.

Figures 18A, 18B:
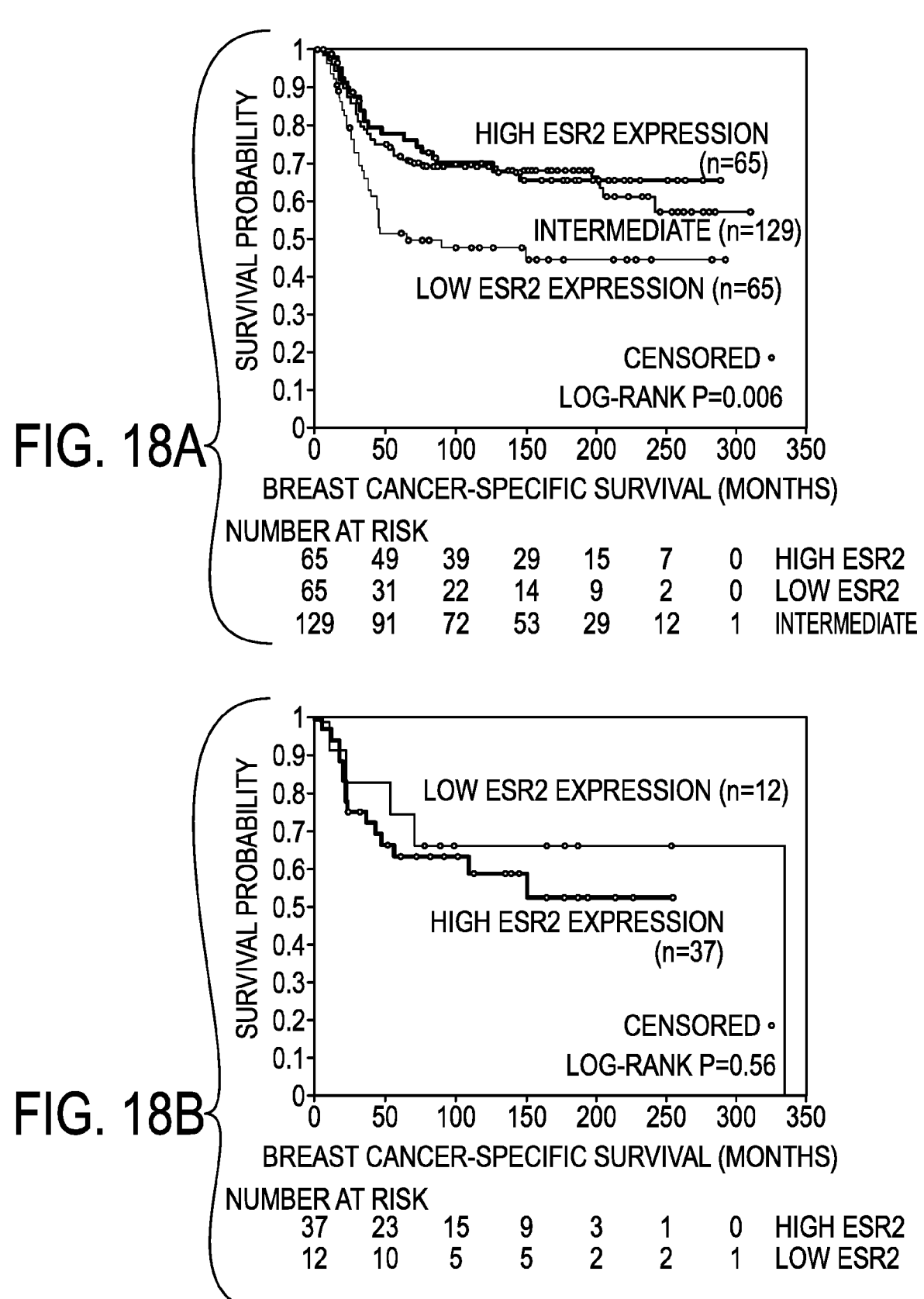
Figure 18C:
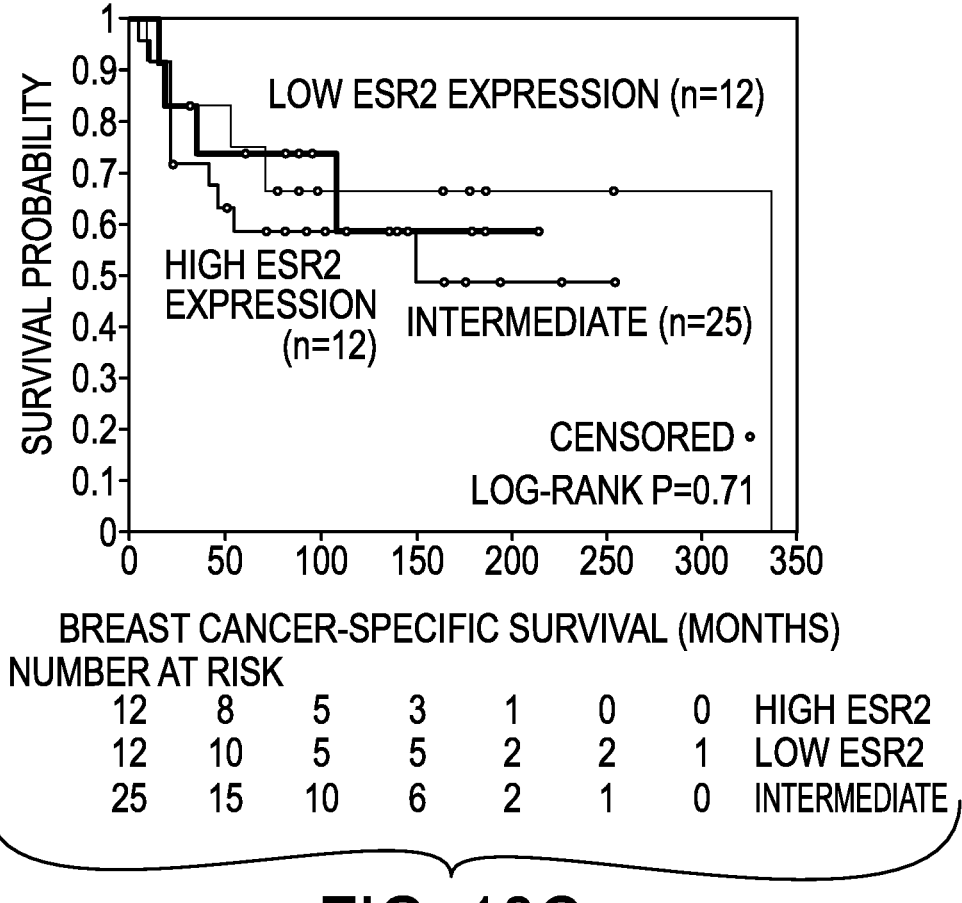

Impact of TP53 Status on the Prognostic Role of ESR2 in Patients with Basal-Like/TNBC Tumors As in the case of TNBC cell lines, TP53 and ESR2 protein expression (IHC) and their interaction were observed in representative TNBC tumor tissues (FIG. 8A). To confirm the findings from the in vitro experiments with cell lines, data was analyzed from 308 patients with Basal-like tumors in the METABRIC cohort of 1904 BC patients. In the mutant TP53 subgroup of the basal-like tumors (n=259), low levels of ESR2 mRNA were associated with poor prognosis for BCSS (log-rank test p=0.001 (FIG. 8B); univariate Cox regression HR=0.32, 95% CI=0.08-1.26; p=0.10 (Table 4) and overall survival (log-rank test p<0.001, univariate Cox regression analysis HR=0.26, 95% CI=0.08-0.84, p=0.02 (Table 4). Combined expression of ERβ and mutant TP53 is a prognostic marker for triple negative breast cancer (TNBC). In the WT TP53 subgroup (n=49), lower levels of ESR2 were not associated with better prognosis (FIGS. 18A-C). ESR2 expression levels per se did not appear substantially affected by TP53 status in the Basal-like subgroup (FIG. 8C).

Figure 18D:
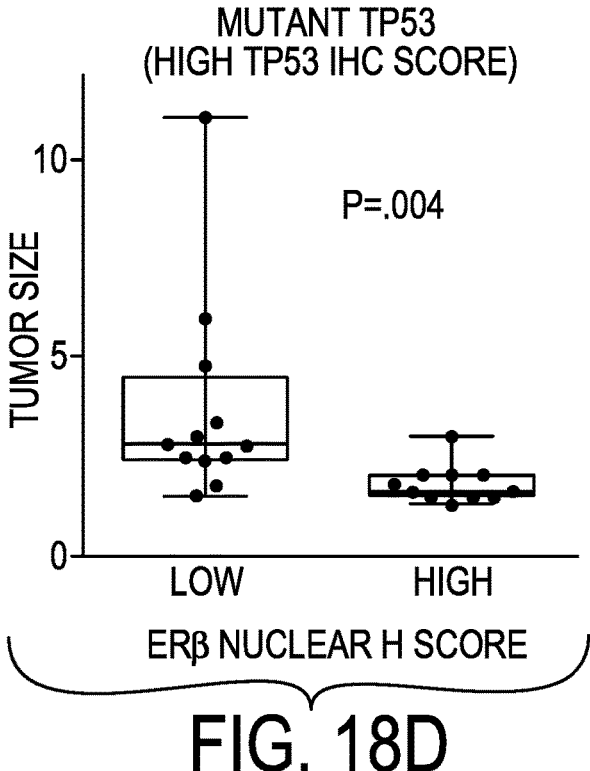
Figure 18E:
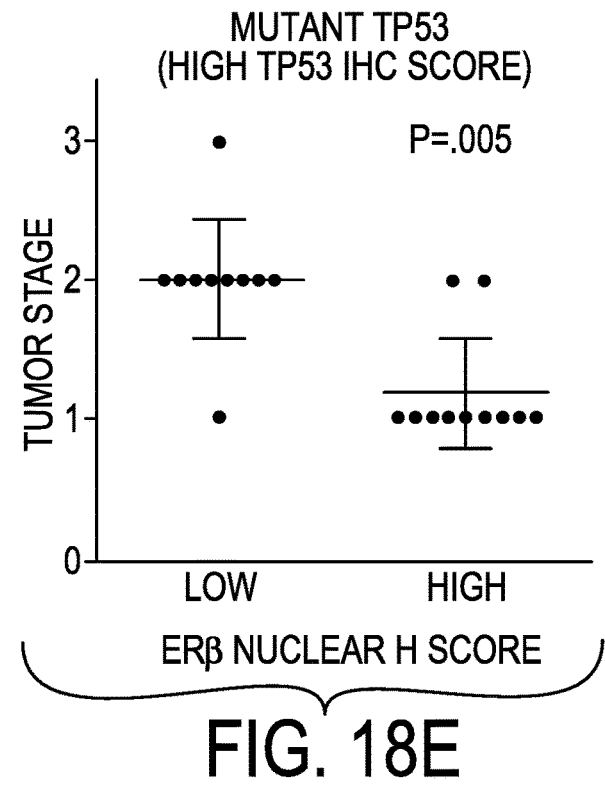
Figure 18F:
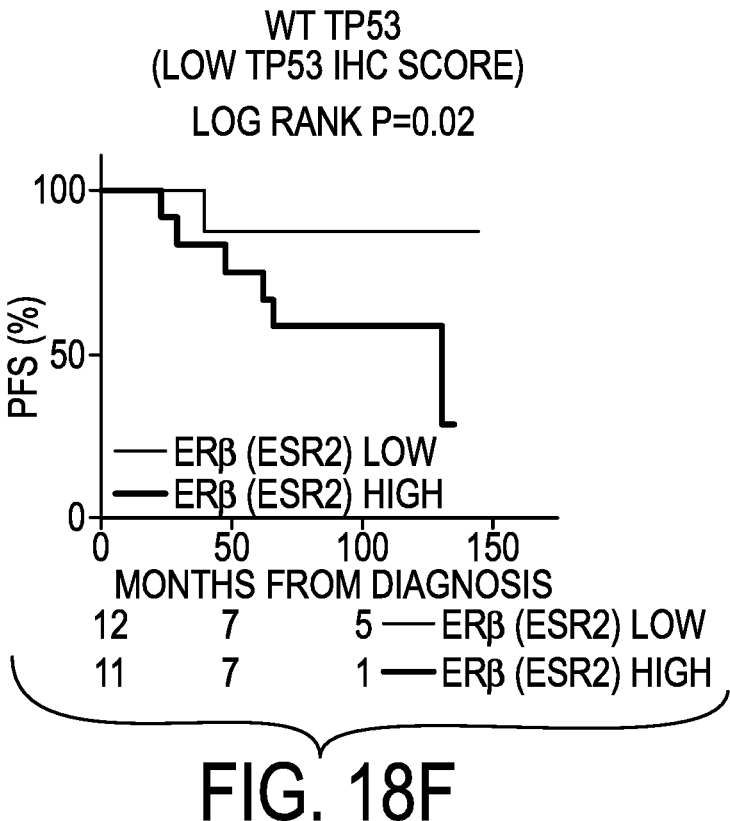
Figure 18G:
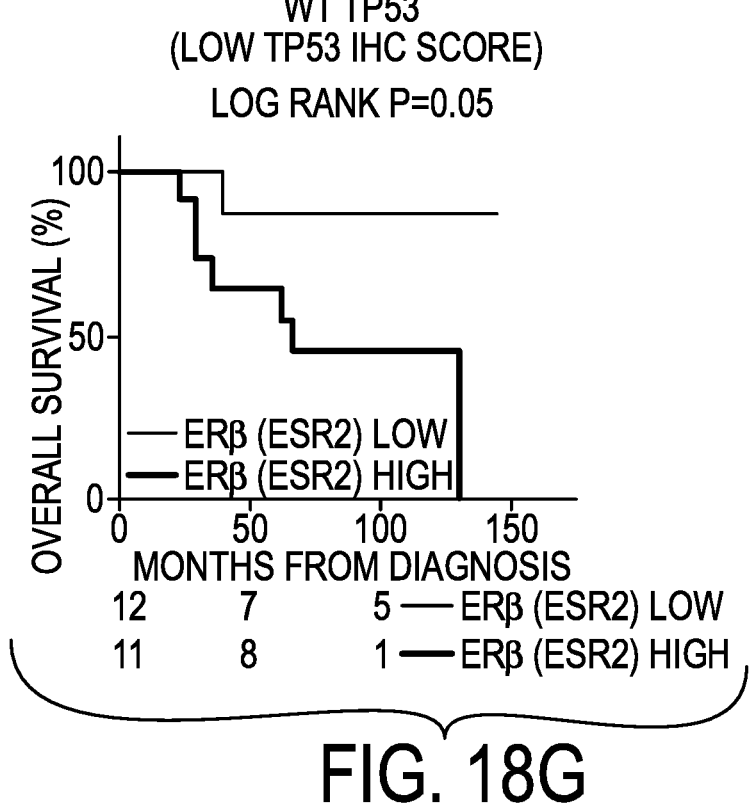

The data from METABRIC cohort was complemented with those from a small TNBC patient cohort (n=46) from Roswell. The patient tumors were stratified into high and low ESR2 as well as high and low TP53 expression based on median cut-off of continuous H-scoring. As there was not sufficient tumor tissue available for sequencing TP53, intensity of IHC staining of TP53 was used as a surrogate for determining TP53 mutation status. Tumors with mutant TP53 and higher levels of ESR2 were smaller in size, and lower in stage (FIGS. 18D-E). Consistent with these data, TNBC patients with tumors with WT TP53 and high ESR2 levels had worse progression-free survival (PFS) and overall survival (OS) (FIGS. 18F-G).

Discussion

Although bi-faceted functioning has been proposed to reconcile some of the disparate, complex, and often contradicting findings on ESR2 functions, the mechanistic basis for such duality has remained largely unknown. This example demonstrates that TP53 status is a determinant of pro-versus anti-proliferative activity of ESR2 in BC cells. TP53 mutations have different clinical relevance depending on the subtypes of BC. Clinical significance of the cellular and molecular data on TP53-dependent differential function of ESR2 is validated by the findings from the METABRIC TNBC patient cohort. In the mutant TP53-expressing Basal-like tumors, those with high ESR2 levels have better survival. In the case of WT TP53-expressing tumors, those with high ESR2 levels were trending toward worse survival, although the difference was not statistically significant. Like most Basal-like/TNBC patient cohorts, only 16% of META-BRIC cohort was expressing wildtype (WT) p53 and such low number of patients likely contributed to the statistically non-significant survival in this sub-category. Patient data from the Roswell cohort, although based on TP53 status determined by surrogate IHC staining, are consistent with that obtained from the much larger METABRIC cohort. These findings suggest that ESR2-TP53 combination can be used to stratify TNBC into therapeutically actionable subgroups.

The data that treatment with tamoxifen can lead to sequestration of mutant TP53 away from TP73 and thereby reactivate tumor suppressor activities of TP73, provide for the first time, a strong rationale for suggesting that tamoxifen therapy could be beneficial to Basal-type/TNBC patients expressing mutant TP53. Also, combined expression of ERβ and mutant TP53 is a prognostic marker for triple negative breast cancer (TNBC) and can be used to stratify TNBC patients into the group that will be benefited by tamoxifen (or tamoxifen+chemotherapeutic agent) therapy. On the other hand, based on the data that ESR2 is pro-proliferative in the WT TP53 context, TNBCs expressing WT TP53, tamoxifen or other agents that increase ESR2-WTP53 interaction may not only be ineffective as anti-tumor agents, but also may contribute to adverse outcome. DNA sequencing (using various methods known to those of skill in the art) is used to determine WT versus mutant sequence of TP53.

In conclusion, this example provides a reason for the previous disparate reports on opposite functions of ESR2 in BC. This example shows that depending on the WT-versus mutant TP53 status, downregulating or upregulating ESR2 alone as well as in combination with compounds capable of disrupting the WT TP53-ESR2 interaction or enhancing mutant TP53-ESR2 interaction can be used as a therapeutic approach. The example demonstrates that effects of tamoxifen have translational significance, especially because tamoxifen can be repurposed quickly for precision medicine to treat Basal-like/TNBC tumors stratified based on TP53 status.

6.2. Example 2: Combining Tamoxifen with Doxorubicin (Adriamycin) Increases Anti-Tumor Activity Introduction As discussed above in Section 6.1. Example 1, the standard of care for triple negative breast cancer (TNBC) is currently a combination therapy of Anthracycline (e.g., Doxorubicin/Adriamycin), Cyclophosphamide, and Taxol ("ACT"). This example extends the studies described in Example 1 and demonstrates that administering a combination of tamoxifen with doxorubicin (Adriamycin) increases anti-tumor activity of tamoxifen. This example thus further demonstrates that the combination of doxorubicin and tamoxifen can be used for precision medicine in triple negative breast cancer (TNBC).

Doxorubicin is well known in the art as a chemotherapeutic agent. Doxorubicin is an anthracycline often used together with other chemotherapies—Adriamycin, Cyclophosphamide, and Taxol (ACT)—to treat TNBC. Doxorubicin is well known in the art to intercalate in DNA, leading to blockage of DNA replication and transcription (Hanna, A. D. et al., Molecular Pharmacology October 2014, 86 (4) 438-449). p73 is responsible for initiating apoptosis in response to doxorubicin in p53-deficient breast cancer cells (Vayssade, M. et al., 2005, Int. J. Cancer 116(6):860-869).

Cardiotoxicity is a major clinical problem and is dependent on cumulative dose of doxorubicin (Hanna, A. D. et al., Molecular Pharmacology October 2014, 86 (4) 438-449). FIG. _ shows that tamoxifen decreases the IC50 (drug concentration required to kill 50% cells) of doxorubicin and that mutant TP53 is responsible for decreased sensitivity to doxorubicin.

FIG. 21A shows that in triple negative breast cancer (TNBC) cells (MDA-MB-231) expressing mutant p53, the IC50 (drug concentration required to kill 50% cells) of doxorubicin is 1.05 UM (grey curve). Addition of tamoxifen decreases the IC50 about 7-fold (0.15 μM) (black curve). In other words, doxorubicin becomes 7 times more efficient in killing cells when combined with tamoxifen. This benefit of adding tamoxifen is lost when the mutant p53 is removed (knocked out) of the cells (FIG. 21B). Tamoxifen counteracts the mutant p53 effect (via ERβ and p'73) (FIG. 21C). Consistent with these findings, cell death increased (measured by increased in Annexin V-positivity) when the drugs are combined, and this effect is dependent on p73 (FIG. 21C).

Furthermore, the combination of Tamoxifen and Doxorubicin is anti-proliferative (FIGS. 22A-C). Cell killing is more pronounced when Tamoxifen and Doxorubicin are combined (FIG. 22A). In two different triple negative breast cancer cell lines, cell killing is greater when Tamoxifen and Doxorubicin are combined (FIG. 22B). This enhanced cell killing effect is absent in a cell line where mutant p53 is knocked out (FIG. 22C).

Mutant p53 thus appears to bind and constrain p'73, a tumor suppressor. When treated with tamoxifen ERβ levels increase, leading to increased sequestration of mutant p53, which in turn leads to reactivation of p73. Such reactivation is further increased because of the response to DNA damage caused by doxorubicin treatment. The activated p73 thus exerts its tumor suppressor activity. FIG. 23 is a diagram of the mechanism of action of this tumor suppression. Growth of TNBC tumors is decreased in an in vivo tumor xenograft model when mutant TP53 is knocked out (FIGS. 24A-B). FIGS. 25A-B show that administration of the combination of tamoxifen and doxorubicin also decreased TNBC tumor growth in the in vivo tumor xenograft model. The combination also enhances the cell-killing effect of doxorubicin several-fold compared to the use of doxorubicin as a single agent or in combination with other chemotherapeutic agents. This enhancement is through an increased reactivation of p73 tumor suppressor.

Conclusion

This example demonstrates that tamoxifen enhances ERβ-mutant TP53 interaction, leading to reactivation of TP73. The addition of tamoxifen lowers several-fold the IC50 of doxorubicin. The combination of tamoxifen and doxorubicin enhances TNBC cell death and is TP73-dependent. Thus, the ERβ-TP53 duo is an important prognostic factor for TNBC. Tamoxifen with (or possibly, in some cases, without) doxorubicin could therefore be used to treat a select group of TNBC (stratified based on expression of ERβ and mutant p53). In combination with tamoxifen, doxorubicin doses can be much lower than what is currently used to treat TNBC. Thus, undesirable side-effects of doxorubicin at currently prescribed doses, such as cardiotoxicity, can be avoided and lead to increased access of the drug to TNBC patients. Tamoxifen is inexpensive and is well known in the art to be one of the most tolerated drugs in clinical use over the decades. New treatments using combinations of tamoxifen with lower doses of doxorubicin can reach patients relatively quickly.

While embodiments of the present disclosure have been particularly shown and described with reference to certain examples and features, it will be understood by one skilled in the art that various changes in detail may be effected therein without departing from the spirit and scope of the present disclosure as defined by claims that can be supported by the written description and drawings. Further, where exemplary embodiments are described with reference to a certain number of elements it will be understood that the exemplary embodiments can be practiced utilizing either less than or more than the certain number of elements.

The citation of any publication is for its disclosure prior to the filing date and should not be construed as an admission that the present invention is not entitled to antedate such publication by virtue of prior invention.

What is claimed is:

1. A method of treating cancer, the method comprising:
selecting a subject having cancer, wherein the cancer is composed of cancer cells expressing estrogen-receptor β (ERβ) and mutant tumor protein 53 (TP53) and not expressing estrogen-receptor α (ERα); and
administering an agent to the selected subject that increases ERB protein expression in the cancer cells, wherein the agent is tamoxifen or a tamoxifen metabolite; and administering at least one drug, sequentially or simultaneously, to the subject, in synergistic combination with the agent, wherein the drug is doxorubicin or carboplatin, wherein the agent and the drug are in amount effective to induce killing of the cancer cells of the subject.

2. The method of claim 1, wherein the cancer is selected from the group consisting of breast cancer, triple-negative breast cancer, lung cancer, ovarian cancer, glioma, and colon cancer, and combinations thereof.

3. The method of claim 1, wherein the increase in ERB protein expression is any detectable amplification of the ERB protein level after the agent is administered to the subject.

4. The method of claim 1, wherein the subject is a cancer patient.

5. The method of claim 4, wherein the selecting step is a stratification of the cancer cells compared to a control and/or clinical guidelines.

6. The method of claim 1, wherein the tamoxifen metabolite is endoxifen.

* * * * *